United States Patent
LaVoie et al.

(10) Patent No.: US 10,836,706 B2
(45) Date of Patent: Nov. 17, 2020

(54) BACTERIAL EFFLUX PUMP INHIBITORS

(71) Applicant: RUTGERS, THE STATE UNIVERSITY OF NEW JERSEY, New Brunswick, NJ (US)

(72) Inventors: Edmond J. LaVoie, New Brunswick, NJ (US); Ajit Parhi, New Brunswick, NJ (US); Gifty A. Blankson, New Brunswick, NJ (US); Liping Wang, Monmouth Junction, NJ (US); Xiao Chen, Monmouth Junction, NJ (US); Yongzheng Zhang, Monmouth Junction, NJ (US); Malvika Kaul, New Brunswick, NJ (US); Daniel S. Pilch, New Brunswick, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 16/078,572

(22) PCT Filed: Feb. 23, 2017

(86) PCT No.: PCT/US2017/019198
§ 371 (c)(1),
(2) Date: Aug. 21, 2018

(87) PCT Pub. No.: WO2017/147335
PCT Pub. Date: Aug. 31, 2017

(65) Prior Publication Data
US 2019/0055188 A1    Feb. 21, 2019

Related U.S. Application Data

(60) Provisional application No. 62/299,450, filed on Feb. 24, 2016.

(51) Int. Cl.
| C07C 211/63 | (2006.01) |
| C07C 217/42 | (2006.01) |
| A61K 31/14 | (2006.01) |
| A61K 45/06 | (2006.01) |
| A61P 31/04 | (2006.01) |
| A61K 31/137 | (2006.01) |
| A61K 31/138 | (2006.01) |
| C07C 211/27 | (2006.01) |
| C07C 211/29 | (2006.01) |

(52) U.S. Cl.
CPC .......... *C07C 211/63* (2013.01); *A61K 31/137* (2013.01); *A61K 31/138* (2013.01); *A61K 31/14* (2013.01); *A61K 45/06* (2013.01); *A61P 31/04* (2018.01); *C07C 211/27* (2013.01); *C07C 211/29* (2013.01); *C07C 217/42* (2013.01); *Y02A 50/475* (2018.01)

(58) Field of Classification Search
CPC ... C07C 211/63; C07C 211/27; C07C 211/29; C07C 217/42; A61P 31/04; A61K 31/137; A61K 31/138; A61K 31/14; A61K 45/06; Y02A 50/475
USPC .......................................................... 514/653
See application file for complete search history.

(56) References Cited

U.S. PATENT DOCUMENTS

| 4,826,861 | A  | * | 5/1989  | Gerard ................. C07D 319/20 514/371 |
| 7,812,047 | B2 | * | 10/2010 | Galley ................. C07D 233/06 514/399 |
| 8,642,076 | B2 |   | 2/2014  | Manoharan et al. |
| 9,926,261 | B2 |   | 3/2018  | Lavoie et al. |
| 9,950,993 | B2 |   | 4/2018  | Lavoie et al. |
| 2004/0204378 | A1 | | 10/2004 | Nelson et al. |
| 2013/0296228 | A1 | | 11/2013 | Patel et al. |
| 2019/0031624 | A1 | | 1/2019  | Lavoie et al. |
| 2019/0084919 | A1 | | 3/2019  | Lavoie et al. |

FOREIGN PATENT DOCUMENTS

| WO | 2005113579 A1 | 12/2005 |
| WO | 2018165611 A1 | 9/2018 |
| WO | 2018165612 A1 | 9/2018 |
| WO | 2018165614 A1 | 9/2018 |
| WO | 2018218192 A1 | 11/2018 |
| WO | 2019005841 A1 | 1/2019 |

OTHER PUBLICATIONS

Patent Cooperation Treaty, International Searching Authority, Search Report and Written Opinion for PCT/US2017/019198, 10 pages, Jun. 15, 2017.

* cited by examiner

*Primary Examiner* — Krisitn A Vajda
(74) *Attorney, Agent, or Firm* — Viksins Harris Padys Malen LLP

(57) ABSTRACT

Disclosed herein are compounds of formula I: and salts thereof. Also disclosed are compositions comprising compounds of formula I and methods using compounds of formula I.

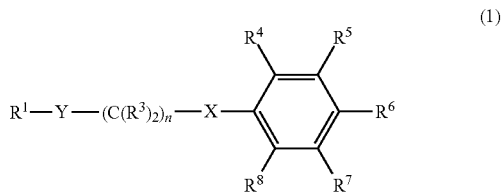

19 Claims, No Drawings

BACTERIAL EFFLUX PUMP INHIBITORS

PRIORITY OF INVENTION

This application claims priority from U.S. Provisional Patent Application No. 62/299,450 filed Feb. 24, 2016, which is hereby incorporated by reference in its entirety.

BACKGROUND OF THE INVENTION

Antibiotics have been effective tools in the treatment of infectious diseases. However, bacteria have developed several different mechanisms to overcome the action of antibiotics. These mechanisms of resistance can be specific such as for a molecule or a family of antibiotics, or the mechanisms can be non-specific. Several mechanisms of resistance can exist in a single bacterial strain, and those mechanisms may act independently or they may act synergistically to overcome the action of an antibiotic or a combination of antibiotics. Specific mechanisms include, for example, degradation of the drug, inactivation of the drug by enzymatic modification, and alteration of the drug target. Additional mechanisms of drug resistance include mechanisms in which access of the antibiotic to the target is prevented or reduced by decreasing the transport of the antibiotic into the cell or by increasing the efflux of the drug from the cell to the outside medium. Both of these mechanisms can lower the concentration of drug at the target site and allow bacterial survival in the presence of one or more antibiotics that would otherwise inhibit or kill the bacterial cells. Some bacteria utilize both mechanisms, combining low permeability of the cell wall (including membranes) with an active efflux of antibiotics. It has been shown that efflux of antibiotics can be mediated by more than one pump in a single organism and that almost all antibiotics are subject to resistance by this mechanism.

These multiple resistance mechanisms have become widespread and threaten the clinical utility of antibacterial therapy. The increase in antibiotic resistant strains has been particularly noted in major hospitals and care centers. The consequences of the increase in resistant strains include, for example higher morbidity and mortality, longer patient hospitalization, and an increase in treatment costs. Accordingly, there is a need for agents and methods for inhibiting one or more of these mechanisms of bacterial resistance.

SUMMARY OF THE INVENTION

Compounds disclose herein, when tested in combination with a known antibiotic, lower the minimum inhibitory concentration of the known antibiotic to inhibit bacterial cell growth. Not to be bound by theory the compounds are believed to exert this effect by the inhibition of a bacterial efflux pump(s).

Accordingly, one embodiment provides a compound of formula I:

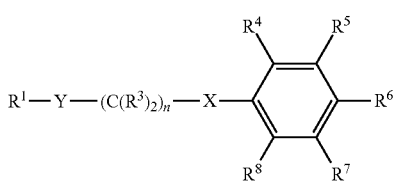

wherein:
X is $-C(R^2)_2-$, Y is $-N(R^{a1})-$ or $-C(H)(NR^{b1}R^{c1})-$ and n is 0 or 1, or X is $-O-$, Y is $-C(H)(NR^{b1}R^{c1})-$ and n is 1 or 2;

$R^1$ is $(C_1-C_8)$alkyl substituted with one or more groups selected from $-NR^{b2}R^{c2}$, $-NHNH_2$, $-C(=NR^{a2})(NR^{b2}R^{c2})$, $-NR^{a2}C(=NR^{a2})(R^{a2})$ and $-NR^{a2}C(=NR^{a2})(NR^{b2}R^{c2})$;

each $R^2$ is independently hydrogen, halo or $(C_1-C_4)$alkyl;
each $R^3$ is independently hydrogen, halo or $(C_1-C_4)$alkyl;
$R^4$ is hydrogen, halo, $(C_1-C_6)$alkyl, $(C_1-C_6)$haloalkyl, $(C_1-C_6)$alkoxy, $(C_1-C_4)$haloalkoxy, aryl or heteroaryl wherein the aryl or heteroaryl is optionally substituted with one or more groups independently selected from halo, $(C_1-C_4)$alkyl, $(C_1-C_4)$haloalkyl, $(C_1-C_4)$alkoxy and $(C_1-C_4)$haloalkoxy;
$R^5$ is hydrogen, halo, $(C_1-C_6)$alkyl, $(C_1-C_6)$haloalkyl, $(C_1-C_6)$alkoxy, $(C_1-C_4)$haloalkoxy, aryl or heteroaryl wherein the aryl or heteroaryl is optionally substituted with one or more groups independently selected from halo, $(C_1-C_4)$alkyl, $(C_1-C_4)$haloalkyl, $(C_1-C_4)$alkoxy and $(C_1-C_4)$haloalkoxy;
$R^6$ is hydrogen, halo, $(C_1-C_6)$alkyl, $(C_1-C_6)$haloalkyl, $(C_1-C_6)$alkoxy, $(C_1-C_4)$haloalkoxy, aryl or heteroaryl wherein the aryl or heteroaryl is optionally substituted with one or more groups independently selected from halo, $(C_1-C_4)$alkyl, $(C_1-C_4)$haloalkyl, $(C_1-C_4)$alkoxy and $(C_1-C_4)$haloalkoxy;
$R^7$ is hydrogen, halo, $(C_1-C_6)$alkyl, $(C_1-C_6)$haloalkyl, $(C_1-C_6)$alkoxy, $(C_1-C_4)$haloalkoxy, aryl or heteroaryl wherein the aryl or heteroaryl is optionally substituted with one or more groups independently selected from halo, $(C_1-C_4)$alkyl, $(C_1-C_4)$haloalkyl, $(C_1-C_4)$alkoxy and $(C_1-C_4)$haloalkoxy;
$R^8$ is hydrogen, halo, $(C_1-C_6)$alkyl, $(C_1-C_6)$haloalkyl, $(C_1-C_6)$alkoxy, $(C_1-C_4)$haloalkoxy, aryl or heteroaryl wherein the aryl or heteroaryl is optionally substituted with one or more groups independently selected from halo, $(C_1-C_4)$alkyl, $(C_1-C_4)$haloalkyl, $(C_1-C_4)$alkoxy and $(C_1-C_4)$haloalkoxy;
$R^{a1}$ is hydrogen or $(C_1-C_4)$alkyl, wherein the $(C_1-C_4)$alkyl is optionally substituted with one or more $-NR^{b3}R^{c3}$;
$R^{b1}$ and $R^{c1}$ are each independently hydrogen or $(C_1-C_4)$alkyl;
each $R^{a2}$ is independently hydrogen or $(C_1-C_4)$alkyl;
each $R^{b2}$ and $R^{c2}$ is independently hydrogen or $(C_1-C_4)$alkyl;
$R^{d2}$ is $(C_1-C_3)$alkyl; and
each $R^{b3}$ and $R^{c3}$ is independently hydrogen or $(C_1-C_4)$alkyl;
or a salt thereof.

One embodiment provides a compound of formula I:

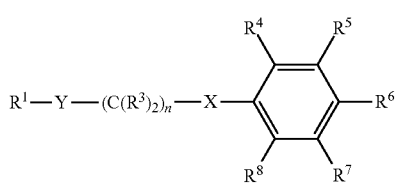

wherein:
X is $-C(R^2)_2-$, Y is $-N(R^{a1})-$ or $-C(H)(NR^{b1}R^{c1})-$ and n is 0 or 1, or X is $-O-$, Y is $-C(H)(NR^{b1}R^{c1})-$ and n is 1;

$R^1$ is $(C_1-C_5)$alkyl substituted with one or more groups selected from —$NR^{b2}R^{c2}$, —$NHNH_2$, —$C(=NR^{a2})(NR^{b2}R^{c2})$, —$NR^{a2}C(=NR^{a2})(R^{d2})$ and —$NR^{a2}C(=NR^{a2})(NR^{b2}R^{c2})$;

each $R^2$ is independently hydrogen, halo or $(C_1-C_4)$alkyl;

each $R^3$ is independently hydrogen, halo or $(C_1-C_4)$alkyl;

$R^4$ is hydrogen, halo, $(C_1-C_6)$alkyl, $(C_1-C_6)$haloalkyl, $(C_1-C_6)$alkoxy, $(C_1-C_4)$haloalkoxy, aryl or heteroaryl wherein the aryl or heteroaryl is optionally substituted with one or more groups independently selected from halo, $(C_1-C_4)$alkyl, $(C_1-C_4)$haloalkyl, $(C_1-C_4)$alkoxy and $(C_1-C_4)$haloalkoxy;

$R^5$ is hydrogen, halo, $(C_1-C_6)$alkyl, $(C_1-C_6)$haloalkyl, $(C_1-C_6)$alkoxy, $(C_1-C_4)$haloalkoxy, aryl or heteroaryl wherein the aryl or heteroaryl is optionally substituted with one or more groups independently selected from halo, $(C_1-C_4)$alkyl, $(C_1-C_4)$haloalkyl, $(C_1-C_4)$alkoxy and $(C_1-C_4)$haloalkoxy;

$R^6$ is hydrogen, halo, $(C_1-C_6)$alkyl, $(C_1-C_6)$haloalkyl, $(C_1-C_6)$alkoxy, $(C_1-C_4)$haloalkoxy, aryl or heteroaryl wherein the aryl or heteroaryl is optionally substituted with one or more groups independently selected from halo, $(C_1-C_4)$alkyl, $(C_1-C_4)$haloalkyl, $(C_1-C_4)$alkoxy and $(C_1-C_4)$haloalkoxy;

$R^7$ is hydrogen, halo, $(C_1-C_6)$alkyl, $(C_1-C_6)$haloalkyl, $(C_1-C_6)$alkoxy, $(C_1-C_4)$haloalkoxy, aryl or heteroaryl wherein the aryl or heteroaryl is optionally substituted with one or more groups independently selected from halo, $(C_1-C_4)$alkyl, $(C_1-C_4)$haloalkyl, $(C_1-C_4)$alkoxy and $(C_1-C_4)$haloalkoxy;

$R^8$ is hydrogen, halo, $(C_1-C_6)$alkyl, $(C_1-C_6)$haloalkyl, $(C_1-C_6)$alkoxy, $(C_1-C_4)$haloalkoxy, aryl or heteroaryl wherein the aryl or heteroaryl is optionally substituted with one or more groups independently selected from halo, $(C_1-C_4)$alkyl, $(C_1-C_4)$haloalkyl, $(C_1-C_4)$alkoxy and $(C_1-C_4)$haloalkoxy;

$R^{a1}$ is hydrogen or $(C_1-C_4)$alkyl, wherein the $(C_1-C_4)$alkyl is optionally substituted with one or more —$NR^{b3}R^{c3}$;

$R^{b1}$ and $R^{c1}$ are each independently hydrogen or $(C_1-C_4)$alkyl;

each $R^{a2}$ is independently hydrogen or $(C_1-C_4)$alkyl;

each $R^{b2}$ and $R^{c2}$ is independently hydrogen or $(C_1-C_4)$alkyl;

$R^{d2}$ is $(C_1-C_3)$alkyl; and each $R^{b3}$ and $R^{c3}$ is independently hydrogen or $(C_1-C_4)$alkyl;

or a salt thereof.

One embodiment provides a pharmaceutical composition comprising a compound of formula I or a pharmaceutically acceptable salt thereof as described herein, and a pharmaceutically acceptable vehicle.

One embodiment provides pharmaceutical composition comprising a compound of formula I or a pharmaceutically acceptable salt thereof as described herein, one or more antibacterial agents and a pharmaceutically acceptable vehicle.

One embodiment provides a method of inhibiting a bacterial efflux pump in an animal (e.g., a mammal such as a human) comprising administering to the animal a compound of formula I or a pharmaceutically acceptable salt thereof as described herein.

One embodiment provides a method of inhibiting a bacterial efflux pump in an animal (e.g., a mammal such as a human) comprising administering to the animal in need thereof a compound of formula I or a pharmaceutically acceptable salt thereof as described herein.

One embodiment provides a method of treating or preventing a bacterial infection in an animal (e.g., a mammal such as a human) comprising co-administering to the animal a compound of formula I or a pharmaceutically acceptable salt thereof as described herein and one or more antibacterial agents.

One embodiment provides a method of treating or preventing a bacterial infection in an animal (e.g., a mammal such as a human) comprising co-administering to the animal in need thereof a compound of formula I or a pharmaceutically acceptable salt thereof as described herein and one or more antibacterial agents.

One embodiment provides a method of inhibiting a bacterial efflux pump in an animal (e.g., a mammal such as a human) with a bacterial infection comprising administering to the animal a compound of formula I or a pharmaceutically acceptable salt thereof as described herein.

One embodiment provides a method of treating or preventing a bacterial infection in an animal (e.g., a mammal such as a human) infected with bacteria comprising co-administering to the animal a compound of formula I or a pharmaceutically acceptable salt thereof as described herein and one or more antibacterial agents.

One embodiment provides a compound of formula I or a pharmaceutically acceptable salt thereof as described herein for use in medical treatment.

One embodiment provides a compound of formula I or a pharmaceutically acceptable salt thereof as described herein for the prophylactic or therapeutic inhibition of a bacterial efflux pump for the treatment of a bacterial infection.

One embodiment provides a compound of formula I or a pharmaceutically acceptable salt thereof as described herein which is used in combination with one or more antibacterial agents for the prophylactic or therapeutic treatment of a bacterial infection.

One embodiment provides the use of a compound of formula I or a pharmaceutically acceptable salt thereof as described herein for the preparation of a medicament for inhibiting a bacterial efflux pump.

One embodiment provides the use of a compound of formula I or a pharmaceutically acceptable salt thereof as described herein for the preparation of a medicament for treating a bacterial infection in an animal (e.g., a mammal such as a human).

One embodiment provides the use of a compound of formula I or a pharmaceutically acceptable salt thereof as described herein for the preparation of a medicament which is used in combination with one or more antibacterial agents for treating a bacterial infection in an animal (e.g., a mammal such as a human).

One embodiment provides processes and intermediates disclosed herein that are useful for preparing compounds of formula I or salts thereof.

DETAILED DESCRIPTION

The following definitions are used, unless otherwise described: halo or halogen is fluoro, chloro, bromo, or iodo. Alkyl and alkoxy, etc. denote both straight and branched groups but reference to an individual radical such as propyl embraces only the straight chain radical (a branched chain isomer such as isopropyl being specifically referred to).

As used herein, the term "$(C_a-C_b)$alkyl" wherein a and b are integers refers to a straight or branched chain alkyl radical having from a to b carbon atoms. Thus when a is 1 and b is 6, for example, the term includes methyl, ethyl, n-propyl, isopropyl, n-butyl, isobutyl, sec-butyl, t-butyl, n-pentyl and n-hexyl.

The term "aryl" as used herein refers to a single aromatic ring or a multiple condensed ring system wherein the ring atoms are carbon. For example, an aryl group can have 6 to 10 carbon atoms, or 6 to 12 carbon atoms. Aryl includes a phenyl radical. Aryl also includes multiple condensed ring systems (e.g., ring systems comprising 2 rings) having about 9 to 12 carbon atoms or 9 to 10 carbon atoms in which at least one ring is aromatic. Such multiple condensed ring systems may be optionally substituted with one or more (e.g., 1 or 2) oxo groups on any cycloalkyl portion of the multiple condensed ring system. It is to be understood that the point of attachment of a multiple condensed ring system, as defined above, can be at any position of the ring system including an aryl or a cycloalkyl portion of the ring. Typical aryl groups include, but are not limited to, phenyl, indenyl, naphthyl, 1, 2, 3, 4-tetrahydronaphthyl, anthracenyl, and the like.

The term "heteroaryl" as used herein refers to a single aromatic ring or a multiple condensed ring system. The term includes single aromatic rings of from about 1 to 6 carbon atoms and about 1-4 heteroatoms selected from the group consisting of oxygen, nitrogen and sulfur in the rings. The sulfur and nitrogen atoms may also be present in an oxidized form provided the ring is aromatic. Such rings include but are not limited to pyridyl, pyrimidinyl, oxazolyl or furyl. The term also includes multiple condensed ring systems (e.g. ring systems comprising 2 rings) wherein a heteroaryl group, as defined above, can be condensed with one or more heteroaryls (e.g., naphthyridinyl), heterocycles, (e.g., 1, 2, 3, 4-tetrahydronaphthyridinyl), cycloalkyls (e.g., 5,6,7,8-tetrahydroquinolyl) or aryls (e.g. indazolyl) to form a multiple condensed ring system. Such multiple condensed ring systems may be optionally substituted with one or more (e.g., 1 or 2) oxo groups on the cycloalkyl or heterocycle portions of the condensed ring. In one embodiment a monocyclic or bicyclic heteroaryl has 5 to 10 ring atoms comprising 1 to 9 carbon atoms and 1 to 4 heteroatoms. It is to be understood that the point of attachment of a multiple condensed ring system (as defined above for a heteroaryl) can be at any position of the multiple condensed ring system including a heteroaryl, heterocycle, aryl or cycloalkyl portion of the multiple condensed ring system and at any suitable atom of the multiple condensed ring system including a carbon atom and heteroatom (e.g., a nitrogen). Exemplary heteroaryls include but are not limited to pyridyl, pyrrolyl, pyrazinyl, pyrimidinyl, pyridazinyl, pyrazolyl, thienyl, indolyl, imidazolyl, oxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl, benzofuranyl, benzimidazolyl and thianaphthenyl.

The term "heterocyclyl" or "heterocycle" as used herein refers to a single saturated or partially unsaturated ring or a multiple condensed ring system. The term includes single saturated or partially unsaturated rings (e.g., 3, 4, 5, 6 or 7-membered rings) from about 1 to 6 carbon atoms and from about 1 to 3 heteroatoms selected from the group consisting of oxygen, nitrogen and sulfur in the ring. The ring may be substituted with one or more (e.g., 1, 2 or 3) oxo groups and the sulfur and nitrogen atoms may also be present in their oxidized forms. Such rings include but are not limited to azetidinyl, tetrahydrofuranyl or piperidinyl. It is to be understood that the point of attachment for a heterocycle can be at any suitable atom of the heterocycle Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl and tetrahydrothiopyranyl.

The term "haloalkyl" includes an alkyl group as defined herein that is substituted with one or more (e.g., 1, 2, 3, or 4) halo groups. One specific halo alkyl is a "$(C_1-C_6)$ haloalkyl".

The term cycloalkyl includes saturated and partially unsaturated carbocyclic ring systems. In one embodiment the cycloalkyl is a monocyclic carbocyclic ring. One such cycloalkyl is a "$(C_3-C_8)$cycloalkyl".

Specific values listed below for radicals, substituents, and ranges, are for illustration only; they do not exclude other defined values or other values within defined ranges for the radicals and substituents.

Specifically, $(C_1-C_6)$alkyl can be methyl, ethyl, propyl, isopropyl, butyl, iso-butyl, sec-butyl, pentyl, 3-pentyl, or hexyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_3-C_8)$cycloalkyl can be cyclopropyl, cyclobutyl, cyclopentyl, or cyclohexyl; $(C_1-C_6)$haloalkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; aryl can be phenyl, indenyl, or naphthyl; and heteroaryl can be furyl, imidazolyl, triazolyl, triazinyl, oxazolyl, isoxazolyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

It is to be understood that the embodiments provided below are for compounds of formula I and all sub-formulas thereof (e.g., formulas Ia, Ib, Ic, Id, Ie, If, Ig, Ih). It is to be understood the two or more embodiments may be combined.

In one embodiment $R^4$ is hydrogen.
In one embodiment $R^8$ is hydrogen.
In one embodiment $R^6$ is hydrogen.
In one embodiment a compound of formula I is a compound formula Ia:

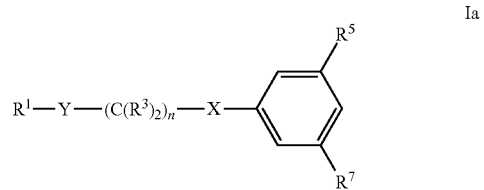

Ia or a salt thereof.

In one embodiment $R^5$ is halo, $(C_1-C_6)$alkyl, $(C_1-C_6)$ haloalkyl, $(C_1-C_6)$alkoxy, $(C_1-C_4)$haloalkoxy, aryl or heteroaryl wherein the aryl or heteroaryl is optionally substituted with one or more groups independently selected from halo, $(C_1-C_4)$alkyl, $(C_1-C_4)$haloalkyl, $(C_1-C_4)$alkoxy and $(C_1-C_4)$haloalkoxy.

In one embodiment $R^5$ is $(C_1-C_6)$alkyl, $(C_1-C_6)$haloalkyl, or aryl wherein the aryl is optionally substituted with one or more groups independently selected from halo, $(C_1-C_4)$ alkyl, $(C_1-C_4)$haloalkyl, $(C_1-C_4)$alkoxy and $(C_1-C_4)$haloalkoxy.

In one embodiment $R^5$ is $(C_1-C_6)$alkyl, $(C_1-C_6)$haloalkyl, or phenyl wherein phenyl is optionally substituted with one or more groups independently selected from halo, $(C_1-C_4)$ alkyl, $(C_1-C_4)$haloalkyl, $(C_1-C_4)$alkoxy and $(C_1-C_4)$haloalkoxy.

In one embodiment R⁵ is tert-butyl, —CF₃, phenyl, 4-trifluoromethylphenyl or 4-fluorophenyl.

In one embodiment R⁵ is tert-butyl, —CF₃, phenyl, 4-trifluoromethylphenyl, 4-fluorophenyl, 4-methoxyphenyl, 3-fluorophenyl, or 3,4-difluorophenyl.

In one embodiment R⁷ is halo, (C₁-C₆)alkyl, (C₁-C₆)haloalkyl, (C₁-C₆)alkoxy, (C₁-C₄)haloalkoxy, aryl or heteroaryl wherein the aryl or heteroaryl is optionally substituted with one or more groups independently selected from halo, (C₁-C₄)alkyl, (C₁-C₄)haloalkyl, (C₁-C₄)alkoxy and (C₁-C₄)haloalkoxy.

In one embodiment R⁷ is (C₁-C₆)alkyl, (C₁-C₆)haloalkyl or aryl wherein the aryl is optionally substituted with one or more groups independently selected from halo, (C₁-C₄)alkyl, (C₁-C₄)haloalkyl, (C₁-C₄)alkoxy and (C₁-C₄)haloalkoxy.

In one embodiment R⁷ is (C₁-C₆)alkyl, (C₁-C₆)haloalkyl, or phenyl wherein phenyl is optionally substituted with one or more groups independently selected from halo, (C₁-C₄)alkyl, (C₁-C₄)haloalkyl, (C₁-C₄)alkoxy and (C₁-C₄)haloalkoxy.

In one embodiment R⁷ is tert-butyl, —CF₃, phenyl, 4-trifluoromethylphenyl or 4-fluorophenyl.

In one embodiment R⁷ is tert-butyl, —CF₃, phenyl, 4-trifluoromethylphenyl, 4-fluorophenyl, 4-methoxyphenyl, 3-fluorophenyl, or 3,4-difluorophenyl.

In one embodiment R⁷ is hydrogen.

In one embodiment a compound of formula I is a compound formula Ib:

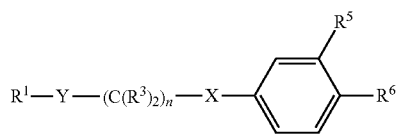

or a salt thereof.

In one embodiment the moiety:

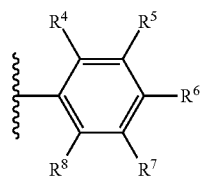

of the compound of formula I is:

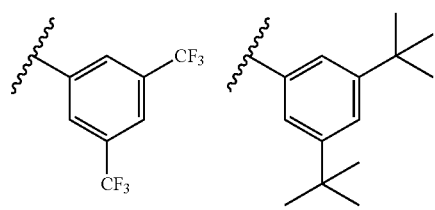

In one embodiment the moiety:

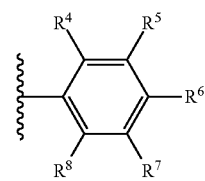

of the compound of formula I is:

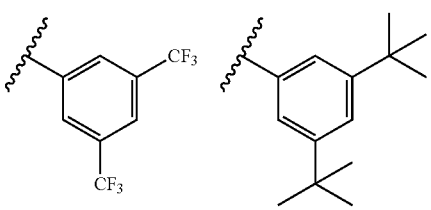

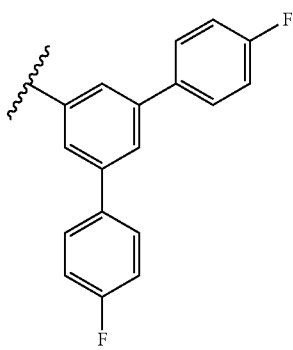

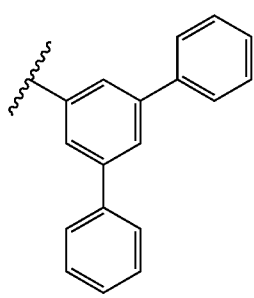

or

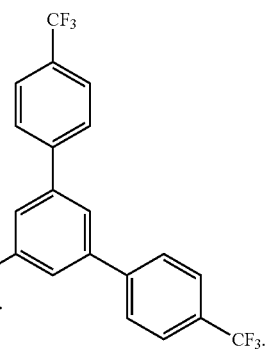

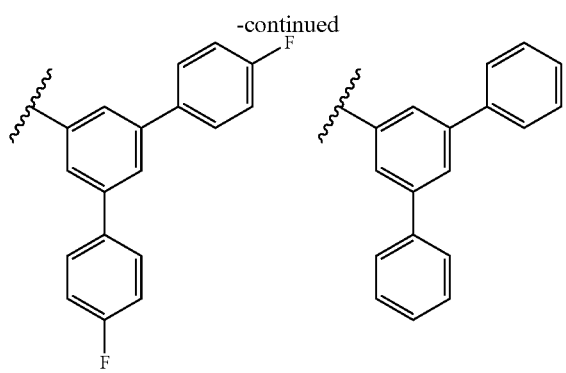

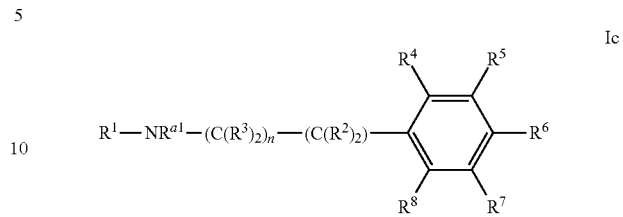

In one embodiment X is —C(R²)₂—, Y is —N(R^{a1})— or —C(H)(NR^{b1}R^{c1})— and n is 0 or 1.

In one embodiment Y is —N(R^{a1})—.
In one embodiment a compound of formula I is a compound formula Ic:

$$R^1-NR^{a1}-(C(R^3)_2)_n-(C(R^2)_2)-\underset{R^8\ R^7}{\overset{R^4\ R^5}{\bigcirc}}-R^6 \qquad \text{Ic}$$

or a salt thereof.
In one embodiment a compound of formula I is a compound formula Id:

$$R^1-NR^{a1}-(C(R^3)_2)_n-(C(R^2)_2)-\underset{R^7}{\overset{R^5}{\bigcirc}} \qquad \text{Id}$$

or a salt thereof.
In one embodiment R^{a1} is hydrogen or (C₁-C₄)alkyl, wherein the (C₁-C₄)alkyl is substituted with one or more —NR^{b3}R^{c3}.
In one embodiment wherein R^{a1} is hydrogen.
In one embodiment R^{a1} is (C₁-C₄)alkyl substituted with one or more —NR^{b3}R^{c3}.
In one embodiment R^{b3} and R^{c3} are each hydrogen.
In one embodiment Y is —C(H)(NR^{b1}R^{c1})—.
In one embodiment a compound of formula I is a compound formula Ie:

$$R^1-\underset{(C(R^3)_2)_n}{\overset{NR^{b1}R^{c1}}{|}}-(C(R^2)_2)-\underset{R^8\ R^7}{\overset{R^4\ R^5}{\bigcirc}}-R^6 \qquad \text{Ie}$$

or a salt thereof.
In one embodiment a compound of formula I is a compound formula If:

$$R^1-\underset{(C(R^3)_2)_n}{\overset{NR^{b1}R^{c1}}{|}}-(C(R^2)_2)-\underset{R^7}{\overset{R^5}{\bigcirc}} \qquad \text{If}$$

or a salt thereof.
In one embodiment each R² is independently hydrogen or methyl.
In one embodiment X is —O—, Y is —C(H)(NR^{b1}R^{c1})— and n is 1.

In one embodiment a compound of formula I is a compound formula Ig:

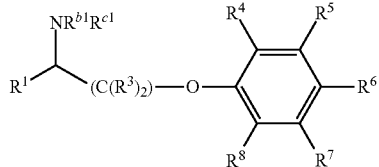

or a salt thereof.

In one embodiment a compound of formula I is a compound formula Ih:

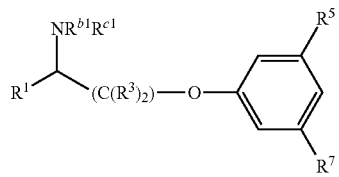

or a salt thereof.

In one embodiment $R^{b1}$ and $R^{c1}$ are each hydrogen.

In one embodiment each $R^3$ is hydrogen.

In one embodiment $R^1$ is $(C_1-C_5)$alkyl substituted with one or more groups independently selected from $-NR^{b2}R^{c2}$.

In one embodiment $R^1$ is $(C_2-C_8)$alkyl substituted with two or more groups independently selected from $-NR^{b2}R^{c2}$.

In one embodiment $R^1$ is $(C_1-C_6)$alkyl substituted with one or more groups independently selected from $-NR^{b2}R^{c2}$.

In one embodiment $R^1$ is $(C_2-C_6)$alkyl substituted with two or more groups independently selected from $-NR^{b2}R^{c2}$.

In one embodiment $R^{b2}$ and $R^{c2}$ are each hydrogen.

In one embodiment the moiety:

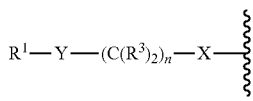

of the compound of formula I is:

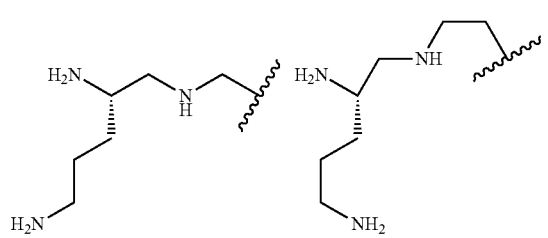

-continued

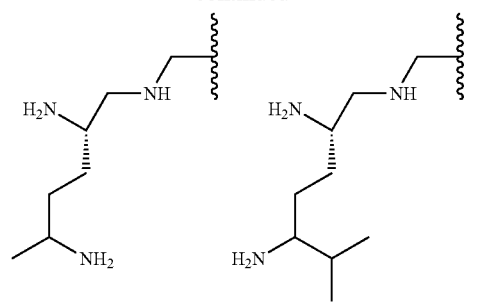

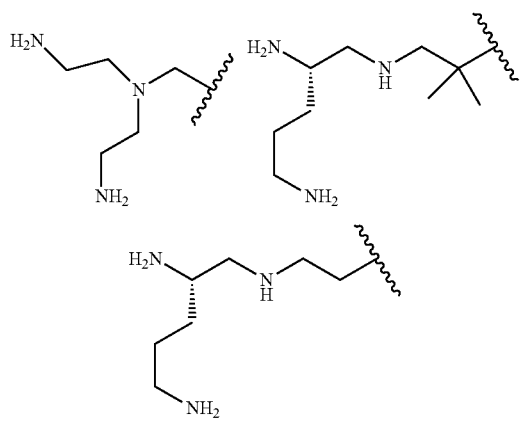

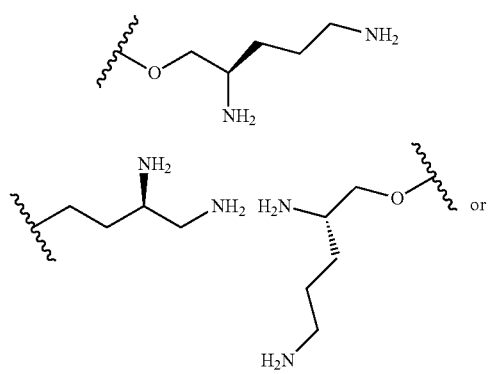

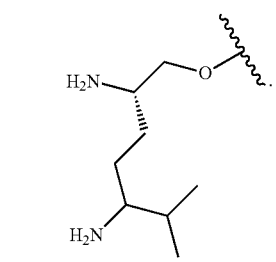

In one embodiment a compound of formula I is:

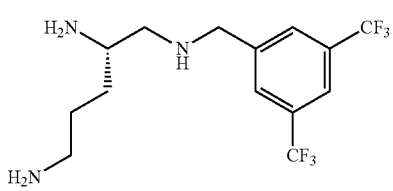

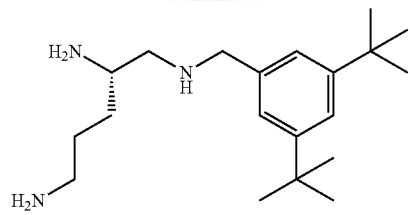
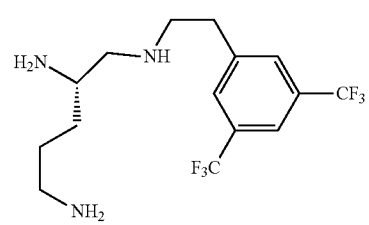
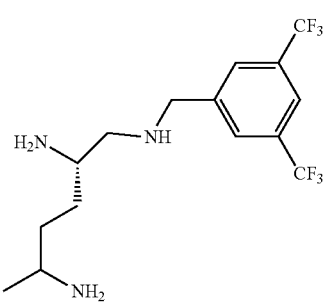
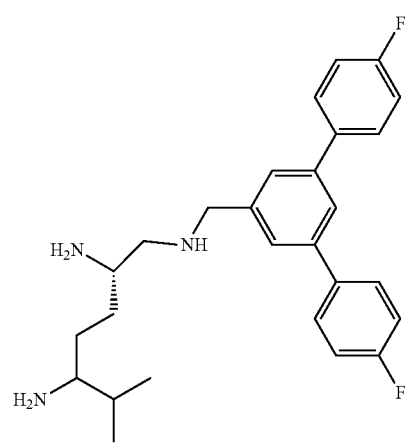
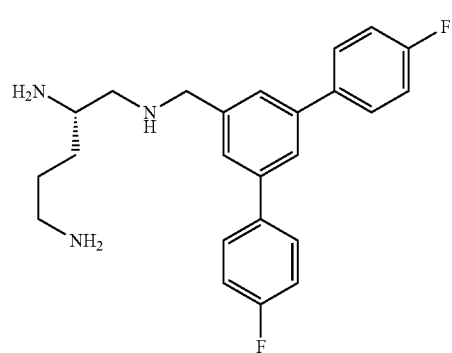
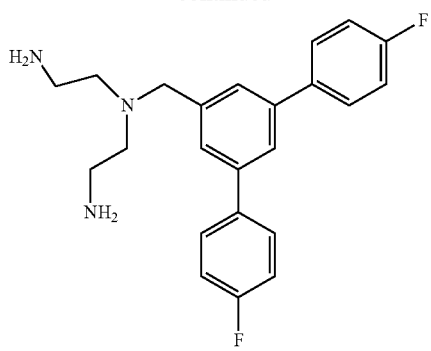
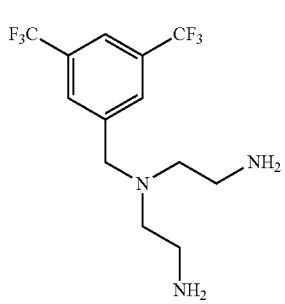
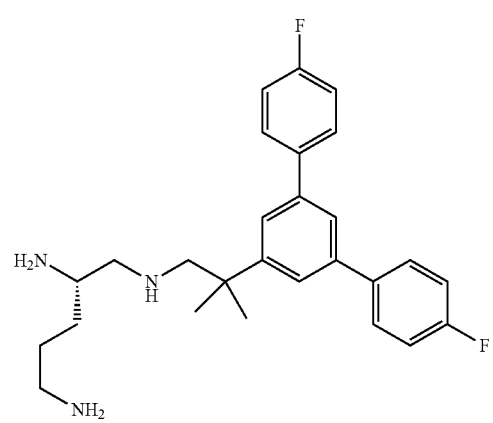
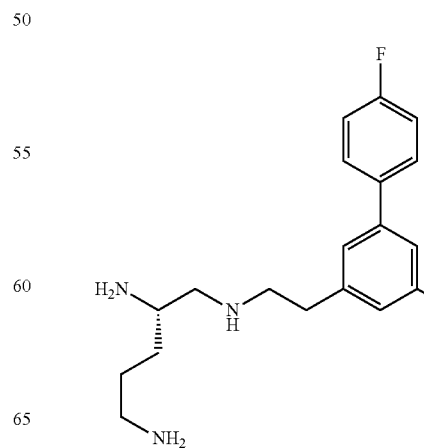

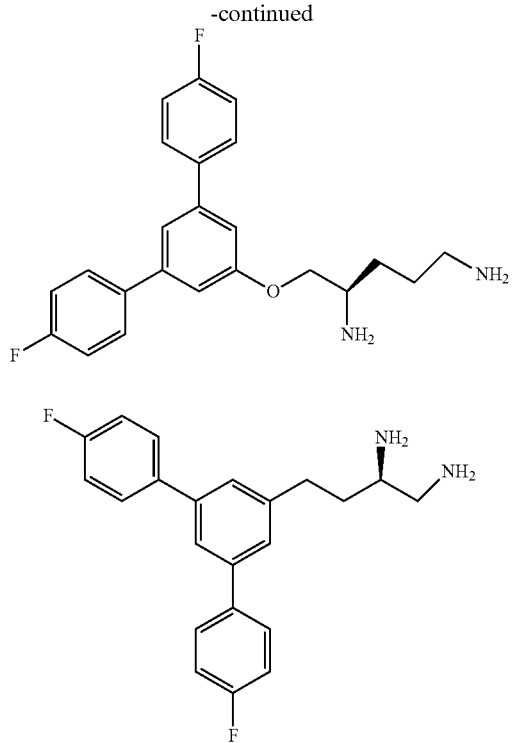
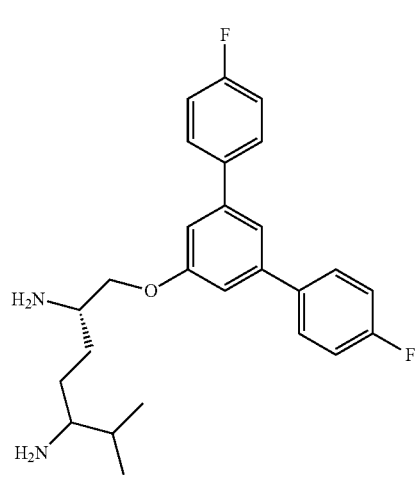
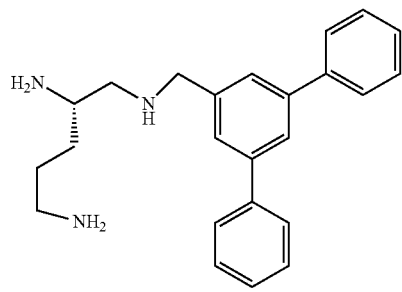
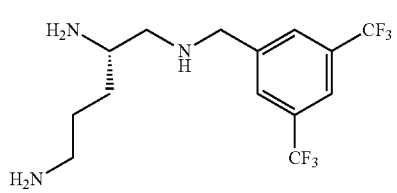
or a salt thereof.
In one embodiment a compound of formula I is:
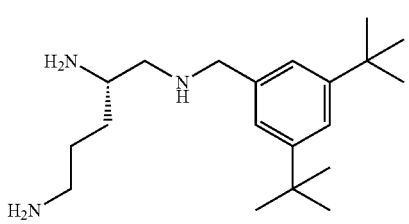

-continued
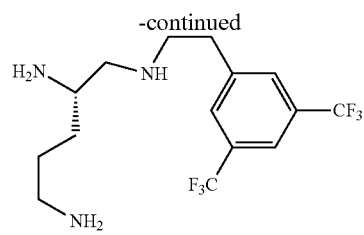
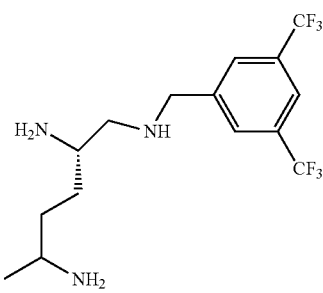
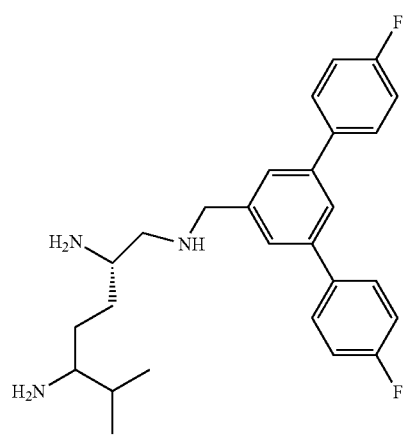
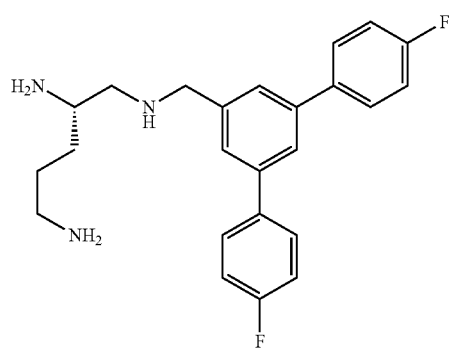
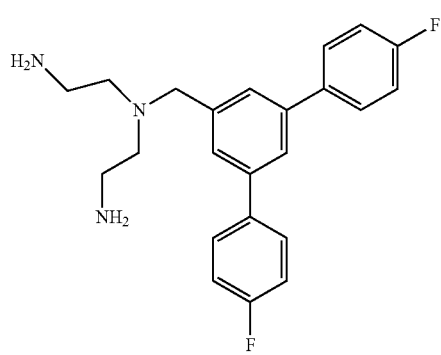
-continued
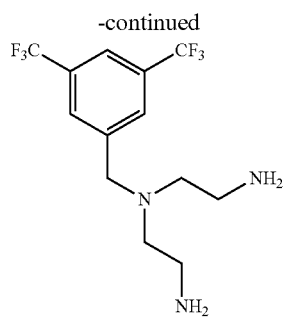
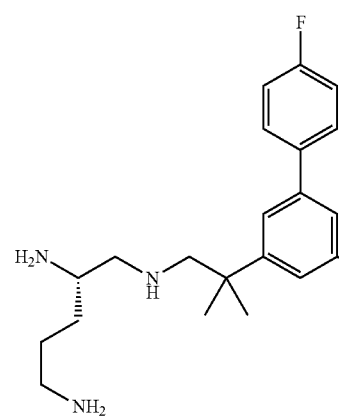
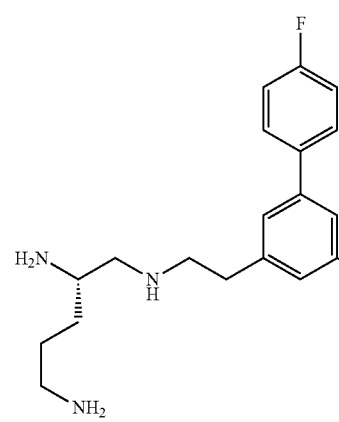
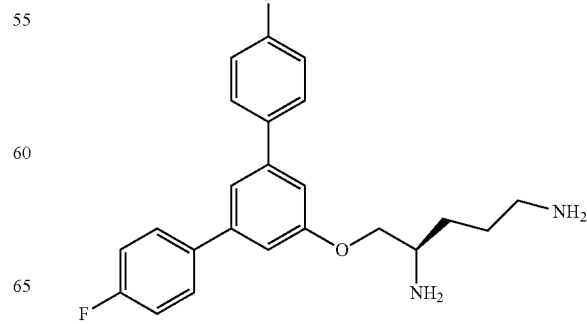

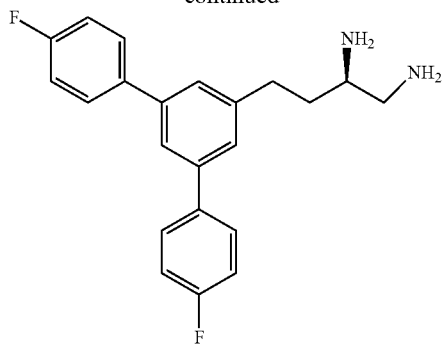
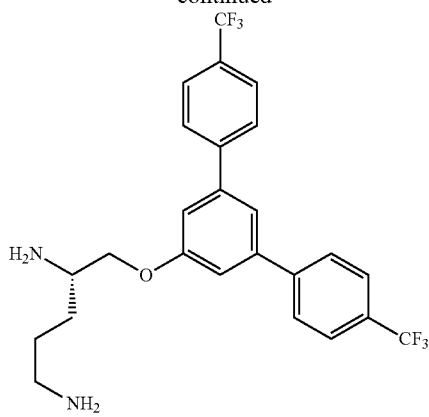
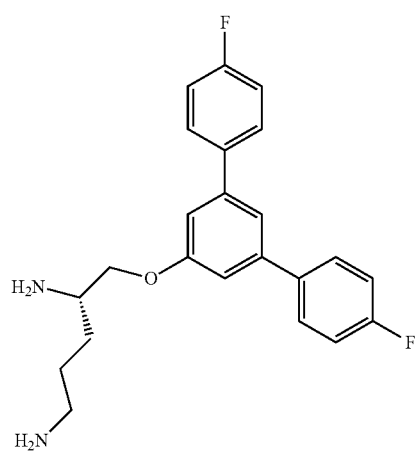
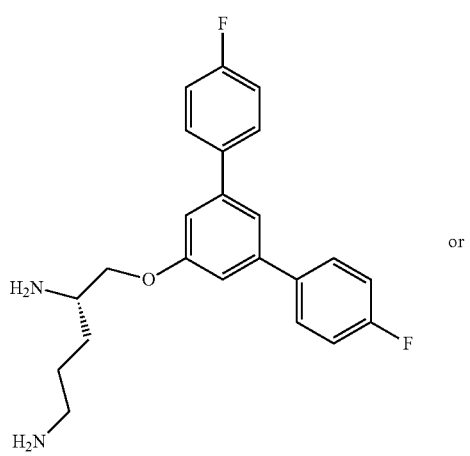
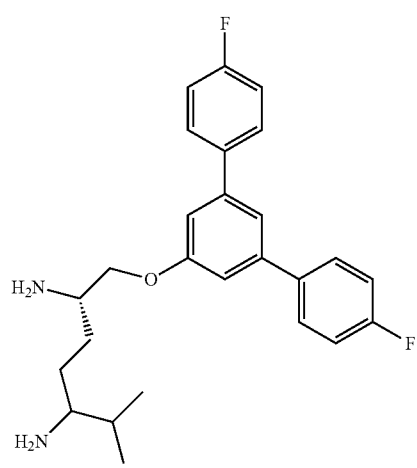
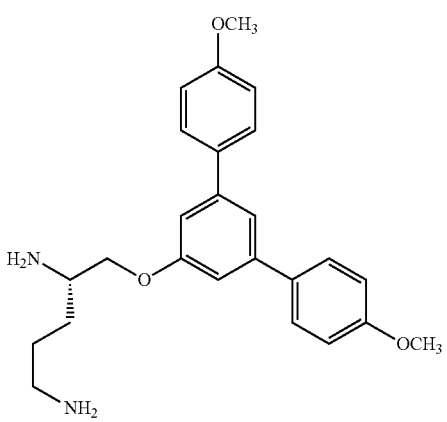
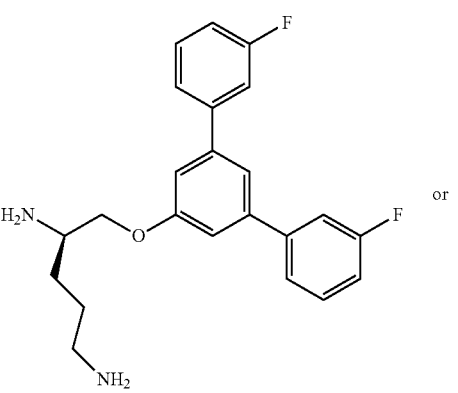
or

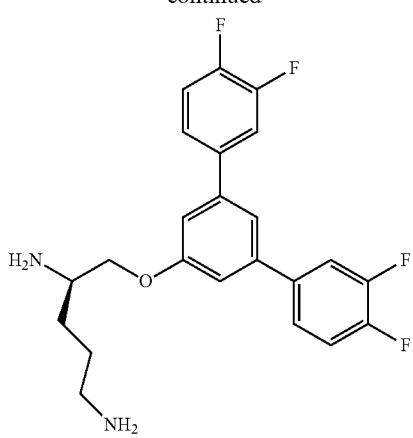
or a salt thereof.
In one embodiment a compound of formula I
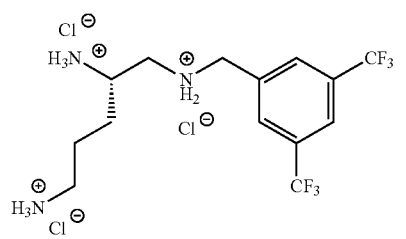
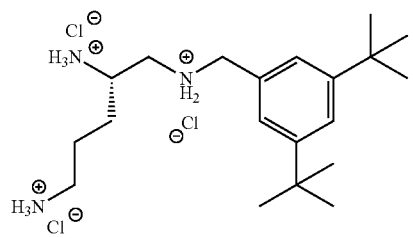
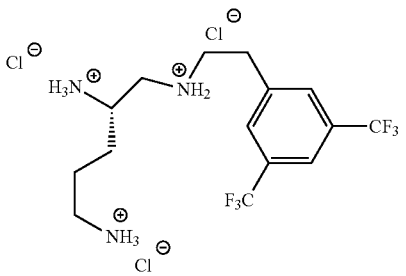
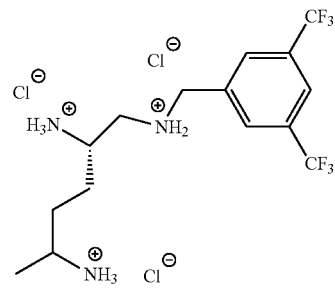
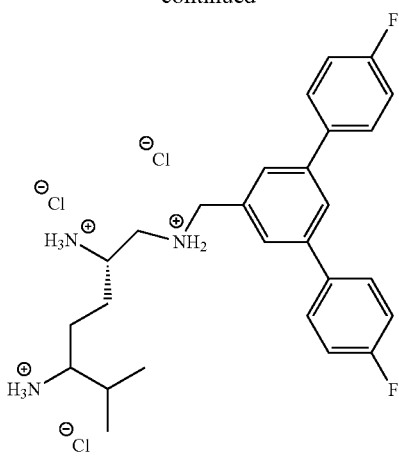

23
-continued
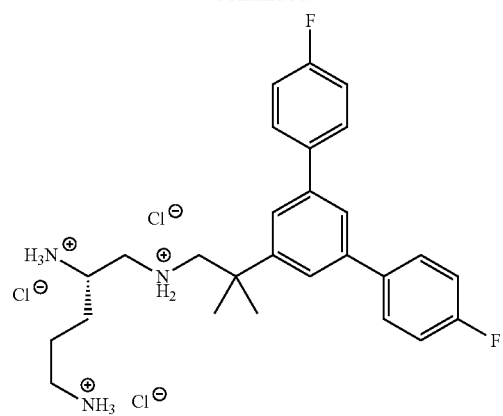
24
-continued
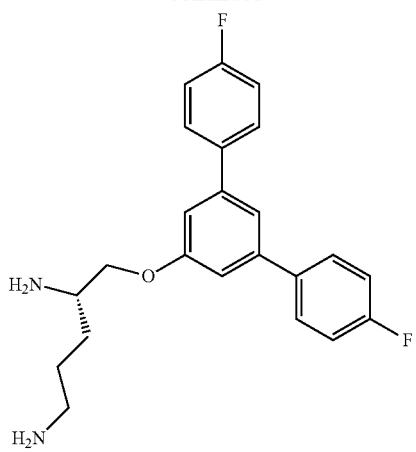
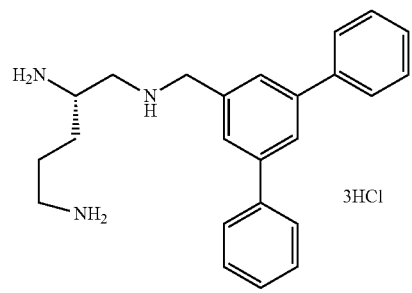
or
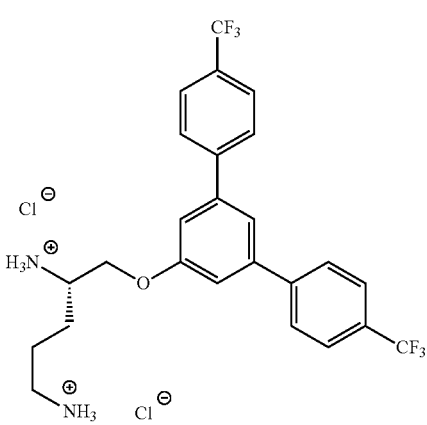

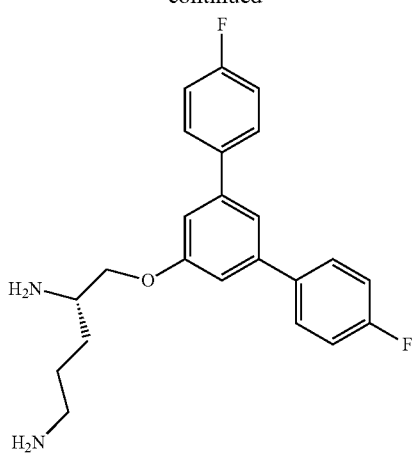
In one embodiment a compound of formula I is:
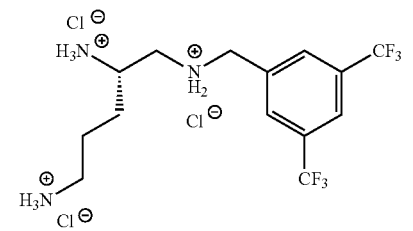
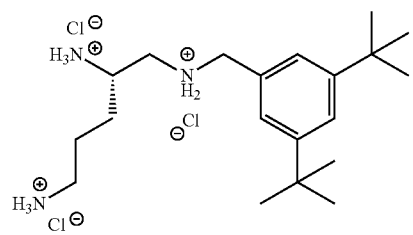
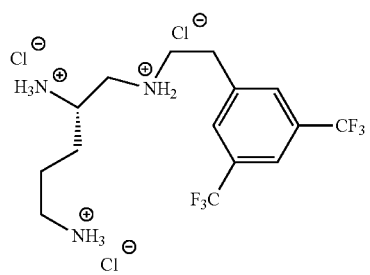
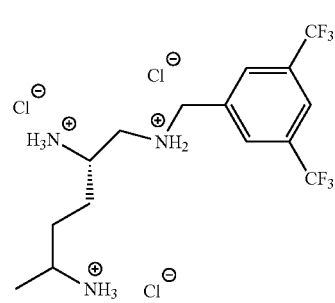
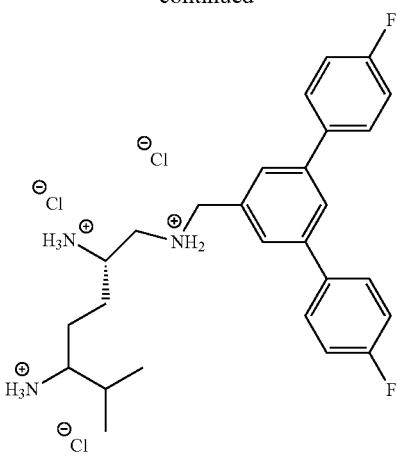
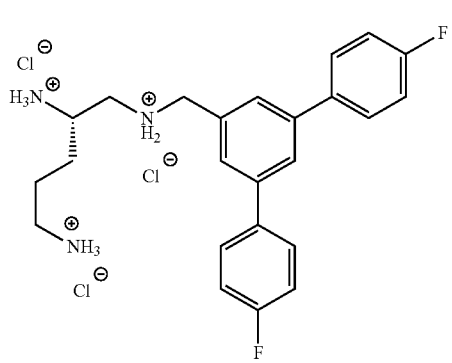
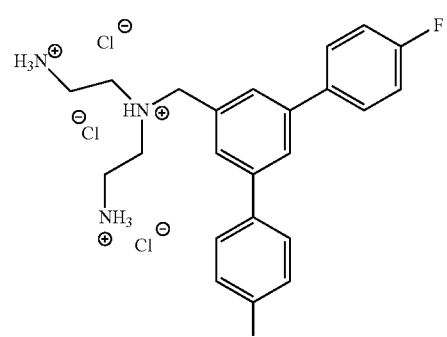
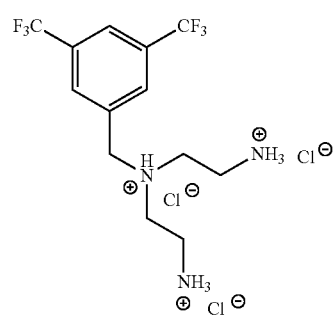

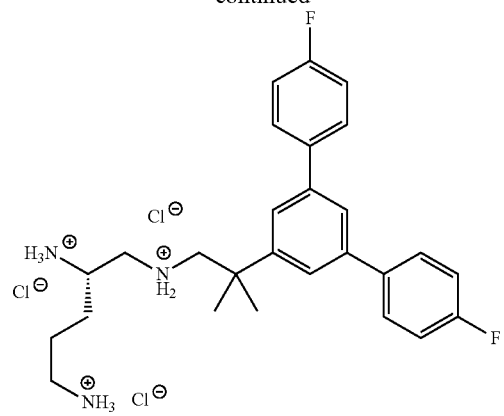
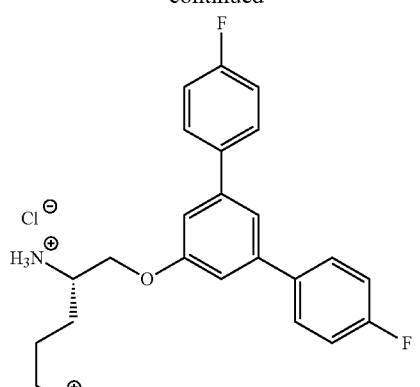
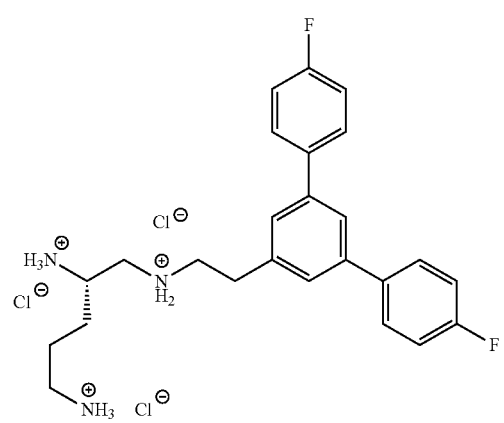
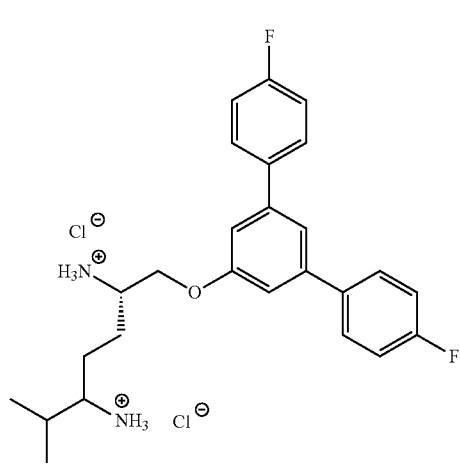
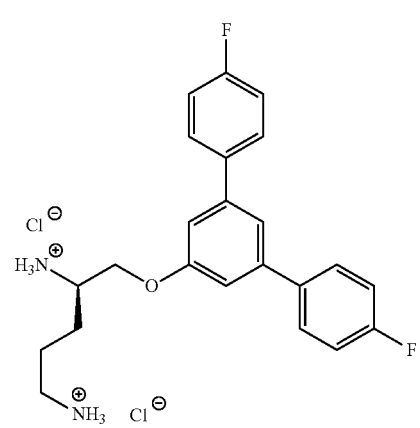
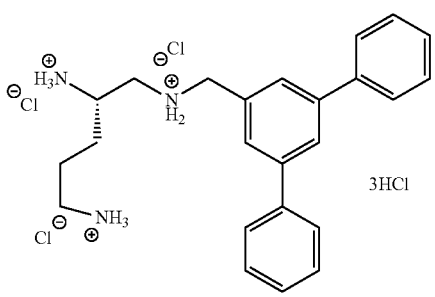
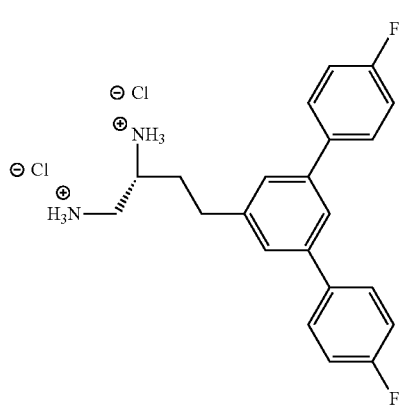
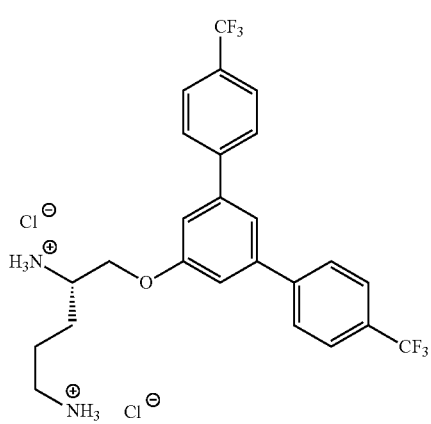

30

Scheme I

General Method for the Synthesis of Compounds of Formula I

There are several methods that could be employed for the preparation of compounds of Formula I. One method that could be used is outlined in Scheme 1 and 2.

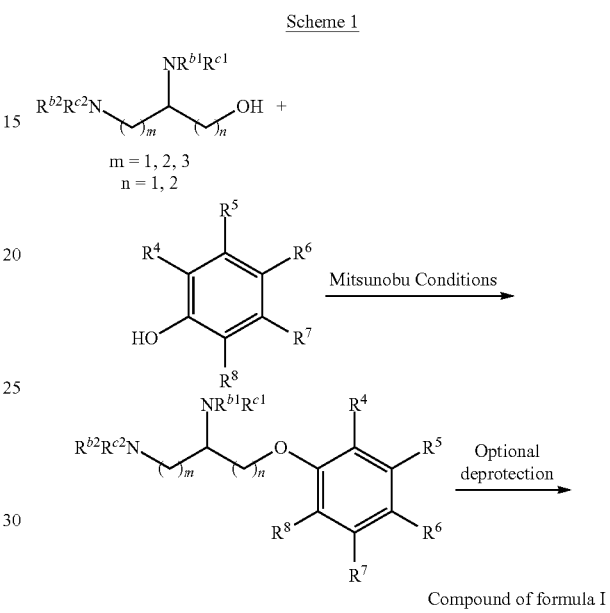

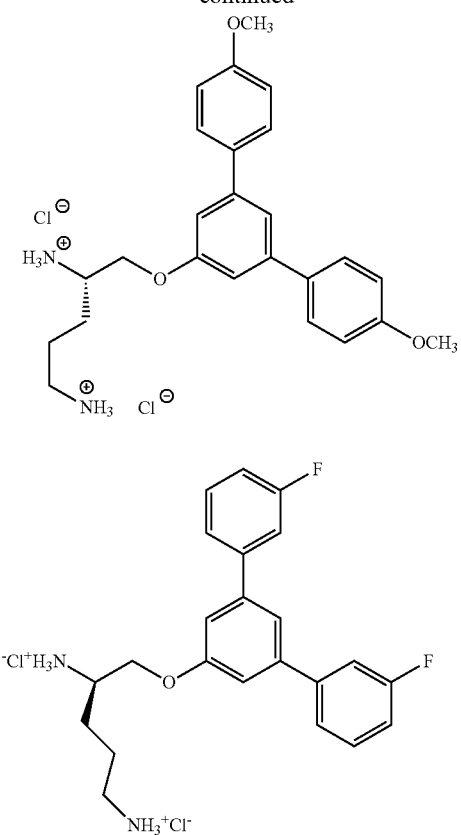

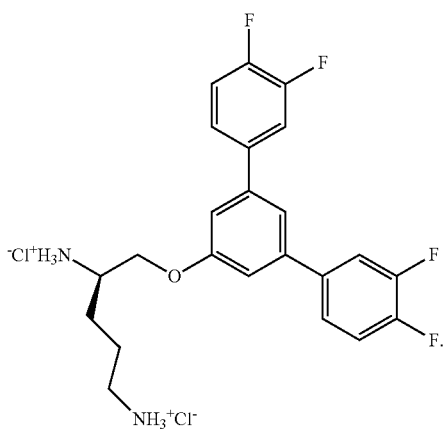

Generally, compounds of formula I as well as synthetic intermediates that can be used for preparing compounds of formula I can be prepared as illustrated in the following General Methods and Schemes. It is understood that variable groups shown below (e.g., $R^1$, $R^2$, $R^3$, $R^4$, $R^5$, $R^6$, $R^7$, $R^8$, n) can represent the final corresponding groups present in a compound of formula I or that these groups can represent groups that can be converted to the final corresponding groups present in a compound of formula I at a convenient point in a synthetic sequence. For example, the variable groups can contain one or more protecting groups that can be removed at a convenient point in a synthetic sequence to provide the final corresponding groups in the compound of formula I.

Using Mitsunobu reaction conditions with the substituents that are appropriately blocked or protected can be used to provide the central pharmacophore that is ether linked. Upon completion of this linkage, the protecting groups, if present, can be removed.

Alternatively, one could condense the appropriate benzoic or acetic acid intermediate an N-protected alkylamine to provide the anticipated carboxamide, as in Schemes 3-5, which can be reduced to provide the amine-linked pharmacophore. Optional removal of the N-protecting groups (if present) would provide compounds of Formula 1.

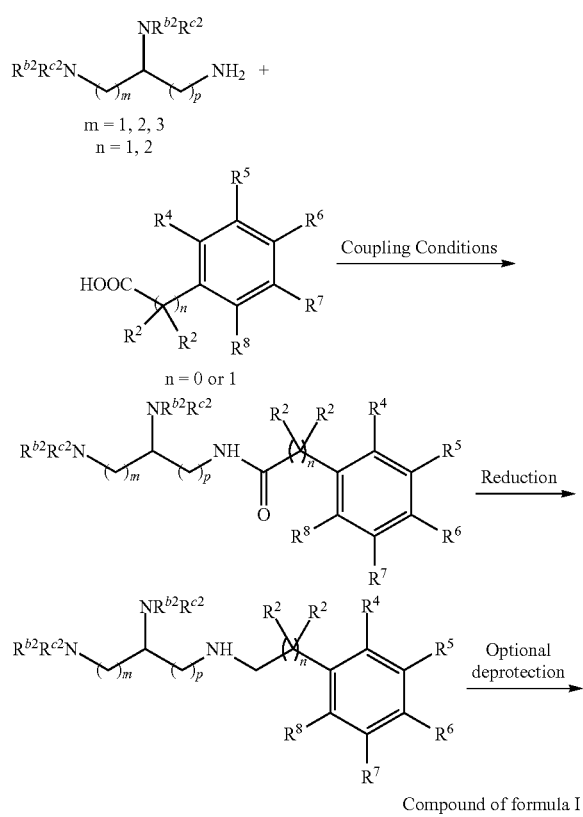

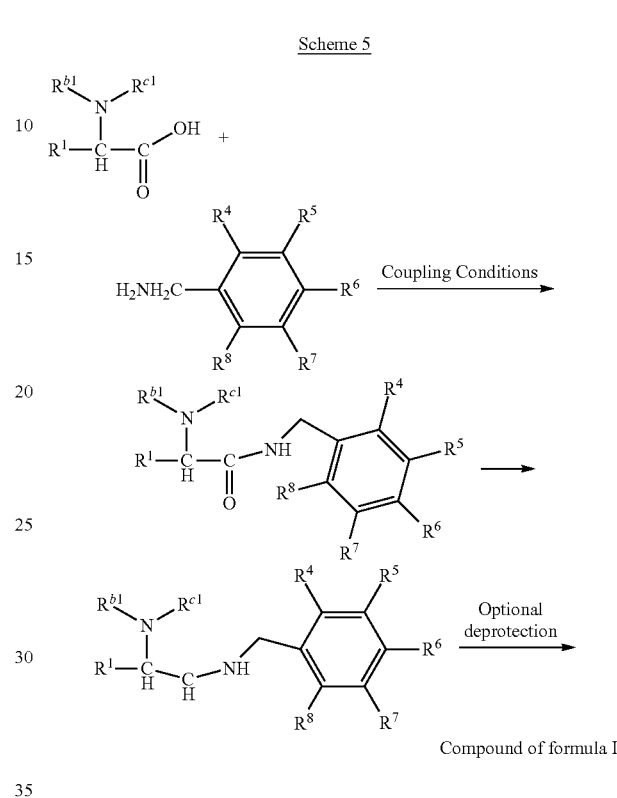

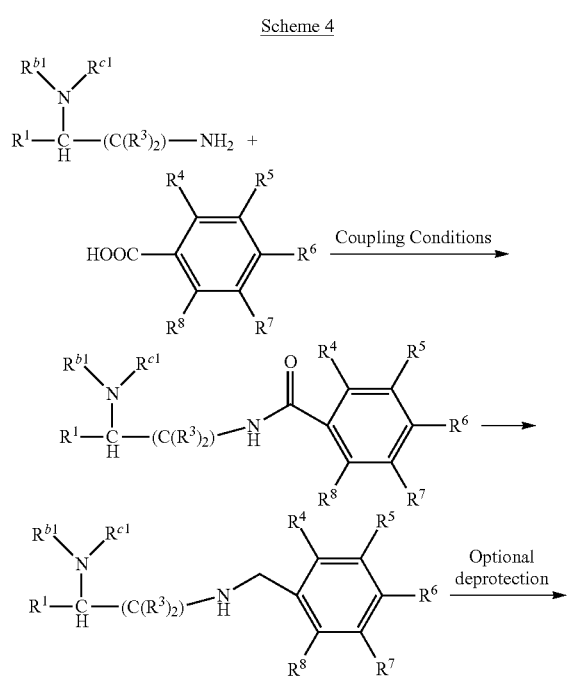

The compounds disclosed herein are bacterial efflux pump inhibitors. An efflux pump inhibitor is a compound that interferes with the ability of an efflux pump to export a substrate. The inhibitor may have intrinsic antibacterial properties of its own. The compounds disclosed herein may be useful for treating bacterial infections (e.g., gram negative and gram positive) when administered with an antibacterial agent.

In one embodiment the bacterial infection being treated is a Gram-negative bacterial strain infection. In one embodiment the Gram-negative bacterial strain is selected from the group consisting of *Acinetobacter baumannii, Acinetobacter calcoaceticus, Acinetobacter haemolyticus, Acinetobacter lwoffi, Actinobacillus actinomycetemcomitans, Aeromonas hydrophilia, Aggregatibacter actinomycetemcomitans, Agrobacterium tumefaciens, Bacteroides distasonis, Bacteroides eggerthii, Bacteroides forsythus, Bacteroides fragilis, Bacteroides ovalus, Bacteroides splanchnicus, Bacteroides thetaiotaomicron, Bacteroides uniformis, Bacteroides vulgatus, Bordetella bronchiseptica, Bordetella parapertussis, Bordetella pertussis, Borrelia burgdorferi, Branhamella catarrhalis, Burkholderia cepacia, Campylobacter coli, Campylobacter fetus, Campylobacter jejuni, Caulobacter crescentus, Chlamydia trachomatis, Citrobacter diversus, Citrobacter freundii, Enterobacter aerogenes, Enterobacter asburiae, Enterobacter cloacae, Enterobacter sakazakii, Escherchia coli, Francisella tularensis, Fusobacterium nucleatum, Gardnerella vaginalis, Haemophilus ducreyi, Haemophilus haemolyticus, Haemophilus influenzae, Haemophilus parahaemolyticus, Haemophilus parainfluenzae, Helicobacter pylori, Kingella denitrificans, Kingella indolo-*

*genes, Kingella kingae, Kingella oralis, Klebsiella oxytoca, Klebsiella pneumoniae, Klebsiella rhinoscleromatis, Legionella pneumophila, Listeria monocytogenes, Moraxella bovis, Moraxella catarrhalis, Moraxella lacunata, Morganella morganii, Neisseria gonorrhoeae, Neisseria meningitidis, Pantoea agglomerans, Pasteurella canis, Pasteurella haemolytica, Pasteurella multocida, Pasteurella tularensis, Porphyromonas gingivalis, Proteus mirabilis, Proteus vulgaris, Providencia alcalifaciens, Providencia rettgeri, Providencia stuartii, Pseudomonas acidovorans, Pseudomonas aeruginosa, Pseudomonas alcaligenes, Pseudomonas fluorescens, Pseudomonas putida, Salmonella enteriditis, Salmonella paratyphi, Salmonella typhi, Salmonella typhimurium, Serratia marcescens, Shigella dysenteriae, Shigella flexneri, Shigella sonnei, Stenotrophomonas maltophilla, Veillonella parvula, Vibrio cholerae, Vibrio parahaemolyticus, Yersinia enterocolitica, Yersinia intermedia, Yersinia pestis* and *Yersinia pseudotuberculosis.*

In one embodiment the bacterial infection being treated is a Gram-positive bacterial strain infection. In one embodiment the Gram-positive bacterial strain is selected from the group consisting of *Actinomyces naeslundii, Actinomyces viscosus, Bacillus anthracis, Bacillus cereus, Bacillus subtilis, Clostridium difficile, Corynebacterium diphtheriae, Corynebacterium ulcerans, Enterococcus faecalis, Enterococcus faecium, Micrococcus luteus, Mycobacterium avium, Mycobacterium intracellulare, Mycobacterium leprae, Mycobacterium tuberculosis, Propionibacterium acnes, Staphylococcus aureus, Staphylococcus epidermidis, Staphylococcus haemolyticus, Staphylococcus hominis, Staphylococcus hyicus, Staphylococcus intermedius, Staphylococcus saccharolyticus, Staphylococcus saprophyticus, Streptococcus agalactiae, Streptococcus mutans, Streptococcus pneumoniae, Streptococcus pyogenes, Streptococcus salivarius* and *Streptococcus sanguis.*

The compositions can, if desired, also contain other active therapeutic agents, such as a narcotic, a non-steroid antiinflammatory drug (NSAID), an analgesic, an anesthetic, a sedative, a local anesthetic, a neuromuscular blocker, an anti-cancer, an antimicrobial (for example, an aminoglycoside, an antifungal, an antiparasitic, an antiviral, a carbapenem, a cephalosporin, a fluoroquinolone, a macrolide, a penicillin, a sulfonamide, a tetracycline, another antimicrobial), an anti-psoriatic, a corticosteriod, an anabolic steroid, a diabetes-related agent, a mineral, a nutritional, a thyroid agent, a vitamin, a calcium-related hormone, an antidiarrheal, an anti-tussive, an anti-emetic, an anti-ulcer, a laxative, an anticoagulant, an erythropoietin (for example, epoetin alpha), a filgrastim (for example, G-CSF, Neupogen), a sargramostim (GM-CSF, Leukine), an immunization, an immunoglobulin, an immunosuppressive (for example, basiliximab, cyclosporine, daclizumab), a growth hormone, a hormone replacement drug, an estrogen receptor modulator, a mydriatic, a cycloplegic, an alkylating agent, an anti-metabolite, a mitotic inhibitor, a radiopharmaceutical, an anti-depressant, an anti-manic agent, an anti-psychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog thereof, dornase alpha (Pulmozyme), a cytokine, or any combination thereof.

In one embodiment the antibacterial agent is selected from quinolones, tetracyclines, glycopeptides, aminoglycosides, β-lactams, rifamycins, macrolides, ketolides, oxazolidinones, coumermycins, and chloramphenicol.

It will be appreciated that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95 the absolute stereoisomer depicted. In another embodiment, the compound may be at least 99% the absolute stereoisomer depicted.

It will also be appreciated by those skilled in the art that certain compounds of the invention can exist in more than one tautomeric form. For example, a substituent of formula —NH—C(═O)H in a compound of formula (I) could exist in tautomeric form as —N═C(OH)H. The present invention encompasses all tautomeric forms of a compound of formula I as well as mixtures thereof that can exist in equilibrium with non-charged and charged entities depending upon pH, which possess the useful properties described herein In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartrate, succinate, fumarate, benzoate, ascorbate, α-ketoglutarate, and α-glycerophosphate. Suitable inorganic salts may also be formed, including hydrochloride, sulfate, nitrate, bicarbonate, and carbonate salts. Salts may be obtained using standard procedures well known in the art, for example by reacting a sufficiently basic compound such as an amine with a suitable acid affording the corresponding anion. Alkali metal (for example, sodium, potassium or lithium) or alkaline earth metal (for example calcium) salts of carboxylic acids can also be made.

Pharmaceutically suitable counterions include pharmaceutically suitable cations and pharmaceutically suitable anions that are well known in the art. Examples of pharmaceutically suitable anions include, but are not limited to those described above (e.g. physiologically acceptable anions) including $Cl^-$, $Br^-$, $I^-$, $CH_3SO_3^-$, $H_2PO_4^-$, $CF_3SO_3^-$, $p\text{-}CH_3C_6H_4SO_3^-$, citrate, tartrate, phosphate, malate, fumarate, formate, or acetate.

It will be appreciated by those skilled in the art that a compound of the invention comprising a counterion can be converted to a compound of the invention comprising a different counterion. Such a conversion can be accomplished using a variety of well-known techniques and materials including but not limited to ion exchange resins, ion exchange chromatography and selective crystallization.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes. For oral administration the compounds can be formulated as a solid dosage form with or without an enteric coating.

Thus, the present compounds may be systemically administered, e.g., orally, in combination with a pharmaceutically acceptable vehicle such as an inert diluent, excipient or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 90% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations, particles, and devices.

The active compound may also be administered intravenously or intramuscularly by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina, nanoparticles, and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 1 to about 500 mg/kg, e.g., from about 5 to about 400 mg/kg of body weight per day, such as 1 to about 250 mg per kilogram body weight of the recipient per day.

The compound is conveniently formulated in unit dosage form; for example, containing 5 to 500 mg, 10 to 400 mg, or 5 to 100 mg of active ingredient per unit dosage form. In one embodiment, the invention provides a composition comprising a compound of the invention formulated in such a unit dosage form.

The desired dose may conveniently be presented in a single dose or as divided doses administered at appropriate intervals, for example, as two, three, four or more sub-doses per day.

The sub-dose itself may be further divided, e.g., into a number of discrete loosely spaced administrations.

Co-administration of a compound disclosed herein with one or more other active therapeutic agents (e.g., antibacterial agents) generally refers to simultaneous or sequential administration of a compound disclosed herein and one or more other active therapeutic agents, such that therapeutically effective amounts of disclosed herein and one or more other active therapeutic agents are both present in the body of the patient.

The ability of a compound disclosed herein to inhibit a bacterial efflux pump can be determined using a method like Test A or Test B as described in Example 20 and as shown in Table 1.

TABLE 1

| Example | STRUCTURE | Enhanced Activity in *E. coli* | Enhanced Activity in *P. aeruginosa* |
|---------|-----------|-------------------------------|--------------------------------------|
| 1 | 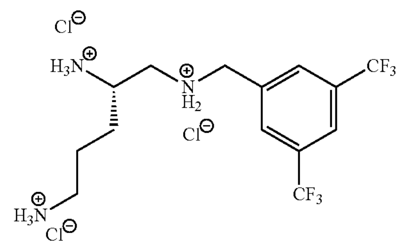 [SMILES: [Cl-] ; [NH3+]CCC[C@H]([NH3+])C[NH2+]Cc1cc(C(F)(F)F)cc(C(F)(F)F)c1 ; [Cl-] ; [Cl-]] | ≥2x | <2x |
| 2 | 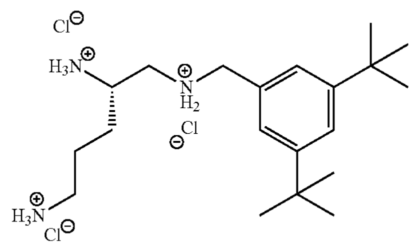 [SMILES: CC(C)(C)c1cc(C[NH2+]C[C@@H]([NH3+])CCC[NH3+])cc(C(C)(C)C)c1 ; [Cl-] ; [Cl-] ; [Cl-]] | ≥8x | <2x |
| 3 | 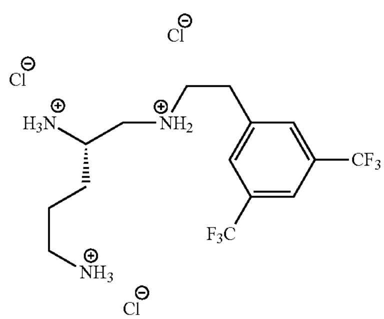 [SMILES: [Cl-] ; [Cl-] ; [NH3+]CCC[C@H]([NH3+])C[NH2+]CCc1cc(C(F)(F)F)cc(C(F)(F)F)c1 ; [Cl-]] | ≥4x | ≥2x |
| 4 | 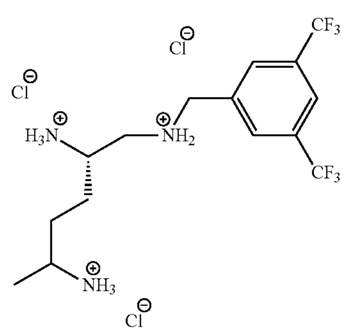 [SMILES: CC([NH3+])CC[C@H]([NH3+])C[NH2+]Cc1cc(C(F)(F)F)cc(C(F)(F)F)c1 ; [Cl-] ; [Cl-] ; [Cl-]] | <2x | <2x |

TABLE 1-continued

| Example | STRUCTURE | Enhanced Activity in E. coli | Enhanced Activity in P. aeruginosa |
|---|---|---|---|
| 5 | (structure) | 32 | ≥2x |
| 6 | (structure) | ≥512x | ≥16x |
| 7 | (structure) | ≥512x | ≥16x |
| 8 | (structure) | <2x | <2x |

TABLE 1-continued
| Example | STRUCTURE | Enhanced Activity in *E. coli* | Enhanced Activity in *P. aeruginosa* |
|---|---|---|---|
| 9 | 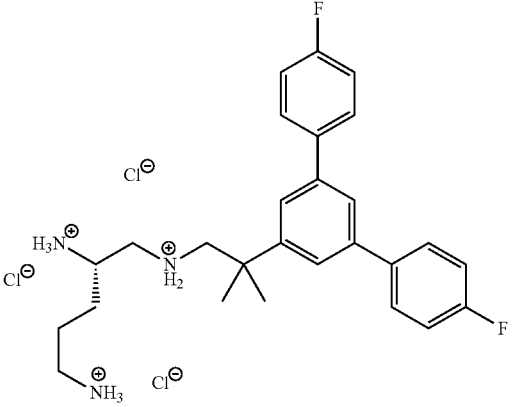 [SMILES: [Cl-] ; CC(C)(C[NH2+]C[C@@H]([NH3+])CCC[NH3+])c1cc(-c2ccc(F)cc2)cc(-c2ccc(F)cc2)c1 ; [Cl-] ; [Cl-]] | ≥128 | ≥2x |
| 10 | 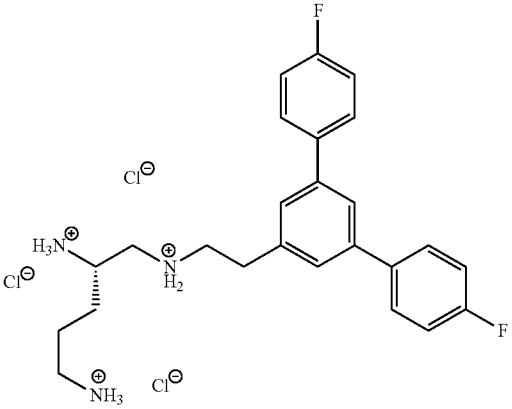 [SMILES: [Cl-] ; [NH3+]CCC[C@H]([NH3+])C[NH2+]CCc1cc(-c2ccc(F)cc2)cc(-c2ccc(F)cc2)c1 ; [Cl-] ; [Cl-]] | ≥1024x | ≥64x |
| 11 | 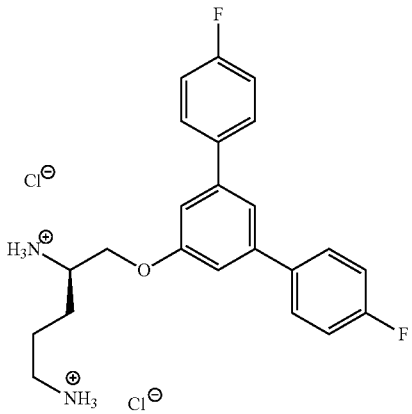 [SMILES: [Cl-] ; [NH3+]CCC[C@H]([NH3+])COc1cc(-c2ccc(F)cc2)cc(-c2ccc(F)cc2)c1 ; [Cl-]] | ≥1024 | ≥16x |

TABLE 1-continued
| Example | STRUCTURE | Enhanced Activity in *E. coli* | Enhanced Activity in *P. aeruginosa* |
|---------|-----------|-------------------------------|--------------------------------------|
| 12 | 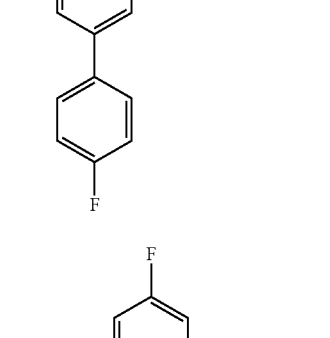 | ≥32x | <2x |
| 13 | 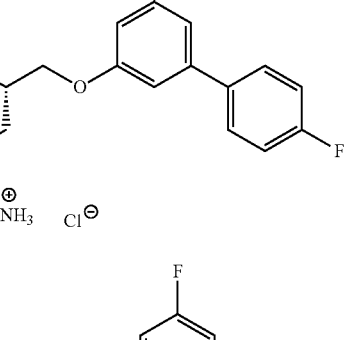 | 256x | <2x |
| 14 | 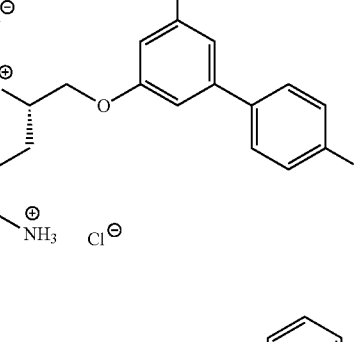 | <2x | <2x |
| 15 | 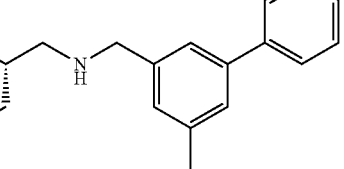 | ≥128x | ≥16x |

TABLE 1-continued

| Example | STRUCTURE | Enhanced Activity in *E. coli* | Enhanced Activity in *P. aeruginosa* |
|---|---|---|---|
| 16 | (structure: bis(4-trifluoromethylphenyl) substituted diamino ether) | <2x | ≥2x |
| 17 | (structure: bis(4-methoxyphenyl) substituted diamino ether) | ≥1024x | ≥2x |
| 18 | (structure: bis(3-fluorophenyl) substituted diamino ether) | ≥512x | ≥1x |

TABLE 1-continued

| Example | STRUCTURE | Enhanced Activity in E. coli | Enhanced Activity in P. aeruginosa |
|---|---|---|---|
| 19 | 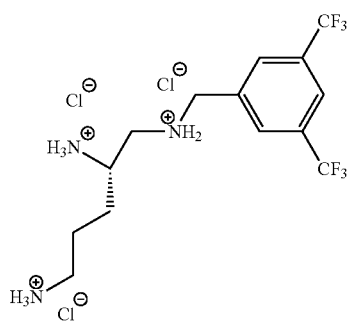 [SMILES: [NH3+]CCC[C@H]([NH3+])C[NH2+]Cc1cc(C(F)(F)F)cc(C(F)(F)F)c1 ; [Cl-] ; [Cl-] ; [Cl-]] | ≥2x | ≥1x |

The invention will now be illustrated by the following non-limiting examples.

Example 1. Preparation of (S)—N¹-(3,5-bis(trifluoromethyl)benzyl)pentane-1,2,5-triaminium Chloride (S)—N¹-(3,5-Bis(trifluoromethyl)benzyl)pentane-1,2,5-triaminium chloride To a solution of (S)-di-tert-butyl (5-((3,5-bis(trifluoromethyl)benzyl)amino)pentane-1,4-diyl)dicarbamate (100 mg, 0.184 mmol) in DCM (4 mL) and MeOH (1 mL) was added 0.4 mL HCl in dioxane. The reaction was stirred at room temperature overnight. The residue was concentrated and triturated with EtOAc and hexanes to afford product (65 mg, 76% yield) as a white solid. $^1$H NMR (300 MHz, CD$_3$OD) δ 8.38 (s, 2H), 8.12 (s, 1H), 4.56 (s, 2H), 3.80-3.50 (m, 4H), 3.05 (m, 4H), 3.05 (m, 2H), 1.91 (m, 4H).

The requisite intermediate was prepared as described in the following paragraph.

Intermediate a

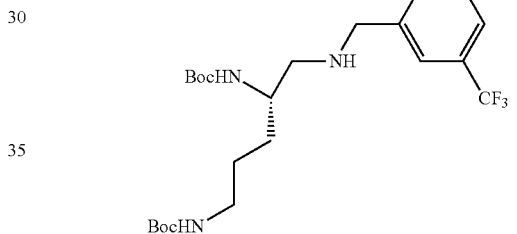

(S)-Di-t-butyl (5-((3,5-bis(trifluoromethyl)benzyl)amino)pentane-1,4-diyl)dicarbamate To a solution of (S)-di-tert-butyl(5-aminopentane-1,4-diyl) dicarbamate (120 mg, 0.378 mmol) and 3,5-bis(trifluoromethyl)benzaldehyde (110 mg, 0.454) in MeOH (10 mL) was added 4 Å molecular sieves and sodium cyanoborohydride (71.3 mg, 1.13 mmol). The reaction was stirred at room temperature overnight. The molecular sieves were filtered off and washed with EtOAc. The filtrate was concentrated and partitioned between EtOAc and sat. NaHCO$_3$ solution, and then extracted with EtOAc (3×10 mL). The organic layers were combined, washed with brine, and concentrated. The residue was purified using an ISCO chromatograph with silica (0-100% ethyl acetate/Hexanes) to give the desired product (102 mg, 48% yield) as a semi-solid. $^1$H NMR (300 MHz, CDCl$_3$) δ 7.82 (s, 2H), 7.70 (s, 1H), 4.65 (bs, 2H), 3.91 (m, 1H), 3.13 (m, 2H), 2.67 (m, 2H), 1.57-1.39 (m, 22H).

Example 2. Preparation of (S)—N¹-(3,5-di-tert-butylbenzyl)pentane-1,2,5-triaminium Chloride

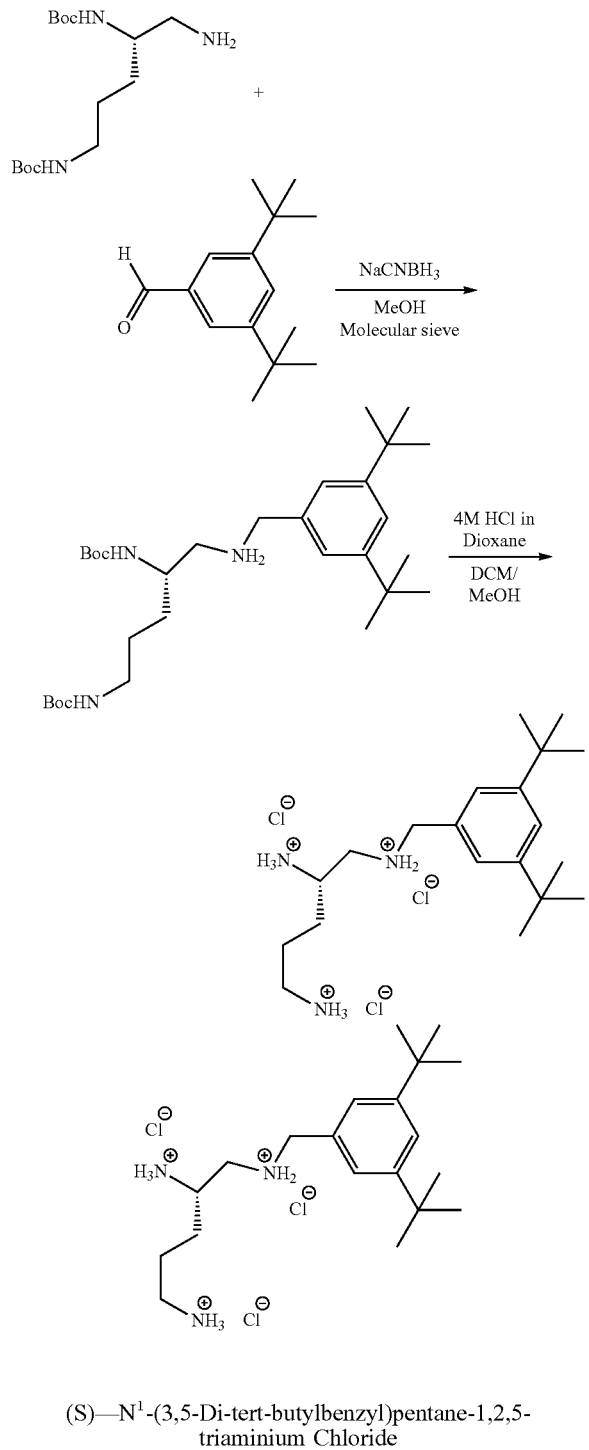

(S)—N¹-(3,5-Di-tert-butylbenzyl)pentane-1,2,5-triaminium Chloride

To a solution of (S)-di-tert-butyl (5-((3,5-bis(trifluoromethyl)benzyl)amino)pentane-1,4-diyl) dicarbamate (120 mg, 0.23 mmol) in DCM (4 mL) and MeOH (1 mL) was added 0.4 mL HCl in dioxane. The reaction was stirred at room temperature overnight. The residue was concentrated and triturated with EtOAc and hexanes to afford product (84 mg, 85% yield) as white solid. ¹H NMR (300 MHz, CD₃OD) δ 7.75 (s, 3H), 4.32 (m, 2H), 3.77 (m, 2H), 3.55-3.42 (m, 2H), 3.04 (m, 2H), 1.80 (m, 4H), 1.38 (s, 18H).

The requisite intermediate was prepared as described in the following paragraph.

Intermediate a

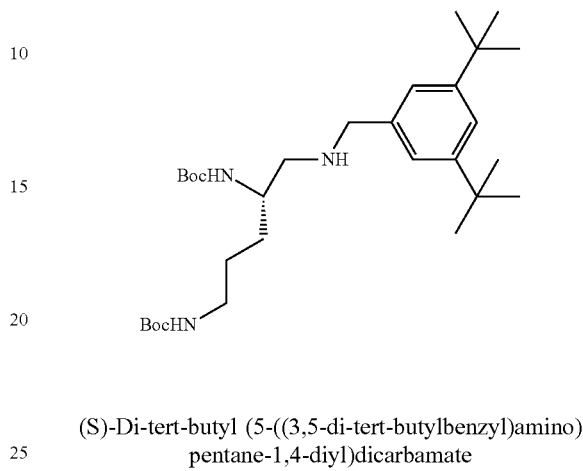

(S)-Di-tert-butyl (5-((3,5-di-tert-butylbenzyl)amino) pentane-1,4-diyl)dicarbamate To a solution of (S)-di-tert-butyl(5-aminopentane-1,4-diyl) dicarbamate (120 mg, 0.378 mmol) and 3,5-di-tert-butylbenzaldehyde (99.1 mg, 0.45 mmol) in MeOH (10 mL) was added 4 Å molecular sieves and sodium cyanoborohydride (71.3 mg, 1.13 mmol). The reaction was stirred at room temperature overnight. The molecular sieves were filtered off and washed with EtOAc. The filtrate was concentrated and partitioned between EtOAc and sat. NaHCO₃ solution, and then extracted with EtOAc (3×10 mL). The organic layers were combined, washed with brine, and concentrated. The residue was purified using an ISCO chromatograph with silica (0-100% ethyl acetate/Hexanes) to give the desired product (130 mg, 66% yield) as a semi-solid. ¹H NMR (300 MHz, CDCl₃) δ 7.38 (s, 1H), 7.20 (s, 2H), 5.07 (bs, 1H), 4.81 (bs, 1H), 3.94-3.79 (m, 3H), 3.13 (m, 2H), 2.82 (m, 2H), 1.54-1.24 (m, 40H).

Example 3. Preparation of (S)—N¹-(3,5-bis(trifluoromethyl)phenethyl)pentane-1,2,5-triaminium chloride

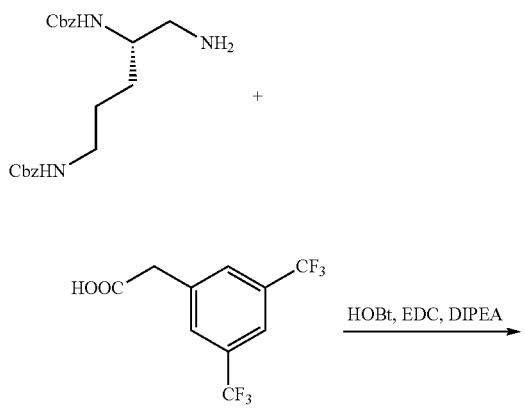

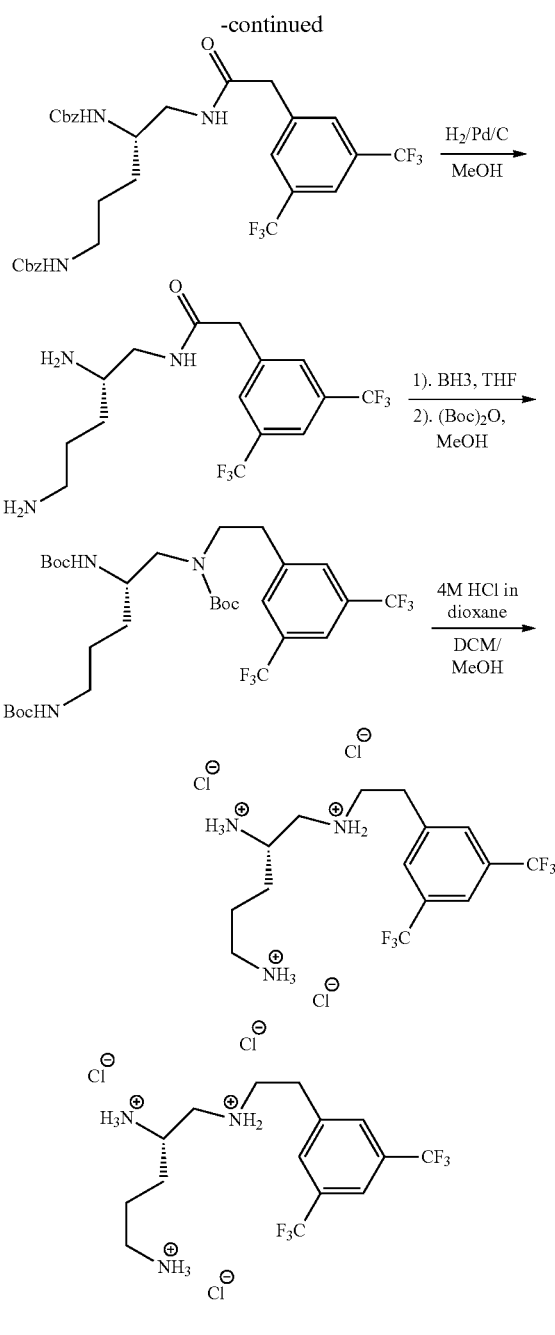

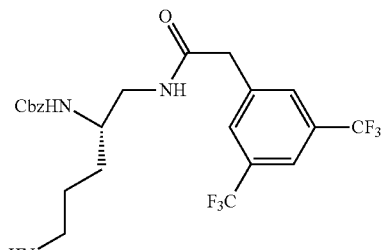

(S)-Dibenzyl (5-(2-(3,5-bis(trifluoromethyl)phenyl)acetamido)pentane-1,4-diyl)dicarbamate To 2-(3,5-bis(trifluoromethyl)phenyl)acetic acid (200 mg, 0.539 mmol) in dry DCM (10 mL) was added DIPEA (0.188 mL, 1.08 mmol), HOBt (43.7 mg, 0.32 mmol), EDC (124 mg, 1.65 mmol). The reaction mixture was stirred at room temperature for 5 minutes. Di-tert-butyl (2S)-[1-amino-6-methylheptane-2,5-diyl]dicarbamate (200 mg, 0.539 mmol) was added and the reaction was allowed to stir overnight at room temperature. The reaction mixture was then diluted with DCM and washed with saturated NaHCO$_3$ and brine. The organic layer was dried over sodium sulfate and filtered. Filtrate was then concentrated and purified using an ISCO chromatograph with silica (0-100% ethyl acetate/hexanes) to give the product (250 mg, 72.5% yield) as a white solid. $^1$H NMR (300 MHz, CDCl$_3$) δ 7.79 (s, 3H), 6.65 (bs, 1H), 3.67 (s, 2H), 3.40 (m, 1H), 3.02 (m, 1H), 2.86 (m, 1H), 2.72 (m, 2H), 1.71 (m, 4H).

Intermediate b

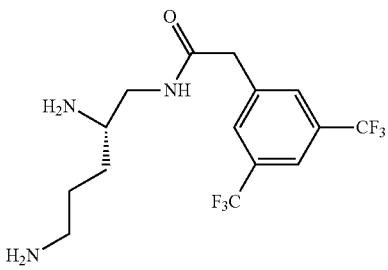 [SMILES: NCCC[C@H](N)CNC(=O)Cc1cc(C(F)(F)F)cc(C(F)(F)F)c1]

(S)-2-(3,5-Bis(trifluoromethyl)phenyl)-N-(2,5-diaminopentyl)acetamide (S)—N$^1$-(3,5-Bis(trifluoromethyl)phenethyl)pentane-1,2,5-triaminium chloride To a solution of (S)-di-tert-butyl (5-((3,5-bis(trifluoromethyl)phenethyl)(tert-butoxycarbonyl)amino)pentane-1,4-diyl)dicarbamate (140 mg, 0.21 mmol) in DCM (4 mL) and MeOH (1 mL) was added 0.5 mL HCl in dioxane. The reaction was stirred at room temperature overnight. The residue was concentrated to afford product (90.5 mg, 91% yield) as a white solid. $^1$H NMR (300 MHz, DMSO-d$_6$) δ 9.78 (bs, 1H), 8.63 (bs, 1H), 8.07-8.02 (m, 3H), 3.68 (m, 2H), 3.38 (m, 4H), 3.38 (m, 4H), 2.84 (m, 3H), 1.74 (m, 4H).

The requisite intermediates were prepared as described in the following paragraphs.

To a solution of (S)-dibenzyl (5-(2-(3,5-bis(trifluoromethyl)phenyl)acetamido)pentane-1,4-diyl)dicarbamate (240 mg, 0.375 mmol) in MeOH (35 mL) was added 50 mg 10% palladium on carbon. The reaction was hydrogenated overnight under hydrogen at room temperature. The reaction was filtered through Celite, washed with MeOH and concentrated to afford the desired product (136 mg, 99% yield) which was used directly in the next step without further purification. $^1$H NMR (300 MHz, CDCl$_3$) δ 7.79 (s, 3H), 6.65 (bs, 1H), 3.67 (s, 2H), 3.40 (m, 1H), 3.02 (m, 1H), 2.86 (m, 1H), 2.72 (m, 2H), 1.71 (m, 4H).

Intermediate c

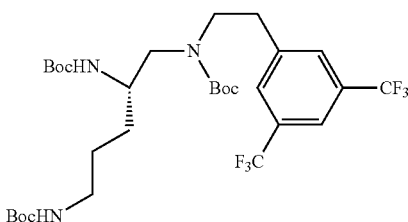 [SMILES: CC(C)(C)OC(=O)NCCC[C@@H](CN(CCc1cc(C(F)(F)F)cc(C(F)(F)F)c1)C(=O)OC(C)(C)C)NC(=O)OC(C)(C)C]

(S)-Di-t-butyl (5-((3,5-bis(trifluoromethyl)phenethyl)(t-butoxycarbonyl)amino)pentane-1,4-diyl) dicarbamate To a solution of (S)-2-(3,5-bis(trifluoromethyl)phenyl)-N-(2,5-diaminopentyl) acetamide in THF (20 mL) was added 1.0 M BH$_3$ in THF (2 mL) and the resulting mixture was refluxed overnight. After the reaction cooled down to room temperature, it was quenched with 2 mL MeOH and 0.5 mL water. The reaction mixture was refluxed again for 1 hour. The reaction mixture was concentrated. To the residue was added 10 mL MeOH and 200 mg (Boc)$_2$O. This mixture was then allowed to stir at room temperature for 2 hours. The reaction mixture was concentrated and to the residue was added EtOAc. The ethyl acetate solution was washed with saturated NaHCO$_3$ and brine. The organic layer was dried over sodium sulfate and filtered. Filtrate was then concentrated and purified using an ISCO chromatograph with silica (0-70% ethyl acetate/hexanes) to give the desired product (153 mg, 61.7% yield) as a white solid.

Example 4. Preparation of (2S)—N$^1$-(3,5-bis(trifluoromethyl)benzyl)hexane-1,2,5-triaminium Chloride

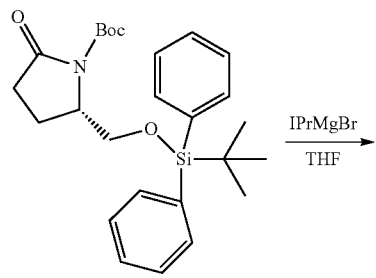

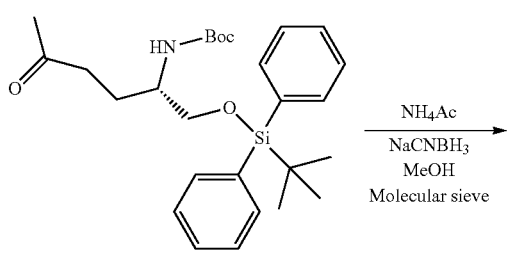

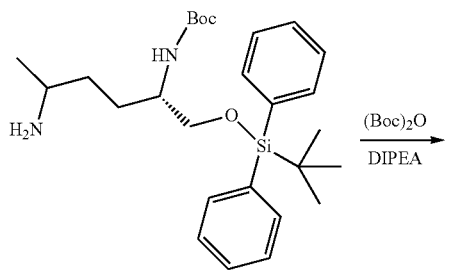

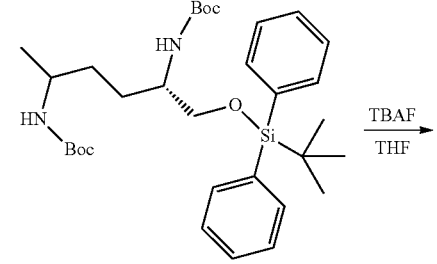

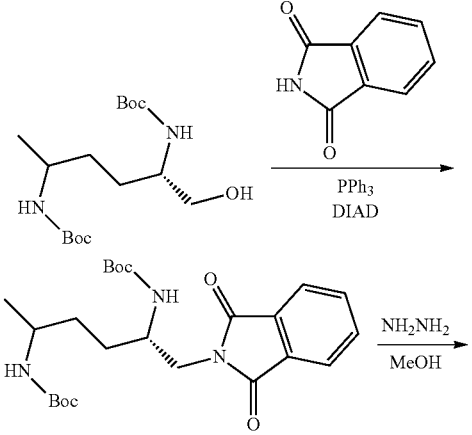

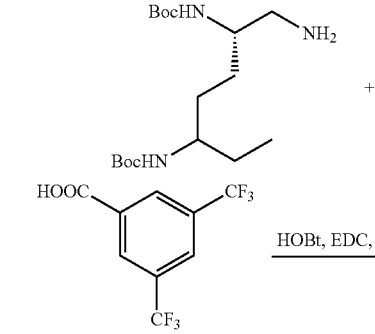

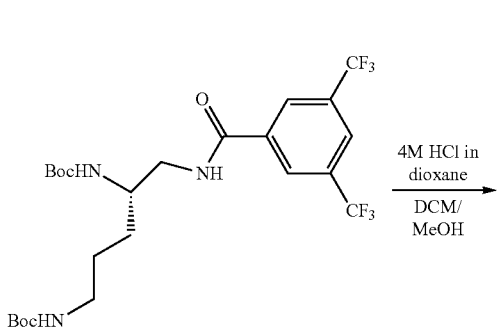

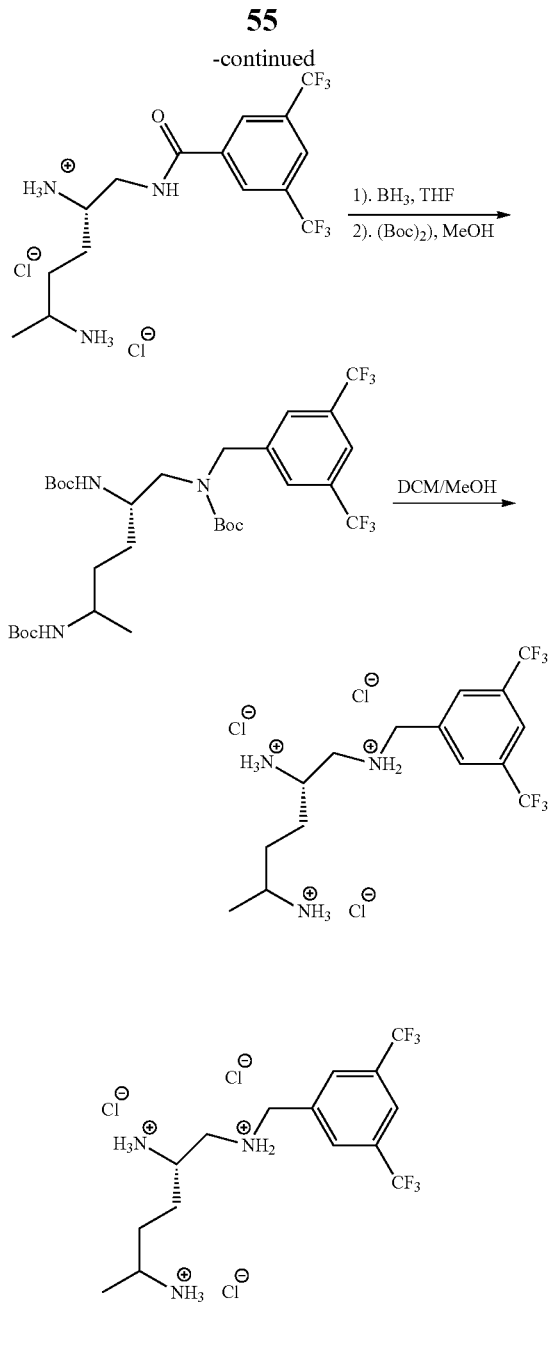

(2S)—N-(3,5-Bis(trifluoromethyl)benzyl)hexane-1,2,5-triaminium chloride

To a solution of di-tert-butyl ((2S)-1-((3,5-bis(trifluoromethyl)benzyl)(tert-butoxycarbonyl)amino)hexane-2,5-diyl)dicarbamate (75 mg, 0.16 mmol) in DCM (5 mL) and MeOH (1 mL) was added 0.4 mL HCl in dioxane. The reaction mixture was stirred at room temperature overnight. The residue was concentrated and triturated with EtOAc and hexanes to afford product (51 mg, 95% yield) as white solid. $^1$H NMR (300 MHz, DMSO-$d_6$) δ 10.28 (bs, 2H), 8.67 (bs, 2H), 8.47 (s, 2H), 8.30 (s, 1H), 8.15 (m, 2H), 4.50 (m, 2H), 3.72 (m, 2H), 3.50 (m, 2H), 1.84-1.67 (m, 4H).

The requisite intermediates were prepared as described in the following paragraphs.

Intermediate a

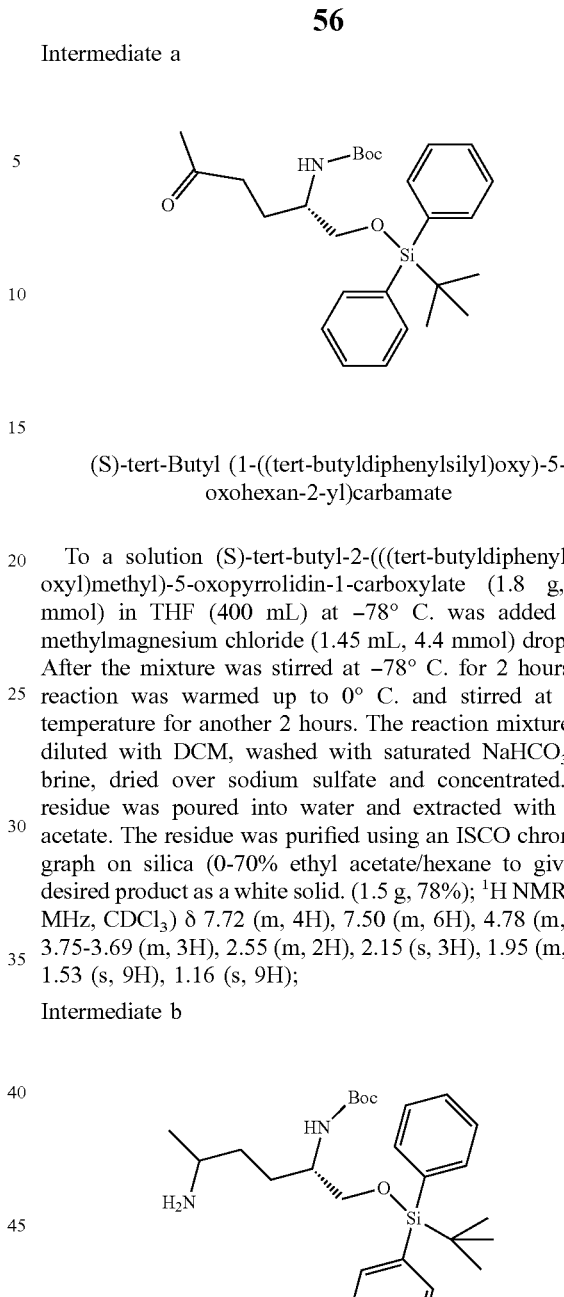

(S)-tert-Butyl (1-((tert-butyldiphenylsilyl)oxy)-5-oxohexan-2-yl)carbamate

To a solution (S)-tert-butyl-2-(((tert-butyldiphenylsilyl)oxy)methyl)-5-oxopyrrolidin-1-carboxylate (1.8 g, 4.0 mmol) in THF (400 mL) at −78° C. was added 3 M methylmagnesium chloride (1.45 mL, 4.4 mmol) dropwise. After the mixture was stirred at −78° C. for 2 hours, the reaction was warmed up to 0° C. and stirred at room temperature for another 2 hours. The reaction mixture was diluted with DCM, washed with saturated NaHCO$_3$ and brine, dried over sodium sulfate and concentrated. The residue was poured into water and extracted with ethyl acetate. The residue was purified using an ISCO chromatograph on silica (0-70% ethyl acetate/hexane to give the desired product as a white solid. (1.5 g, 78%); $^1$H NMR (300 MHz, CDCl$_3$) δ 7.72 (m, 4H), 7.50 (m, 6H), 4.78 (m, 1H), 3.75-3.69 (m, 3H), 2.55 (m, 2H), 2.15 (s, 3H), 1.95 (m, 2H), 1.53 (s, 9H), 1.16 (s, 9H);

Intermediate b tert-Butyl ((2S)-5-amino-1-((tert-butyldiphenylsilyl)oxy)hexan-2-yl)carbamate To a solution (S)-tert-butyl (1-((tert-butyldiphenylsilyl)oxy)-5-oxohexan-2-yl)carbamate (0.70 mg, 9.0 mmol) and ammonium acetate (2.01 g, 26 mmol) in MeOH (100 mL) was added 4 Å molecular sieves and sodium cyanoborohydride (1.64 g, 26 mmol). The reaction mixture was stirred at room temperature overnight. The molecular sieves were filtered off and washed with EtOAc. The filtrate was concentrated and partitioned between EtOAc and sat. NaHCO$_3$ solution. The combined organic layers were washed with brine, dried and concentrated. The crude product was used directly in the next step without further purification.

Intermediate c

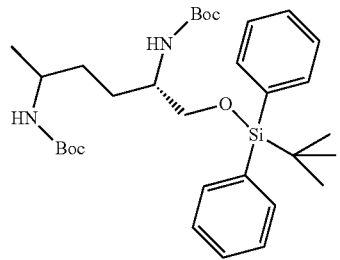 [SMILES: CC(CC[C@@H](CO[Si](c1ccccc1)(c1ccccc1)C(C)(C)C)NC(=O)OC(C)(C)C)NC(=O)OC(C)(C)C]

Di-tert-butyl ((2S)-1-((tert-butyldiphenylsilyl)oxy)hexane-2,5-diyl)dicarbamate

To a solution tert-butyl ((2S)-5-amino-1-((t-butyldiphenylsilyl)oxy)hexan-2-yl)carbamate (0.65 g, 1.34 mmol) in DCM (25 mL) at room temperature was added DIPEA (0.47 mL, 2.68 mmol) and (Boc)$_2$O (0.584 g, 2.68 mmol). The reaction mixture was stirred at room temperature overnight. The reaction mixture was diluted with DCM, washed with saturated NaHCO$_3$ and brine, dried over sodium sulfate and concentrated. The residue was purified using an ISCO chromatograph on silica (0-100% ethyl acetate/hexane) to give the desired product as a white solid. (586 mg, 75%); $^1$H NMR (300 MHz, CDCl$_3$) δ 7.74 (m, 5H), 7.50 (m, 5H), 4.78 (m, 1H), 4.40 (m. 1H), 3.69 (m, 5H), 1.54-1.33 (m, 31H), 1.12 (m, 3H);

Intermediate d

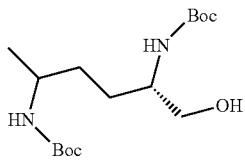 [SMILES: CC(CC[C@@H](CO)NC(=O)OC(C)(C)C)NC(=O)OC(C)(C)C]

Di-tert-butyl ((2S)-1-hydroxyhexane-2,5-diyl)dicarbamate

To a solution di-tert-butyl ((2S)-1-((t-butyldiphenylsilyl)oxy)hexane-2,5-diyl)dicarbamate (0.50 g, 0.86 mmol) in THF (15 mL) at 0° C. was added 1 M TBAF (3.43 mL, 3.43 mmol). The reaction was stirred at room temperature overnight. The reaction mixture was quenched with saturated ammonium chloride, extracted with EtOAc (3×10 mL). The organic layers were combined, washed with brine, dried over sodium sulfate and concentrated. The residue was purified using an ISCO chromatograph on silica (0-70% ethyl acetate/hexane) to give the desired product as a white solid. (290 mg, 97%). $^1$H NMR (300 MHz, CDCl$_3$) δ 4.96-4.86 (m, 1H), 4.55-4.36 (m. 1H), 3.57 (m, 3H), 3.13 (m, 1H), 1.61-1.22 (m, 22H), 1.08 (m, 3H).

Intermediate e

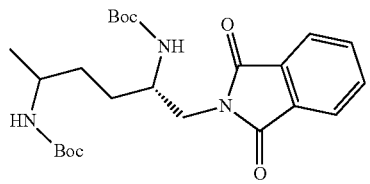 [SMILES: CC(CC[C@@H](CN1C(=O)c2ccccc2C1=O)NC(=O)OC(C)(C)C)NC(=O)OC(C)(C)C]

Di-tert-butyl ((2S)-1-(1,3-dioxoisoindolin-2-yl)hexane-2,5-diyl)dicarbamate

Triphenylphosphine (237 mg, 0.91 mmol) and phthalimide (133 mg, 0.91 mmol) were added to a flask containing dry THF (50 mL). Di-tert-butyl ((2S)-1-hydroxyhexane-2,5-diyl)dicarbamate (250 mg, 0.75 mmol) was added and the flask was cooled to 0° C. DIAD (183 mg, 0.91 mmol) was added dropwise and reaction allowed to stir for 30 minutes at 0° C. and then overnight at room temperature. The mixture was concentrated under reduced pressure and the residue purified using an ISCO chromatograph on silica (0-70% ethyl acetate/hexane) to give the desired product (320 mg) as a white solid. $^1$H NMR (300 MHz, CDCl$_3$) δ 7.82 (m, 2H), 7.69 (m, 2H), 4.70-4.58 (m, 1H), 4.37 (m. 1H), 3.92 (m, 1H), 3.65 (m, 3H), 1.61-1.11 (m, 26H).

Intermediate f

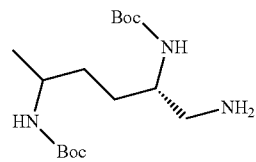 [SMILES: CC(CC[C@@H](CN)NC(=O)OC(C)(C)C)NC(=O)OC(C)(C)C]

Di-tert-butyl ((2S)-1-aminohexane-2,5-diyl)dicarbamate

The di-tert-butyl ((2S)-1-(1,3-dioxoisoindolin-2-yl)hexane-2,5-diyl)dicarbamate (320 mg, 0.694 mmol) was dissolved in methanol (20 mL) and hydrazine monohydrate (0.14 mL, 2.78 mmol) was added. The reaction mixture was then refluxed for 2 hours and cooled to room temperature. The precipitate formed was filtered and methanol was used to wash the filtrate. The filtrate was concentrated under reduced pressure. The reaction mixture was diluted with EtOAc, sequentially washed with saturated NaHCO$_3$, saturated ammonium chloride and brine. The organic layer was dried over sodium sulfate and concentrated. The crude product was used directly without further purification; 1H NMR (300 MHz, CDCl$_3$) δ 4.98-4.90 (m, 1H), 4.72-4.41 (m. 1H), 3.59-3.48 (m, 1H), 2.75-2.56 (m, 1H), 1.48-1.021 (m, 25H).

Intermediate g

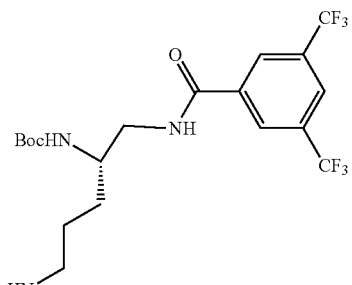

(S)-Di-tert-butyl (5-(3,5-bis(trifluoromethyl)benzamido)pentane-1,4-diyl)dicarbamate To 2-(3,5-bis(trifluoromethyl)phenyl)acetic acid (103 mg, 0.4 mmol) in dry DCM (5 mL) was added DIPEA (0.13 mL, 0.72 mmol), HOBt (29.3 mg, 0.22 mmol), EDC (83.2 mg, 0.43 mmol). The reaction mixture was stirred at room temperature for 5 minutes. di-tert-butyl ((2S)-1-amino-hexane-2,5-diyl)dicarbamate (120 mg, 0.36 mmol) was added and the reaction was continued to stir at room temperature overnight. The reaction mixture was then diluted with DCM and washed with saturated NaHCO$_3$ and brine. The organic layer was dried over sodium sulfate and filtered. Filtrate was then concentrated and purified using an ISCO chromatograph on silica (0-50% ethyl acetate/hexanes) to give the product (170 mg, 82% yield) as a white solid. $^1$H NMR (300 MHz, CDCl$_3$) δ 8.26 (s, 1H), 8.03 (m, 1H), 7.90 (m, 1H), 4.25 (m, 1H), 3.65-3.28 (m, 3H), 1.60-1.10 (m, 25H).

Intermediate h

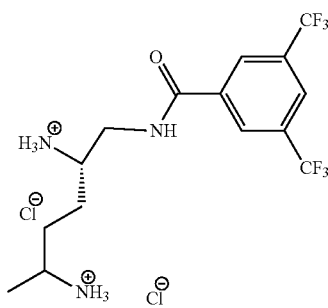 [SMILES: CC([NH3+])CC[C@H]([NH3+])CNC(=O)c1cc(C(F)(F)F)cc(C(F)(F)F)c1 ; [Cl-] ; [Cl-]]

(2S)-1-(3,5-Bis(trifluoromethyl)benzamido)hexane-2,5-diaminium chloride

To a solution of (S)-di-tert-butyl (5-(3,5-bis(trifluoromethyl)benzamido)pentane-1,4-diyl)dicarbamate (170 mg, 0.297 mmol) in DCM (5 mL) and MeOH (1 mL) was added 1 mL HCl in dioxane. The reaction mixture was stirred at room temperature overnight. The residue was concentrated and triturated with EtOAc and hexanes to afford the desired product (110 mg, 93% yield) as white solid. $^1$H NMR (300 MHz, CD$_3$OD) δ 8.69 (m, 2H), 8.37 (m, 1H), 3.88 (m, 3H), 3.68 (m, 1H), 1.93 (m, 4H), 1.51 (m, 3H).

Intermediate i

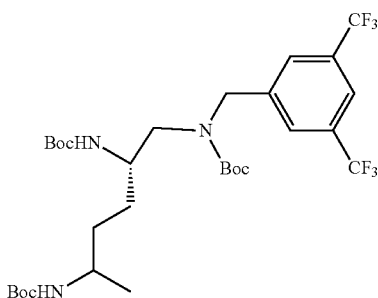 [SMILES: CC(CC[C@@H](CN(Cc1cc(C(F)(F)F)cc(C(F)(F)F)c1)C(=O)OC(C)(C)C)NC(=O)OC(C)(C)C)NC(=O)OC(C)(C)C]

Di-tert-butyl ((2S)— 1-((3,5-bis(trifluoromethyl) benzyl)(tert-butoxycarbonyl)amino)hexane-2,5-diyl) dicarbamate To the solution (2S)-1-(3,5-bis(trifluoromethyl)ben-zamido)hexane-2,5-diaminium chloride (90 mg, 0.20 mmol) in THF (10 mL) was added 1.0 M BH$_3$-THF (2 mL) and the reaction mixture was refluxed overnight. After the reaction was allowed to cooled to room temperature, it was quenched with 2 mL MeOH and 0.5 mL water. The resulting mixture was then refluxed for 1 hour. The reaction mixture was concentrated and to the residue was added 10 mL MeOH and 200 mg (Boc)$_2$O. The reaction mixture was then stirred at room temperature for 2 hours. The reaction mixture was concentrated, diluted with EtOAc, and then washed with saturated NaHCO$_3$ and brine. The organic layer was dried over sodium sulfate and filtered. Filtrate was then concentrated and purified using an ISCO chromatograph with silica (0-80% ethyl acetate/hexanes) to give the product (80 mg, 60% yield) as a white solid. $^1$H NMR (300 MHz, CDCl$_3$) δ 7.79 (s, 1H), 7.71 (m, 2H), 4.65 (bs, 2H), 4.20 (m, 2H), 3.30 (m, 2H), 3.13 (m, 2H), 1.57-1.22 (m, 31H), 1.12 (d, 3H).

Example 5. Preparation of (2S)—N$^1$-((4,4"-difluoro-[1,1':3',1"-terphenyl]-5'-yl)methyl)-6-methyl-heptane-1,2,5-triaminium chloride

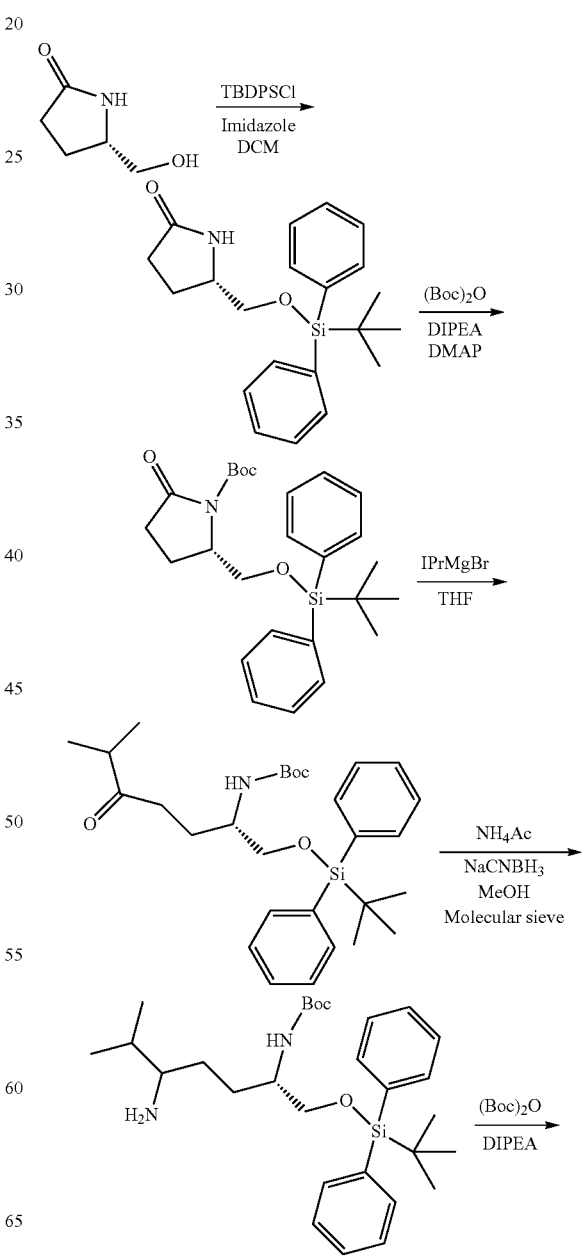

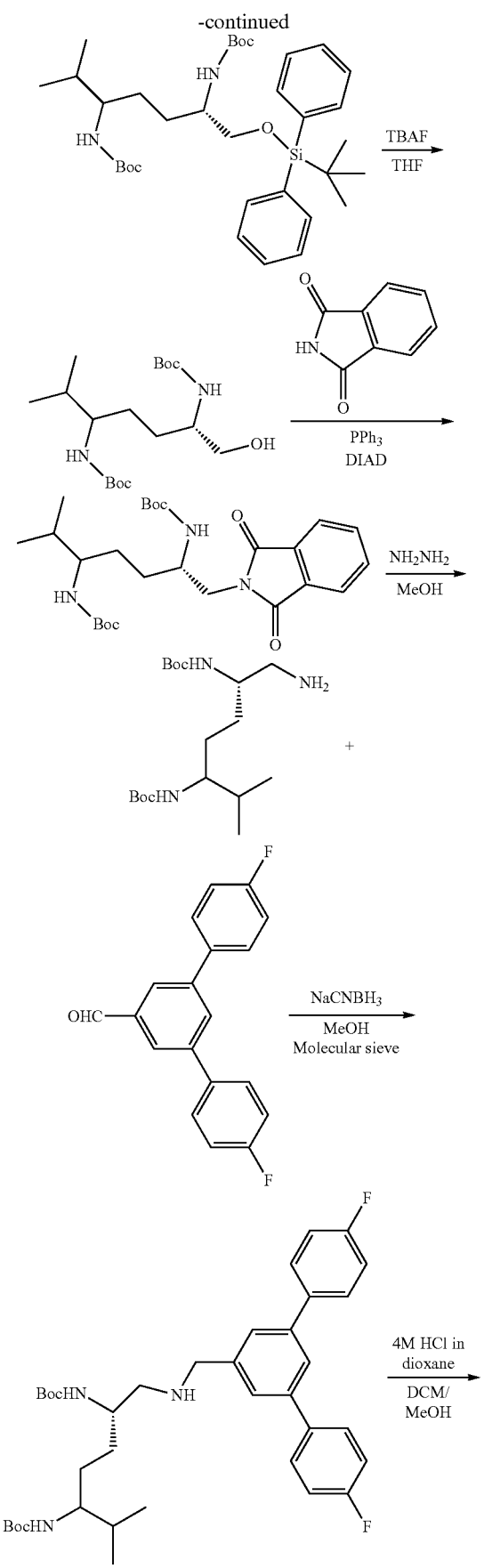

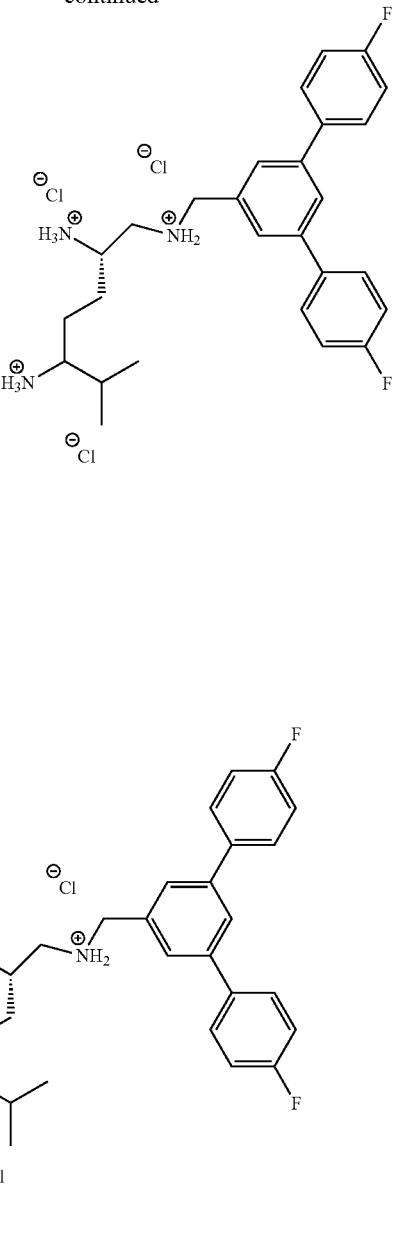

(2S)—N¹-((4,4''-Difluoro-[1,1':3',1''-terphenyl]-5'-yl)methyl)-6-methylheptane-1,2,5-triaminium chloride To a solution of di-tert-butyl ((2S)-1-(((4,4'-difluoro[1,1': 3',1''-terpehnyl]-5'-yl)methyl)amino)-6-methylheptane-2,5-diyl)dicarbamate (100 mg, 0.16 mmol) in DCM (5 mL) and MeOH (1 mL) was added 0.4 mL of 4 N HCl in dioxane. The reaction mixture was stirred at room temperature overnight. The residue was concentrated and then triturated with EtOAc and hexanes to afford product (80 mg, 95% yield) as white solid. ¹H NMR (300 MHz, DMSO-$d_6$) 10.14 (bs, 1H), 8.66 (bs, 2H), 7.96-7.90 (m, 5H), 7.38-7.33 (m, 3H), 4.35 (m, 1H), 3.72 (m, 2H), 3.02 (m, 1H), 1.93-1.73 (m, 4H), 0.94 (m, 6H).

The requisite intermediates were prepared as described in the following paragraphs.

Intermediate a

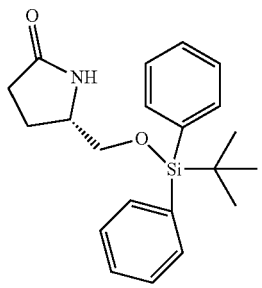 [SMILES: CC(C)(C)[Si](OC[C@@H]1CCC(=O)N1)(c1ccccc1)c1ccccc1]

(S)-5-(((tert-butyldiphenylsilyl)oxyl)methyl)pyrrolidin-2-one

To a solution of (S)-5-(hydroxymethyl)pyrrolidin-2-one (5.0 g, 43.5 mmol) in DCM (100 mL) at 0° C. was added imidazole (4.44 g, 65.2 mmol) and tert-butylchlorodiphenylsiane (13.2 g, 47.8 mmol). The reaction was stirred at 0° C. for 30 min, then allowed to warm to room temperature and then stirred at room temperature overnight. The reaction was diluted with DCM, sequentially washed with saturated NaHCO$_3$, saturated ammonium chloride and brine. The organic layer was dried over sodium sulfate and concentrated. The crude product (15.4 g, yield: 100%) was used in the next step directly without further purification.

Intermediate b

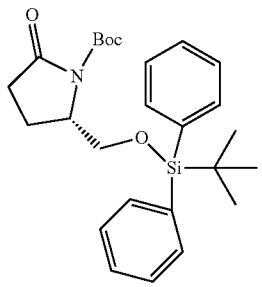 [SMILES: CC(C)(C)OC(=O)N1C(=O)CC[C@H]1CO[Si](c1ccccc1)(c1ccccc1)C(C)(C)C]

(S)-tert-Butyl 2-(((tert-butyldiphenylsilyl)oxy)methyl)-5-oxopyrrolidine-1-carboxylate To a solution (S)-5-(((tert-butyldiphenylsilyl)oxyl)methyl)pyrrolidin-2-one (15.4 g, 43.5 mmol) in DCM (150 mL) at 0° C. was added DIPEA (15.2 mL, 87 mmol), 4-dimethylaminopyridine (0.532 g, 4.35 mmol) and (Boc)$_2$O (19.0 g, 87 mmol). After the mixture was stirred at 0° C. for 30 minute, the reaction was allowed to warm to room temperature and then stirred at room temperature overnight. The reaction mixture was diluted with DCM, washed with saturated NaHCO$_3$ and brine, dried over sodium sulfate and concentrated. The residue was purified using an ISCO chromatograph using silica (0-50% ethyl acetate/hexane) to give product as a white solid. (5.5 g, 84%); $^1$H NMR (300 MHz, CDCl$_3$) δ 7.55-7.52 (m, 4H), 7.37-7.19 (m, 6H), 4.15 (m, 1H), 3.81 (m, 1H), 3.63 (m, 1H), 2.72 (m, 1H), 2.37 (m, 1H), 2.05 (m, 2H), 1.36 (s, 9H), 0.97 (s, 9H);

Intermediate c (S)-tert-Butyl (1-((tert-butyldiphenylsilyl)oxy)-6-methyl-5-oxoheptan-2-yl)carbamate To a solution of (S)-tert-butyl 2-(((tert-butyldiphenylsilyl)oxy)methyl)-5-oxopyrrolidine-1-carboxylate (5.0 g, 11.0 mmol) in THF (150 mL) at −78° C. was added dropwise 1 M isopropylmagnesium chloride (13.2 mL, 13.2 mmol). After the mixture was stirred at −78° C. for 2 hours, the reaction was allowed to warm to 0° C. and then stirred at room temperature for another 2 hours. The reaction mixture was quenched with saturated ammonium chloride solution, and extracted with EtOAc (3×10 mL). The organic layers were combined, washed with brine, dried over sodium sulfate and concentrated. The residue was purified using an ISCO chromatograph on silica (0-40% ethyl acetate/hexanes to give the product as a white solid. (4.8 g, 87.7%); $^1$H NMR (300 MHz, CDCl$_3$) 7.65 (m, 4H), 7.40 (m, 6H), 4.64 (bs, 1H), 3.66-3.60 (m, 2H), 2.60-2.48 (m, 2H), 1.82 (m, 2H), 1.64 (s, 1H), 1.44-0.86 (m, 24H).

Intermediate d tert-Butyl ((2S)-5-amino-1-((tert-butyldiphenylsilyl)oxy)-6-methylheptan-2yl)carbamate To a solution (S)-tert-butyl (1-((tert-butyldiphenylsilyl)oxy)-6-methyl-5-oxoheptan-2-yl)carbamate (4.5 g, 9.03 mmol) and ammonium acetate (6.97 g, 90.3 mmol) in MeOH (100 mL) was added 4 Å molecular sieves and sodium cyanoborohydride (5.68 g, 90.3 mmol). The reaction mixture was stirred at room temperature overnight after which molecular sieves were filtered off and was washed with EtOAc. The organic layers were combined, washed with sodium bicarbonate and brine, dried over sodium sulfate and concentrated. The crude product was used directly in the next step without further purification.

Intermediate e

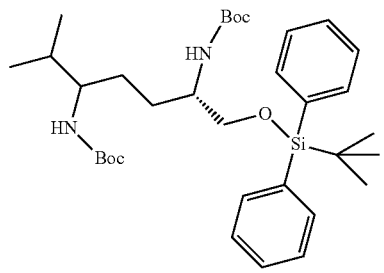 [SMILES: CC(C)C(CC[C@@H](CO[Si](c1ccccc1)(c1ccccc1)C(C)(C)C)NC(=O)OC(C)(C)C)NC(=O)OC(C)(C)C]

Di-tert-butyl ((2S)-1-((tert-butyldiphenylsilyl)oxy)-6-methylheptane-2,5-diyl)dicarbamate To a solution tert-butyl ((2S)-5-amino-1-((tert-butyldiphenylsilyl)oxy)-6-methylheptan-2-yl)carbamate (4.5 g, 9.0 mmol) in DCM (100 mL) at room temperature was added DIPEA (1.88 mL, 10.8 mmol) and (Boc)$_2$O (2.37 g, 10.8 mmol). The reaction was stirred at room temperature overnight. The reaction mixture was diluted with DCM, washed with saturated NaHCO$_3$ and brine, dried over sodium sulfate and concentrated. The residue was purified using an ISCO chromatograph with silica (0-30% ethyl acetate/hexane) to give the product as a white solid. (4.5 g, 83%); $^1$H NMR (300 MHz, CDCl$_3$) δ 7.61 (m, 4H), 7.60-7.34 (m, 6H), 4.68 (m, 1H), 4.25 (m, 1H), 3.66-3.55 (m, 3H), 3.38 (m, 1H), 1.63-1.05 (m, 31H), 0.88 (m, 6H).

Intermediate f

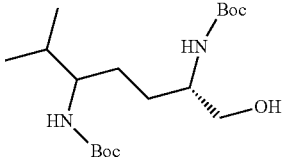 [SMILES: CC(C)C(CC[C@@H](CO)NC(=O)OC(C)(C)C)NC(=O)OC(C)(C)C]

Di-tert-butyl ((2S)-1-hydroxy 6-methylheptan-2,5-diyl)dicarbamate

To a solution di-tert-butyl ((2S)-1-((tert-butyldiphenylsilyl)oxy)-6-methylheptane-2,5-diyl)dicarbamate (4.5 g, 7.51 mmol) in THF (100 mL) at 0° C. was added 1 M TBAF (30.0 mL, 30 mmol). The reaction was stirred at room temperature overnight. The reaction mixture was quenched with saturated ammonium chloride, and extracted with EtOAc (3×10 mL). The organic layers were combined, washed with brine, dried over sodium sulfate and concentrated. The residue was purified using an ISCO chromatograph on silica (0-100% ethyl acetate/hexane) to give the product as a white solid. (2.4 g, 89%). $^1$H NMR (300 MHz, CDCl$_3$) δ 4.75 (m, 1H), 4.41-4.29 (m, 1H), 3.62-3.38 (m, 4H), 1.71-1.33 (m, 23H), 0.88 (m, 6H);

Intermediate g

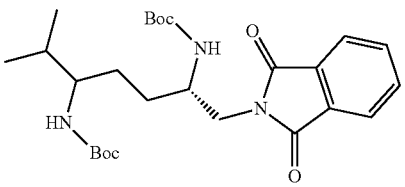 [SMILES: CC(C)C(CC[C@@H](CN1C(=O)c2ccccc2C1=O)NC(=O)OC(C)(C)C)NC(=O)OC(C)(C)C]

Di-tert-butyl ((2S)-1-(1,3-dioxoisoindolin-2-yl)-6-methylheptane-2,5-diyl)dicarbamate Triphenylphosphine (1.57 g, 6.0 mmol) and phthalimide (0.882 g, 6.0 mmol) were added to a flask containing dry THF (50 mL). Di-tert-butyl ((2S)-1-hydroxy-6-methylheptane-2,5-diyl)dicarbamate (1.81 g, 1.03 mmol) was added and the flask was cooled to 0° C. DIAD (1.21 g, 6.0 mmol) was added dropwise and reaction allowed to stir for 30 minutes at 0° C. and then overnight at room temperature. The mixture was concentrated under reduced pressure and the residue purified using an ISCO chromatograph on silica (0-70% ethyl acetate/hexanes) to give the product as a white solid $^1$H NMR (300 MHz, CDCl$_3$) δ 7.97-7.70 (m, 4H), 6.39 (bs, 2H), 4.97 (m, 2H), 4.34 (m, 1H), 3.94 (m, 1H), 3.69 (m, 1H), 1.67-0.85 (m, 29H);

Intermediate h

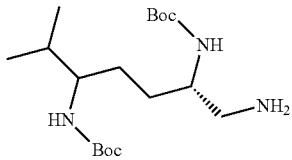 [SMILES: CC(C)C(CC[C@@H](CN)NC(=O)OC(C)(C)C)NC(=O)OC(C)(C)C]

Di-tert-butyl ((2S)-1-amino-6-methylheptane-2,5-diyl)dicarbamate

Di-tert-butyl ((2S)-1-(1,3-dioxoisoindolin-2-yl)-6-methylheptane-2,5-diyl)dicarbamate (3.0 g, 6.13 mmol) was dissolved in methanol (50 mL), and hydrazine monohydrate (1.2 mL, 24.5 mmol) was added to this solution. After the reaction mixture was refluxed for 2 hours, it was cooled to room temperature. The precipitate that formed was filtered and methanol was used to wash the filtrate. The filtrate was concentrated under reduced pressure. The residue was diluted with EtOAc, washed sequentially with saturated NaHCO$_3$, saturated ammonium chloride and brine. The organic layer was dried over sodium sulfate and concentrated. The crude product (2.4 g, yield: 100%) was used directly without further purification. $^1$H NMR (CDCl$_3$) (300 MHz) δ 4.99 (m, 1H), 4.60 (m, 1H), 3.50 (m, 1H), 2.70 (m, 1H), 1.67 (m, 4H), 1.31 (s, 9H), 1.27 (s, 9H), 0.85 (m, 6H).

Intermediate i

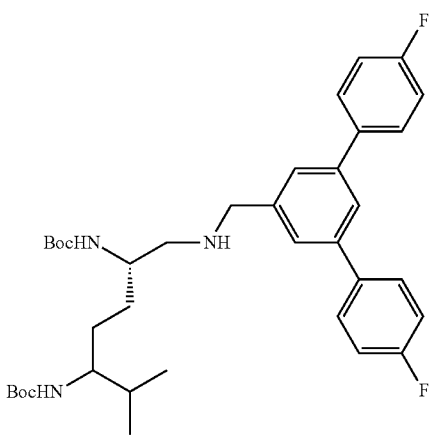 [SMILES: CC(C)C(CC[C@@H](CNCc1cc(-c2ccc(F)cc2)cc(-c2ccc(F)cc2)c1)NC(=O)OC(C)(C)C)NC(=O)OC(C)(C)C]

Di-tert-butyl ((2S)-1-(((4,4'-difluoro[1,1':3',1''-terphenyl]-5'-yl)methyl)amino)-6-methylheptane-2,5-diyl)dicarbamate To a solution of di-tert-butyl ((2S)-1-amino-6-methylheptane-2,5-diyl)dicarbamate (100 mg, 0.28 mmol) and 3,5-bis(trifluoromethyl)benzaldehyde (98.3 mg, 0.33 mmol) in MeOH (10 mL) was added 4 Å molecular sieves and sodium cyanoborohydride (52.4 mg, 0.834 mmol). The reaction mixture was stirred at room temperature overnight. The molecular sieves were filtered off and washed with EtOAc. The filtrate was concentrated and partitioned between EtOAc and sat. NaHCO₃ solution. The organic layers were combined, washed with brine, dried and concentrated. The residue was purified using an ISCO chromatograph (0-100% ethyl acetate/hexanes) to give the product (103 mg, 58% yield) as a semi-solid. $^1$H NMR (300 MHz, CDCl$_3$) δ 7.64-7.60 (m, 5H), 7.50 (s, 2H), 7.18-7.13 (m, 4H), 3.93 (m, 1H), 3.40 (m, 1H),), 2.73 (m, 2H), 1.80-1.30 (m, 22H), 0.85 (m, 6H).

Example 6. Preparation of(S)—N1-((4,4''-difluoro-[1,1':3',1''-terphenyl]-5'-yl)methyl)pentane-1,2,5-triaminium chloride

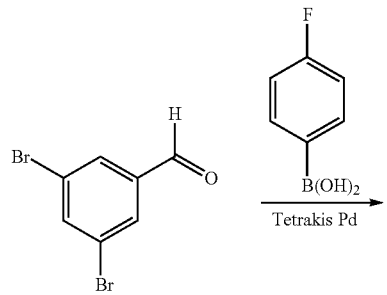

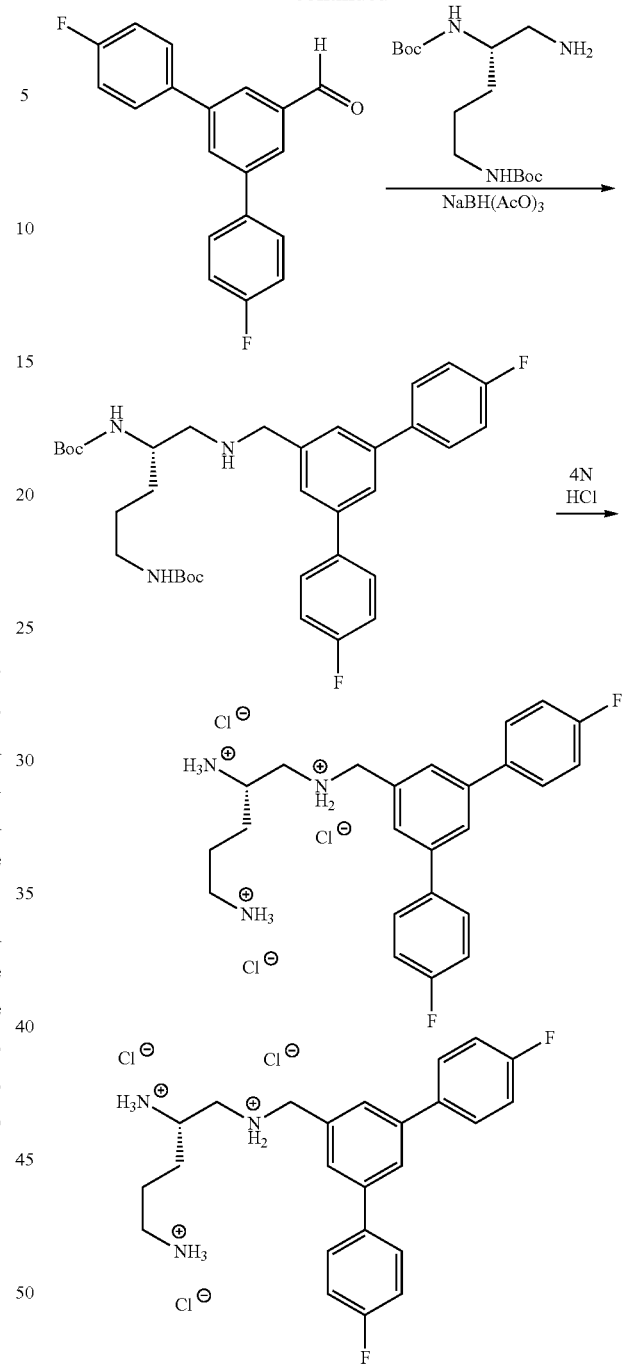

(S)—N1-((4,4''-Difluoro-[1,1':3',1''-terphenyl]-5'-yl)methyl)pentane-1,2,5-triaminium chloride The mixture of (S)-di-t-butyl (5-(((4,4''-difluoro-[1,1':3', 1''-terphenyl]-5'-yl)methyl)amino)-pentane-1,4-diyl) dicarbamate (0.2 g, 0.33 mmol) in DCM (2 mL), and 4 N HCl in 1,4-dioxane (1.2 mL) was stirred at room temperature for 4 hours. The solvents and excess HCl were removed, the residue was triturated with ethyl acetate/hexanes to give the product (S)—N$^1$-((4,4''-difluoro-[1,1':3',1''-terphenyl]-5'-yl)methyl)pentane-1,2,5-triamine as an off-white solid (165 mg, 95% yield). 1H NMR (CD₃OD, 300 MHz) δ 7.7 (s, 1H), 7.6 (m, 4H), 7.5 (s, 2H), 7.30 (m, 10H), 7.12 (m, 4H), 4.98 (bs, 2H), 3.8-3.3 (m, 8H).

The requisite intermediates were prepared as described in the following paragraphs.

Intermediate a

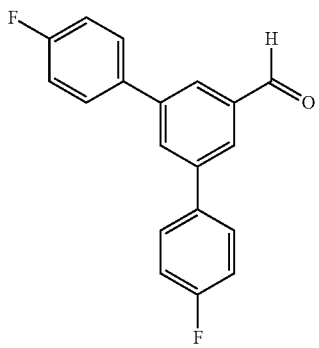 [SMILES: O=Cc1cc(-c2ccc(F)cc2)cc(-c2ccc(F)cc2)c1]

4,4''-Difluoro-[1,1':3',1''-terphenyl]-5'-carbaldehyde

The mixture of 3, 5-dibromobenzaldehyde (1.0 g, 3.8 mmol) in 1,4-dioxane/2 N Na₂CO₃ (20 mL, 4:1), 4-fluorophenylboronic acid (1.4 g, 10.2 mmol), and tetrakis(triphenylphosphine)-palladium (0.4 g) was degassed with N₂ and heated to reflux for 16 hours. The reaction mixture was worked up with ethyl acetate (40 mL) and was washed with brine (30 mL×2) and concentrated to give a dark paste. The paste was purified using ISCO chromatograph on 40 g of silica with ethyl acetate (0~10%)/hexanes to give the product (4, 4''-difluoro-[1,1':3',1''-terphenyl]-5'-carbaldehyde) as a beige solid (0.8 g, 71% yield). 1H NMR (CDCl3, 300 MHz): δ 10.17 (s, 1H), 8.05 (S, 2H), 7.98 (s, 1H), 7.68-7.64 (m, 4H), 7.22 (m, 4H).

Intermediate b

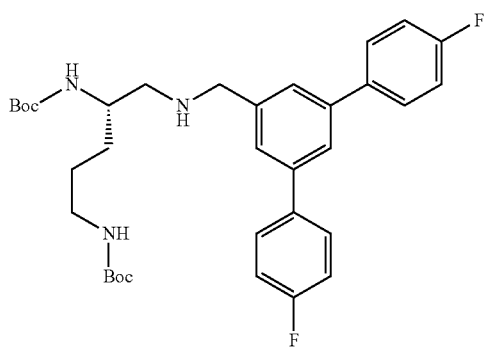 [SMILES: CC(C)(C)OC(=O)NCCC[C@@H](CNCc1cc(-c2ccc(F)cc2)cc(-c2ccc(F)cc2)c1)NC(=O)OC(C)(C)C]

Di-tert-butyl (5-(((4,4''-difluoro-[1,1':3',1''-terphenyl]-5'-yl)methyl)amino)pentane-1,4-diyl)(S)-dicarbamate The mixture of (4, 4''-difluoro-[1,1':3',1''-terphenyl]-5'-carbaldehyde (0.24 g, 0.78 mmol) in MeOH (10 mL), di-tert-butyl (5-aminopentane-1,4-diyl)(S)-dicarbamate (0.25 g, 0.78 mmol), and NaCNBH₃ with some 4 Å molecular sieves was stirred at room temperature for 16 hours. The reaction mixture was worked up with ethyl acetate (40 mL) and sat'd NaHCO₃ (30 mL) to give a beige paste. The paste was purified using an ISCO chromatograph on 24 g of silica with ethyl acetate (0~80%)/hexanes to give the product (di-tert-butyl (5-(((4,4''-difluoro-[1,1':3',1''-terphenyl]-5'-yl)methyl)amino)pentane-1,4-diyl)(S)-dicarbamate) as a clear gum (0.2 g, 46% yield). 1H NMR (CDCl₃, 300 MHz): δ 7.61 (m, 5H), 7.50 (s, 2H), 7.17 (m, 4H), 4.7 (bs, 2H), 3.92 (m, 2H), 3.78 (bm, 1H), 3.18 (m, 2H), 2.76 (m, 2H) 1.62-1.44 (m, 22H).

Example 7. Preparation of N1-(2-ammonioethyl)-N1-((4,4''-difluoro-[1,1':3',1''-terphenyl]-5'-yl)methyl)ethane-1,2-diaminium chloride

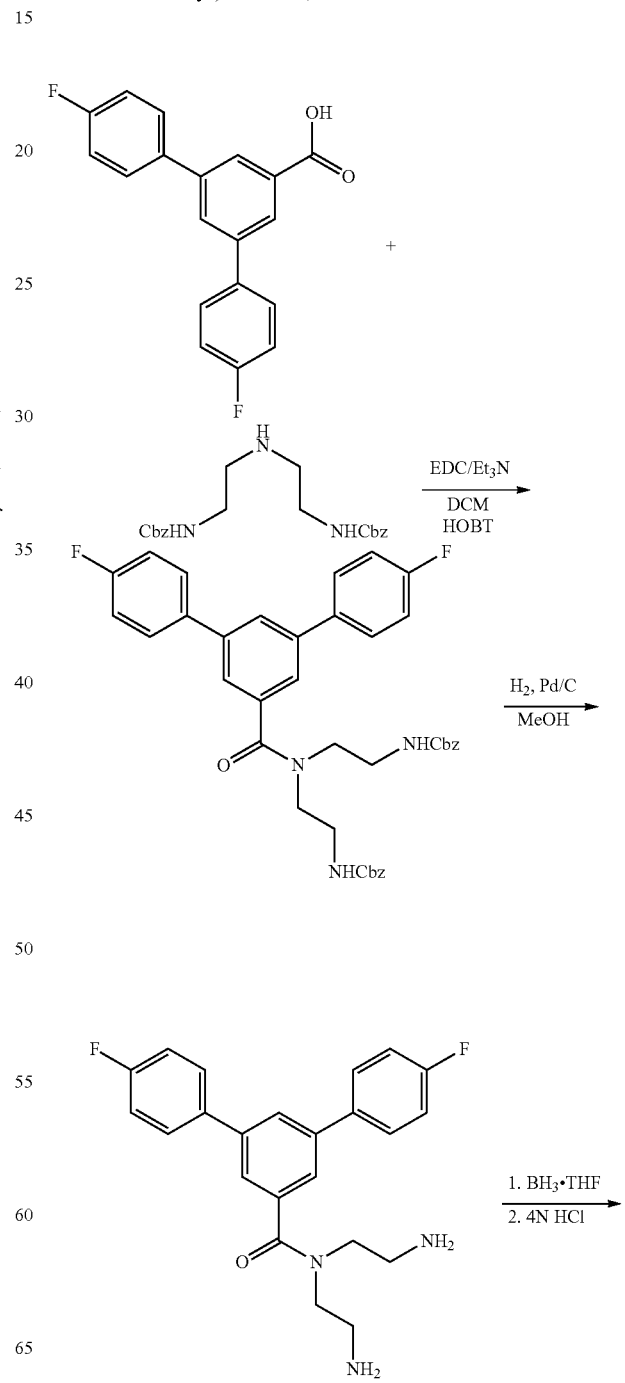

-continued

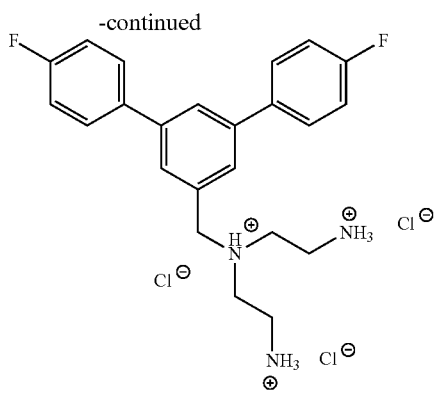

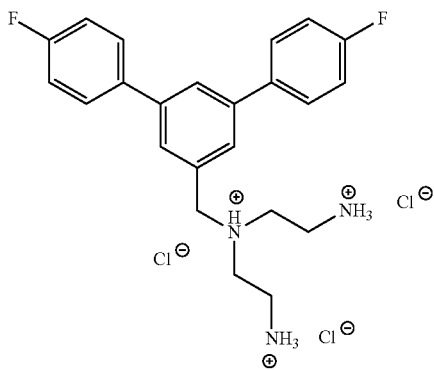

N1-(2-Ammonioethyl)-N1-((4,4"-difluoro-[1,1':3', 1"-terphenyl]-5'-yl)methyl)ethane-1,2-diaminium chloride The mixture of (N,N-bis(2-aminoethyl)-4,4"-difluoro-[1, 1':3',1"-terphenyl]-5'-carboxamide) (0.2 g, 0.65 mmol) in THF (6 mL), and 1 M BH₃ in THF (3 mL) was heated to reflux for 16 hours. The reaction mixture was quenched with MeOH (2 mL) and water (0.5 mL), and continued to be heat at reflux for 2 hours. The reaction mixture was concentrated, dissolved in MeOH (4 mL), and tBOC anhydride (0.5 g) was added. The reaction mixture was stirred at room temperature for 2 hours, then worked up with ethyl acetate (30 mL) and washed with brine (20 mL×2) and concentrated to give a beige paste. The paste was purified using an ISCO chromatograph on silica (12 g) with ethyl acetate (0~40%)/hexanes to give the product as a clear oil. The oil was dissolved into dichloromethane (1 mL) and stirred with 4N HCl (0.5 mL) in 1, 4-dioxane for 4 hours. The solvents and excess HCl were removed, the residue was triturated with ethyl acetate/hexanes to give the product (N¹-(2-aminoethyl)-N¹-((4, 4"-difluoro-[1,1':3',1"-terphenyl]-5'-yl) methyl)ethane-1,2-diamine) as a pale yellow solid (35 mg, 18% yield). 1H NMR (CD₃OD, 300 MHz): δ 7.96 (s, 3H), 7.88-7.84 (m, 4H), 7.27-7.22 (m, 4H), 4.61 (bs, 2H), 3.68-3.34 (m, 10H).

The requisite intermediates were prepared as described in the following paragraphs.

Intermediate a

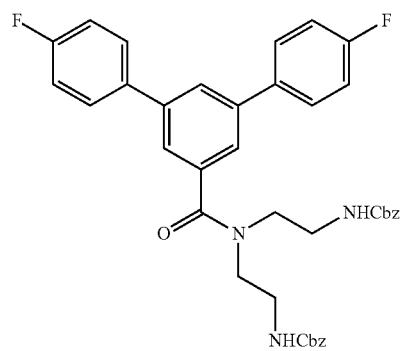 [SMILES: O=C(NCCN(CCNC(=O)OCc1ccccc1)C(=O)c1cc(-c2ccc(F)cc2)cc(-c2ccc(F)cc2)c1)OCc1ccccc1]

Dibenzyl (((4,4"-difluoro-[1,1':3',1"-terphenyl]-5'-carbonyl)azanediyl)bis(ethane-2,1-diyl))dicarbamate The mixture of 4,4"-difluoro-[1,1':3',1"-terphenyl]-5'-carboxylic acid (0.2 g, 0.65 mmol) in dichloromethane (10 mL), dibenzyl (azanediylbis(ethane-2,1-diyl))dicarbamate (0.25 g, 0.65 mmol), EDC (0.25 g, 1.3 mmol), trimethylamine (0.2 g, 2 mmol), and HOBT (0.2 g) was stirred at room temperature for 16 hours. The reaction mixture was worked up with ethyl acetate (30 mL) and washed with brine (20 mL×2) and concentrated to give a beige paste. The paste was purified using an ISCO chromatograph on silica (12 g) with ethyl acetate (0~50%)/hexanes to give the product (dibenzyl (((4,4"-difluoro-[1,1':3',1"-terphenyl]-5'-carbonyl)azanediyl)bis(ethane-2,1-diyl))dicarbamate) as a clear oil (0.34 g, 80% yield). ¹H NMR (CDCl₃, 300 MHz): δ 7.7 (s, 1H), 7.6 (m, 4H), 7.5 (s, 2H), 7.30 (m, 10H), 7.12 (m, 4H), 4.98 (bs, 4H), 3.8-3.3 (m, 8H).

Intermediate b

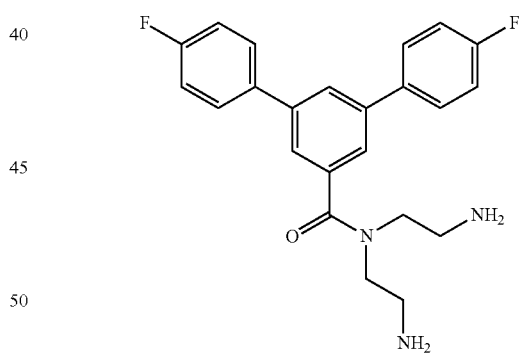

N,N-Bis(2-aminoethyl)-4,4"-difluoro-[1,1':3',1"-terphenyl]-5'-carboxamide

The mixture of (dibenzyl (((4,4"-difluoro-[1,1':3',1"-terphenyl]-5'-carbonyl)azanediyl)-bis(ethane-2,1-diyl))dicarbamate) (034 g, 0.51 mmol) in MeOH (10 mL), Pd/C (50 mg) was subjected hydrogenation with H₂ balloon for 16 hours. The reaction mixture was filtered from catalyst, the filtrate was concentrated to give the product (N,N-bis(2-aminoethyl)-4,4"-difluoro-[1,1':3',1"-terphenyl]-5'-carboxamide) as a clear oil (0.3 g, 95% yield). 1H NMR (CDCl3, 300 MHz): δ 7.62-7.56 (m, 7H), 7.20-7.15 (m, 4H), 3.65 (m, 2H), 3.42 (m, 10H), 3.1 (m, 2H), 2.9 (m, 2H).

Example 8. Preparation of 2-ammonio-1-((2-ammonioethyl)(3,5-bis(trifluoromethyl)benzyl)-14-azanyl)ethan-1-ylium chloride

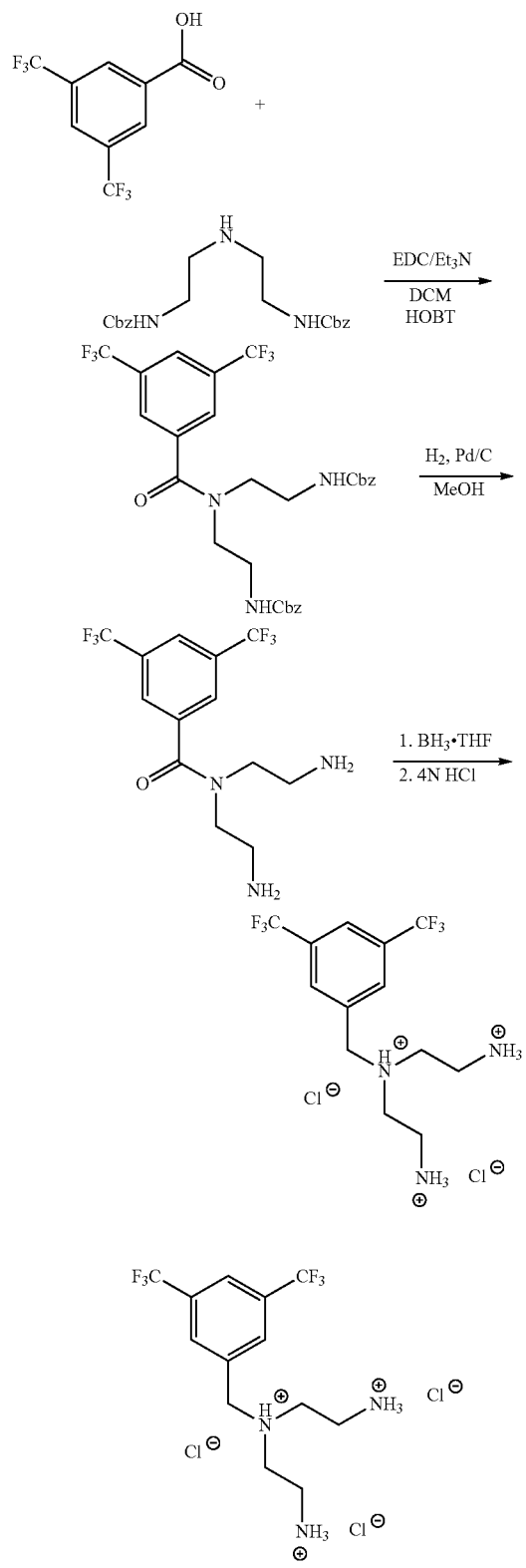

2-Ammonio-1-((2-ammonioethyl)(3,5-bis(trifluoromethyl)benzyl)-14-azanyl)ethan-1-ylium chloride The mixture of (N,N-bis(2-aminoethyl)-3,5-bis(trifluoromethyl)benzamide) (0.51 mg, 0.15 mmol) in THF (5 mL), and 1.0 M $BH_3$ in THF (1.0 mL) was heated to reflux for 16 hours. The reaction mixture was quenched with MeOH (1 mL) and water (0.25 mL), and continued to heat to reflux for 2 hours. The reaction mixture was concentrated, dissolved in MeOH (2 mL), and tBOC anhydride (0.2 g) was added. The reaction mixture was stirred at room temperature for 2 hours, then worked up with ethyl acetate (10 mL) and washed with brine (10 mL×2) then concentrated to give a beige paste. The paste was purified using an ISCO chromatograph on silica (12 g) with ethyl acetate (0~40%)/hexanes to give the product as a clear oil. The oil was dissolved in dichloromethane (1 mL) and stirred with 4N HCl in 1, 4-dioxane (0.3 mL) for 4 hours. The solvents and excess HCl were removed, the residue was triturated with ethyl acetate/hexanes to give the product ($N^1$-(2-aminoethyl)-$N^1$-(3, 5-bis(trifluoromethyl)benzyl) ethane-1,2-diamine trihydrochloride) as a pale yellow solid (20 mg, 41% yield). 1H NMR ($CD_3OD$, 300 MH): δ 7.8 (s, 1H), 7.5 (m, 2H), 3.66 (bs, 2H), 3.68-3.34 (m, 8H), 1.5 (bs, 4H).

The requisite intermediates were prepared as described in the following paragraphs.

Intermediate a

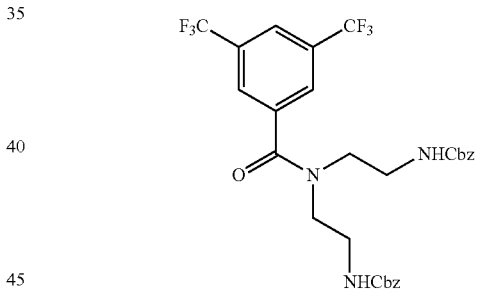

Dibenzyl (((3,5-bis(trifluoromethyl)benzoyl)azanediyl)bis(ethane-2,1-diyl))dicarbamate The mixture of 3,5-bis(trifluoromethylbenzoic acid (0.17 g, 0.65 mmol) in dichloromethane (10 mL), dibenzyl (azanediylbis(ethane-2,1-diyl))dicarbamate (0.25 g, 0.65 mmol), EDC (0.25 g, 1.3 mmol), trimethylamine (0.2 g, 2 mmol), and HOBT (0.2 g) was stirred at room temperature for 16 hours. The reaction mixture was worked up with ethyl acetate (30 mL) and washed with brine (20 mL×2) and concentrated to give a beige paste. The paste was purified using an ISCO chromatograph on silica (12 g) with ethyl acetate (0~50%)/hexanes to give the product (dibenzyl (((3, 5-bis(trifluoromethyl)benzoyl)azanediyl)bis(ethane-2,1-diyl))dicarbamate) as a clear oil (0.25 g, 71% yield). $^1$H NMR ($CDCl_3$, 300 MHz): δ 8.0 (s, 1H), 7.95 (s, 2H), 7.41 (s, 10H),), 5.14 (d, 4H), 3.8-3.3 (m, 8H).

Intermediate b

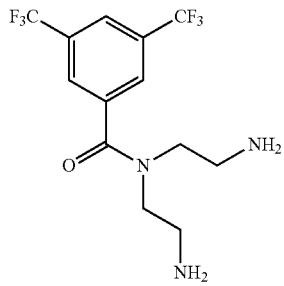 [SMILES: NCCN(CCN)C(=O)c1cc(C(F)(F)F)cc(C(F)(F)F)c1]

N,N-bis(2-aminoethyl)-3,5-bis(trifluoromethyl)benz-
amide

The mixture of (dibenzyl (((3,5-bis(trifluoromethyl)ben-zoyl)azanediyl)bis(ethane-2,1-diyl)) dicarbamate) (0.25 g, 0.46 mmol) in MeOH (10 mL), Pd/C (50 mg) was subjected hydrogenation with H₂ balloon for 16 hours. The reaction mixture was filtered catalyst, the filtrate was concentrated to give the product (N,N-bis(2-aminoethyl)-3,5-bis(trifluorom-ethyl)benzamide) as a clear oil (0.15 g, 95% yield). $^1$H NMR (CDCl$_3$, 300 MHz): δ 8.42 (s, 2H), 8.05 (s, 1H), 3.65 (m, 2H), 2.95-3.05 (m, 4H), 2.82 (m, 2H), 2.25 (m, 4H).

Example 9. Preparation of (S)—N$^1$-(2-(4,4"-dif-luoro-[1,1':3',1"-terphenyl]-5'-yl)-2-methylpropyl) pentane-1,2,5-triaminium chloride

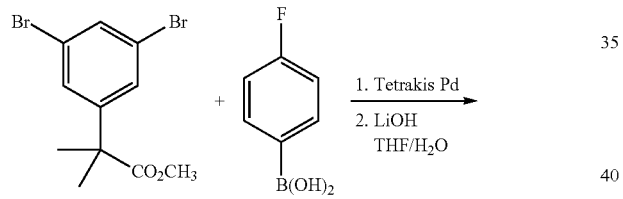

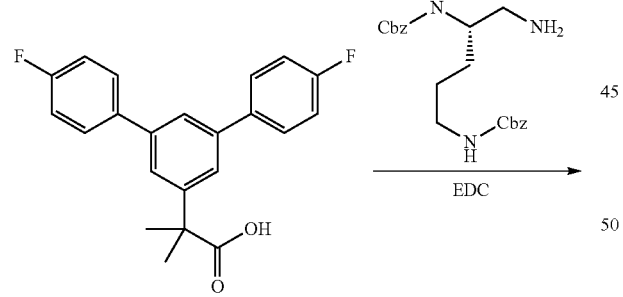

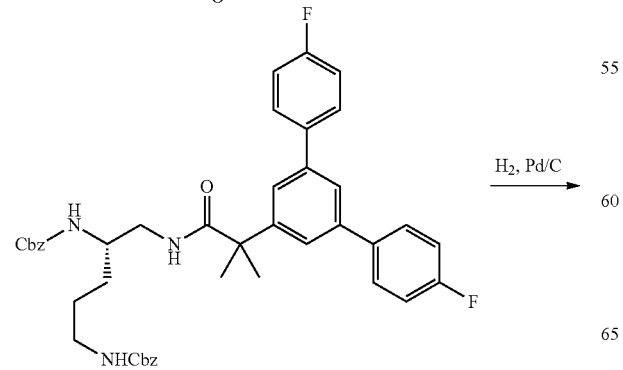

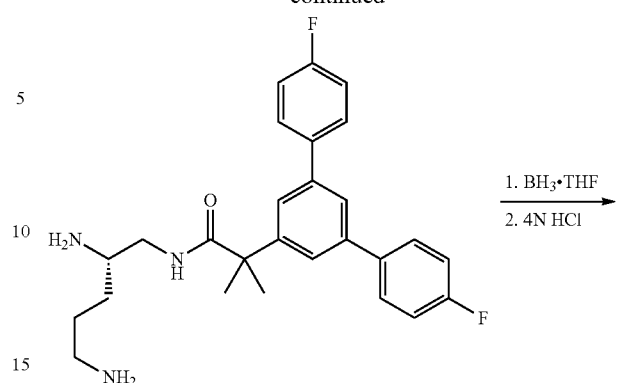

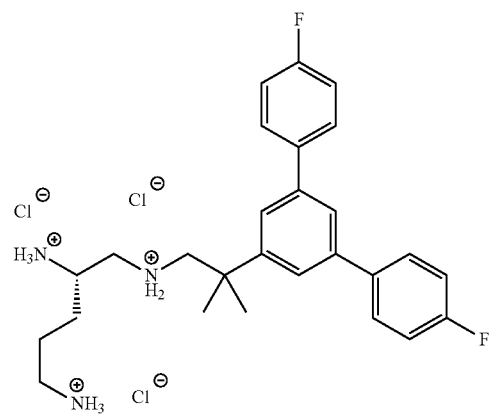

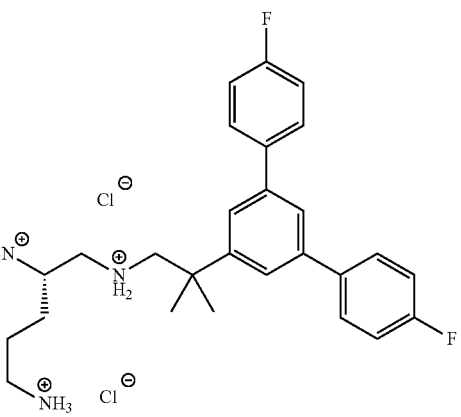

(S)—N[1]-(2-(4,4"-Difluoro-[1,1':3',1"-terphenyl]-5'-yl)-2-methylpropyl)pentane-1,2,5-triaminium chloride The mixture of (S)—N-(2, 5-diaminopentyl)-2-(4,4"-difluoro-[1,1':3',1"-terphenyl]-5'-yl)-2-methyl propanamide (0.25 g, 0.55 mmol) in THF (10 mL), and 1.0 M BH₃ in THF (4 mL) was heated to reflux for 16 hours. The reaction mixture was quenched with MeOH (2 mL) and water (0.5 mL), and then continued to be heated to reflux for 2 hours. The reaction mixture was concentrated, dissolved in MeOH (4 mL), and tBOC anhydride (0.6 g) was added. The reaction mixture was stirred at room temperature for 2 hours, then worked up with ethyl acetate (20 mL) and washed with brine (20 mL×2) and concentrated to give a beige paste. The paste was purified using an ISCO chromatograph on silica (24 g) with ethyl acetate (0~40%)/hexanes to give the product as a clear oil. The oil was dissolved in dichloromethane (2 mL) and stirred with 4N HCl in 1,4-dioxane (0.7 mL) for 4 hours. The solvents and excess HCl were removed, the residue was triturated with ethyl acetate/hexanes to give the product, (S)—N1-(2-(4,4"-difluoro-[1,1':3',1"-terphenyl]-5'-yl)-2-methylpropyl)pentane-1,2,5-triamine, as an off white solid (0.13 g, 51% yield). $^1$H NMR (DMSO-d6, 300 MHz): δ 8.6 (bs, 2H), δ 8.0 (bs, 2H), δ 7.91-7.86 (m, 4H), 7.8 (s, 1H), 7.67 (s, 2H), δ 7.37-7.31 (m, 4H), 3.7 (m, 1H), 3.3 (m, 4H), 2.82 (m, 2H), 1.67 (m, 4H). δ 1.58 (m, 6H).

The requisite intermediates were prepared as described in the following paragraphs.

Intermediate a

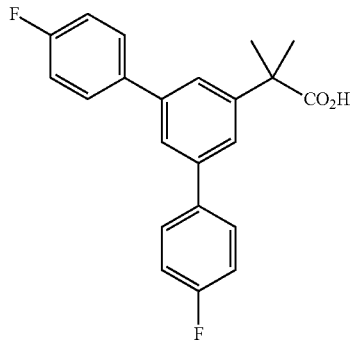 [SMILES: CC(C)(C(=O)O)c1cc(-c2ccc(F)cc2)cc(-c2ccc(F)cc2)c1]

2-(4,4"-Difluoro-[1,1':3',1"-terphenyl]-5'-yl)-2-methylpropanoic acid

The mixture of methyl 2-(3, 5-dibromophenyl)-2-methylpropanoate (0.5 g, 1.5 mmol) in 1,4-dioxane (20 mL) 2 N Na₂CO₃ (5 mL), 4-fluorophenylboronic acid (1.9 g, 13.3 mmol), tetrakis(triphenyl-phosphine)palladium (0.2 g) was degassed with N₂, then heated to reflux for 16 hour. The reaction mixture was worked up with ethyl acetate (60 mL) and was washed with brine (30 mL×2) and concentrated to give a dark paste. The paste was purified using an ISCO chromatograph on silica (40 g) with ethyl acetate (0~10%)/hexanes to give the product as a pale yellow solid. The solid was dissolved into THF/H₂O (10 mL, 4:1) and LiOH.H₂O (0.27 g, 6.4 mmol), and the mixture was stirred at room temperature for 16 hours. The reaction mixture was acidified with 1N HCl, and worked up with ethyl acetate (30 mL) and brine (20 mL×2) to give the product, 2-(4,4"-difluoro-[1,1':3',1"-terphenyl]-5'-yl)-2-methylpropanoic acid, as a beige solid (0.45 g, 80% yield). $^1$H NMR (CDCl₃, 300 MHz): δ 7.61-7.56 (m, 5H), 7.44 (m, 2H), 7.15 (m, 4H), 1.58 (bs, 6H).

Intermediate b

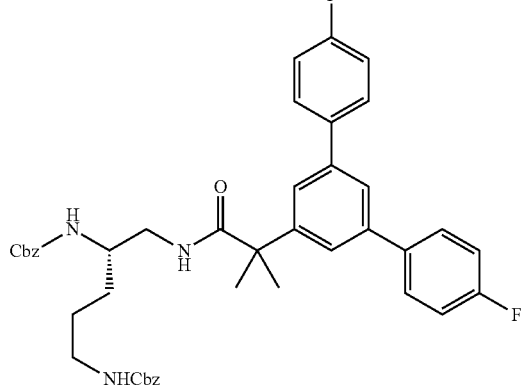

Dibenzyl (5-(2-(4,4"-difluoro-[1,1':3',1"-terphenyl]-5'-yl)-2-methylpropanamido)pentane-1,4-diyl)(S)-dicarbamate The mixture of dibenzyl (5-aminopentane-1,4-diyl)(S)-dicarbamate (0.32 g, 0.85 mmol) in dimethylchloride (10 mL), 2-(4,4"-difluoro-[1,1':3',1"-terphenyl]-5'-yl)-2-methylpropanoic acid (0.3 g, 0.85 mmol), EDC (0.32 g, 1.7 mmol), trimethylamine (0.3 g, 2.6 mmol), and HOBT (0.2 g) was stirred at room temperature for 16 hours. The reaction mixture was worked up with ethyl acetate (30 mL) and washed with brine (20 mL×2) and then concentrated to give a beige paste. The paste was purified using an ISCO chromatograph on silica (24 g) with ethyl acetate (0~40%)/hexanes to give the product, dibenzyl (5-(2-(4,4"-difluoro-[1,1':3',1"-terphenyl]-5'-yl)-2-methylpropanamido) pentane-1,4-diyl)(S)-dicarbamate, as a clear oil (0.4 g, 66% yield). $^1$H NMR (CDCl₃, 300 MHz): δ 7.58 (m, 5H), 7.47 (s, 2H), 7.30 (m, 10H), 7.15 (m, 4H), 5.85 (bs, 1H), 5.07 (m, 6H), 3.62 (m, 1H), 3.4-3.07 (m, 4H), 1.68-1.4 (m, 10H).

Intermediate c

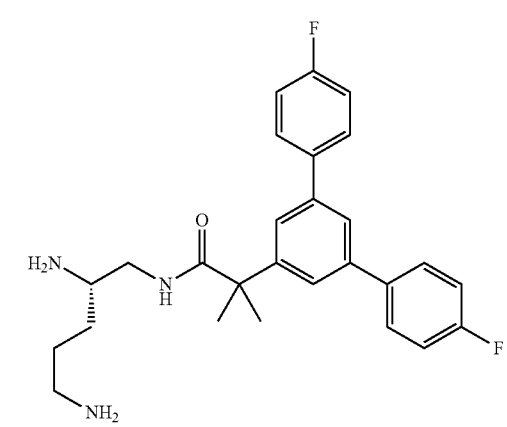 [SMILES: CC(C)(C(=O)NC[C@@H](N)CCCN)c1cc(-c2ccc(F)cc2)cc(-c2ccc(F)cc2)c1]

(S)—N-(2,5-Diaminopentyl)-2-(4,4"-difluoro-[1,1': 3',1"-terphenyl]-5'-yl)-2-methylpropanamide The mixture of dibenzyl (5-(2-(4, 4"-difluoro-[1,1':3',1"-terphenyl]-5'-yl)-2-methyl propanamido)pentane-1,4-diyl)

(S)-dicarbamate (0.4 g, 0.56 mmol) in MeOH (10 mL), Pd/C (60 mg) was subjected hydrogenation with $H_2$ for 16 hours. The reaction mixture was filtered from catalyst, the filtrate was concentrated to give the product, (S)—N-(2,5-diaminopentyl)-2-(4,4"-difluoro-[1,1':3',1"-terphenyl]-5'-yl)-2-methylpropanamide as a clear oil (0.25 g, 95% yield). $^1$H NMR (CDCl$_3$, 300 MHz): δ 7.58 (m, 5H), 7.46 (m, 2H), 7.17 (m, 4H), 3.3 (m, 1H), 3.0 (m, 1H), 2.8 (m, 1H), 2.6 (m, 1H), 2.22 (m, 1H), 1.68 (m, 4H), 1.5-1.2 (m, 6H).

Example 10. Preparation of (S)—N1-(2-(4,4"-difluoro-[1,1':3',1"-terphenyl]-5'-yl)ethyl)pentane-1,2,5-triaminium chloride

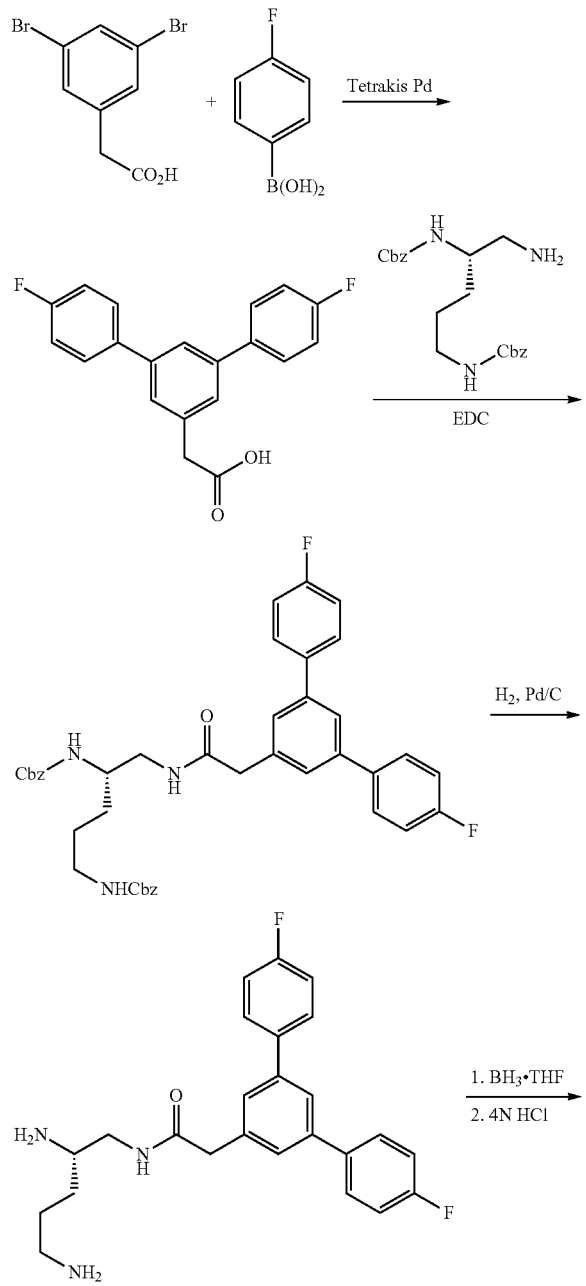

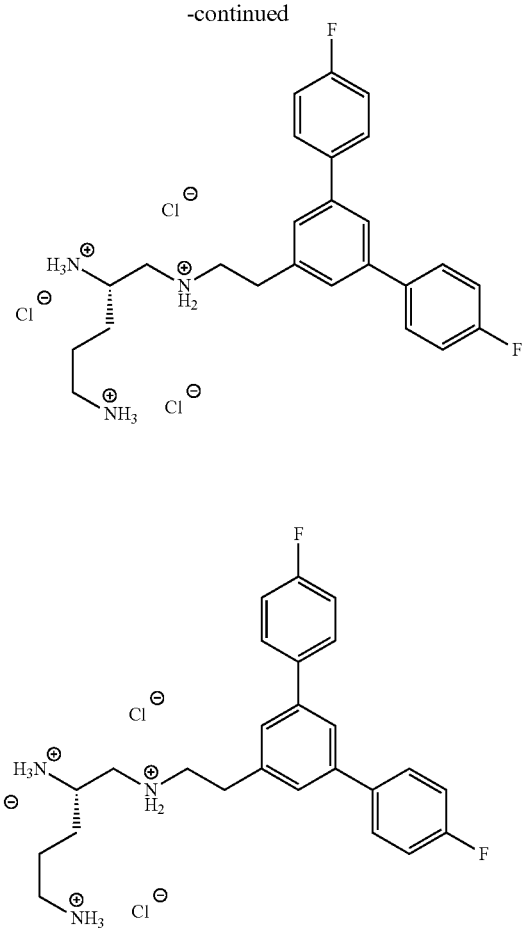

(S)—N1-(2-(4,4"-Difluoro-[1,1':3',1"-terphenyl]-5'-yl)ethyl)pentane-1,2,5-triaminium chloride The mixture of (S)—N-(2, 5-diaminopentyl)-2-(4, 4"-difluoro-[1,1':3',1"-terphenyl]-5'-yl)acetamide (0.15 g, 0.55 mmol) in THF (6 mL), and 1 M BH$_3$ in THF (1 mL) was heated to reflux for 16 hours. The reaction mixture was quenched with MeOH (2 mL) and water (0.5 mL), and continued to be heated to reflux for 2 hours. The reaction mixture was concentrated, dissolved in MeOH (4 mL), and tBOC anhydride (0.6 g) was added. The reaction mixture was stirred at room temperature for 2 hours, then worked up with ethyl acetate (20 mL) and washed with brine (20 mL×2) and concentrated to give a beige paste. The paste was purified using an ISCO chromatograph on silica (24 g) with ethyl acetate (0~40%)/hexanes to give the product as a clear oil. The oil was dissolved in dichloromethane (2 mL) and stirred with 4N HCl in 1,4-dioxane (0.5 mL) for 4 hours. The solvents and excess HCl were removed. The residue was triturated with ethyl acetate/hexanes to give the product (S)—N1-(2-(4,4"-difluoro-[1,1':3',1"-terphenyl]-5'-yl)ethyl)pentane-1,2,5-triamine as an off white solid (67 mg, 42% yield). $^1$H NMR (DMSO-d6, 300 MHz): δ 9.74 (bs, 2H), δ 8.64 (bs, 2H), δ 8.05 (bs, 2H), δ 7.84 (m, 5H), 7.59 (s, 2H), δ 7.33 (m, 4H), 3.70 (m, 2H), 3.47 (m, 4H), 3.21 (m, 2H), 2.84 (m, 2H), 1.74 (m, 4H).

The requisite intermediates were prepared as described in the following paragraphs.

Intermediate a

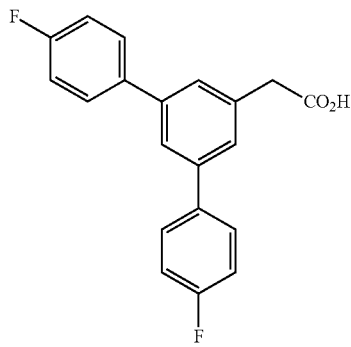 [SMILES: O=C(O)Cc1cc(-c2ccc(F)cc2)cc(-c2ccc(F)cc2)c1]

2-(4,4''-Difluoro-[1,1':3',1''-terphenyl]-5'-yl)acetic acid

The mixture of 3, 5-dibromophenylacetic acid (1 g, 3.4 mmol) in 1,4-dioxane/2 N $Na_2CO_3$ (30 mL, 4:1), 4-fluorophenylboronic acid (1.4 g, 10.2 mmol), and tetrakis(triphenylphosphine) palladium (0.4 g) was degassed with $N_2$ and heated to reflux for 16 hours. The reaction mixture was worked up with ethyl acetate (40 mL) and was washed with brine (30 mL×2) and concentrated to give a dark paste. The paste was purified using an ISCO chromatograph on silica (40 g) with ethyl acetate (0~40%)/hexanes to give the product, 2-(4,4''-difluoro-[1,1':3',1''-terphenyl]-5'-yl)acetic acid, as a beige solid (0.97 g, 88% yield). $^1$H NMR (CDCl$_3$, 300 MHz): δ 7.61-7.56 (m, 5H), δ 7.44 (m, 2H), δ 7.15 (m, 4H), δ 3.78 (bs, 2H).

Intermediate b

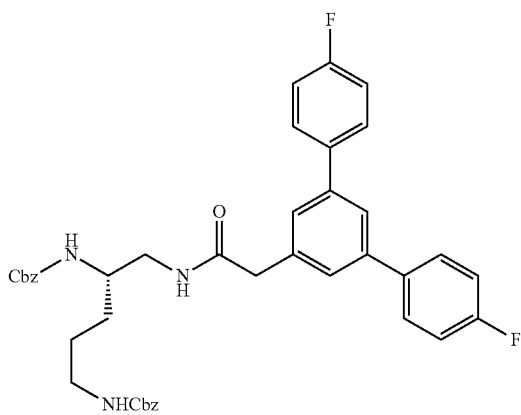 [SMILES: O=C(Cc1cc(-c2ccc(F)cc2)cc(-c2ccc(F)cc2)c1)NC[C@H](CCCNC(=O)OCc1ccccc1)NC(=O)OCc1ccccc1]

Dibenzyl (5-(2-(4,4''-difluoro-[1,1':3',1''-terphenyl]-5'-yl)acetamido)pentane-1,4-diyl)(S)-dicarbamate The mixture of (2-(4, 4''-difluoro-[1,1':3',1''-terphenyl]-5'-yl)acetic acid) (0.25 g, 0.77 mmol) in dimethylchloride (10 mL), dibenzyl (5-aminopentane-1,4-diyl)(S)-dicarbamate (0.28 g, 0.77 mmol), EDC (0.29 g, 1.7 mmol), trimethylamine (0.28 g, 1.54 mmol), and HOBT (0.2 g) was stirred at room temperature for 16 hours. The reaction mixture was worked up with ethyl acetate (30 mL) and washed with brine (20 mL×2) and concentrated to give a beige paste. The paste was purified using an ISCO chromatograph on silica (24 g) with ethyl acetate (0~60%)/hexanes to give the product, dibenzyl (5-(2-(4,4''-difluoro-[1,1':3',1''-terphenyl]-5'-yl)acetamido)pentane-1,4-diyl)(S)-dicarbamate, as a beige solid (0.35 g, 66% yield). $^1$H NMR (CDCl$_3$, 300 MHz): δ 8.18 (m, 1H), 7.79-7.74 (m, 3H), 7.73 (s, 1H), 7.50 (m, 2H), 7.32-7.26 (m, 12H), 7.08 (bd, 2H), 4.98 (m, 4H), 3.53 (m, 3H), 3.27 (m, 1H), 3.2-2.8 (m, 3H), 1.5 (m, 4H).

Intermediate c

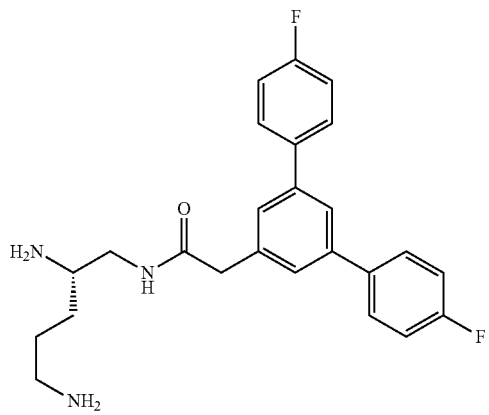 [SMILES: NCCC[C@H](N)CNC(=O)Cc1cc(-c2ccc(F)cc2)cc(-c2ccc(F)cc2)c1]

(S)—N-(2,5-Diaminopentyl)-2-(4,4''-difluoro-[1,1':3',1''-terphenyl]-5'-yl)acetamide The mixture of dibenzyl (5-(2-(4,4''-difluoro-[1,1':3',1''-terphenyl]-5'-yl) acetamido)pentane-1,4-diyl)(S)-dicarbamate (0.25 g, 0.36 mmol) in MeOH (10 mL), Pd/C (50 mg) was subjected hydrogenation with $H_2$ for 16 hours. The reaction mixture was filtered from catalyst, the filtrate was concentrated to give the product, (S)—N-(2,5-diaminopentyl)-2-(4,4''-difluoro-[1,1':3',1''-terphenyl]-5'-yl)acetamide, as a clear oil (0.15 g, 95% yield). $^1$H NMR (CDCl$_3$, 300 MHz): δ 7.66 (m, 5H), 7.58 (m, 2H), δ 7.19 (m, 4H), 6.38 (bs, 1H) 3.7 (m, 2H), 3.4 (m, 1H), 3.02 (m, 1H), 2.84 (m, 1H), 2.7 (m, 2H), 1.77 (m, 4H).

Example 11. Preparation of (R)-5-((4,4''-difluoro-[1,1':3',1''-terphenyl]-5'-yl)oxy)pentane-1,4-diaminium chloride

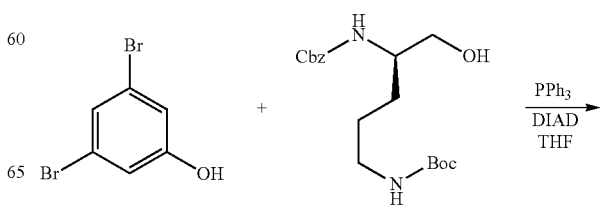

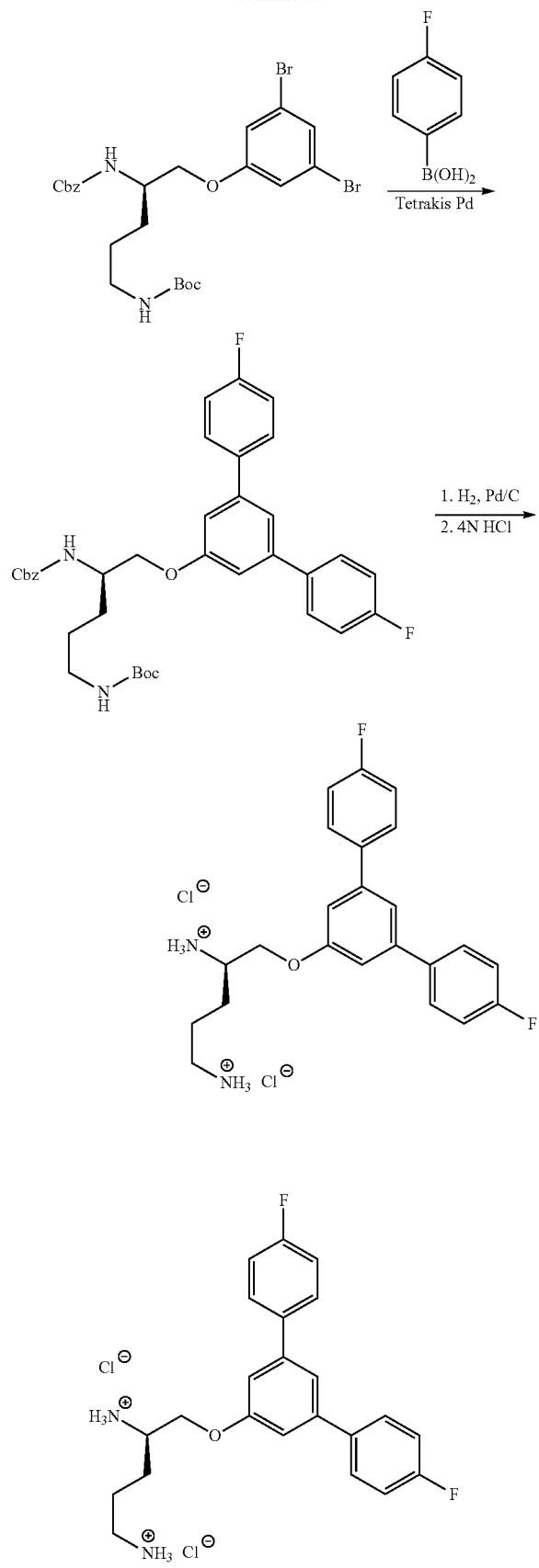

(R)-5-((4,4''-Difluoro-[1,1':3',1''-terphenyl]-5'-yl)oxy)pentane-1,4-diaminium

The mixture of benzyl tert-butyl (5-((4,4''-difluoro-[1,1':3',1''-terphenyl]-5'-yl)oxy)pentane-1,4-diyl)(R)-dicarbamate (0.25 g, 0.4 mmol) in MeOH (6 mL), Pd/C (50 mg) was subjected hydrogenation with H$_2$ balloon for 16 hours. The reaction mixture was filtered from catalyst, the filtrate was concentrated to give the product as a clear oil. The oil was dissolved in dichloromethane (1 mL) and stirred with 4N HCl in 1,4-dioxane (0.5 mL) for 4 hours. The solvents and excess HCl were removed. The residue was triturated with ethyl acetate/hexanes to give the product, (R)-5-((4,4''-difluoro-[1,1':3',1''-terphenyl]-5'-yl)oxy)pentane-1,4-diamine dihydrochloride, as a white solid (168 mg, 90% yield). $^1$H NMR (DMSO-d6, 300 MHz): δ 8.49 (s, 1H), 8.13 (s, 3H), 7.83 (s, 3H), δ 7.52 (m, 4H), 7.5 (s, 1H), δ 7.35-7.27 (m, 6H), 4.77 (m, 1H), 4.38 (m, 1H), 4.25 (m, 1H), 2.85 (s, 2H), 1.81 (m, 4H).

The requisite intermediates were prepared as described in the following paragraphs.

Intermediate a

Benzyl tert-butyl (5-(3,5-dibromophenoxy)pentane-1,4-diyl)(R)-dicarbamate

The mixture of 3,5-dibromophenol (0.2 g, 0.79 mmol) in THF, benzyl tert-butyl (5-hydroxypentane-1,4-diyl)(R)-dicarbamate (0.37 g, 0.95 mmol), triphenylphosphine (0.31 g, 1.2 mmol), and DIAD (0.21 g, 1 mmol) was stirred at room temperature for 16 hours. The reaction mixture was worked up with ethyl acetate (40 mL) and washed with was washed with brine (30 mL×2) and concentrated to give a yellow paste. The paste was purified using an ISCO chromatograph on silica (24 g) with ethyl acetate (0~20%)/hexanes to give the product (benzyl t-butyl (5-(3, 5-dibromophenoxy)pentane-1,4-diyl)(R)-dicarbamate) as an off white solid (0.32 g, 65% yield). $^1$H NMR (CDCl$_3$, 300 MHz): δ 7.37 (m, 8H), 6.99 (s, 2H), 5.14 (m, 2H), 4.6 (m, 2H), 2.8 (m, 2H), 1.78 (m, 4H), 1.48 (bs, 9H).

Intermediate b

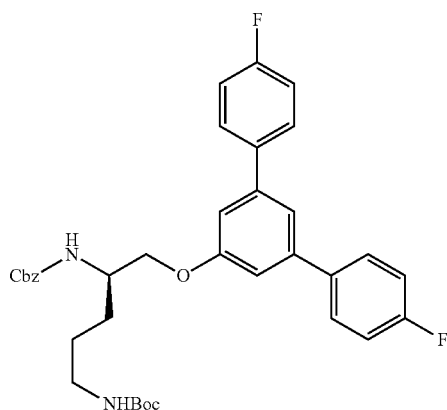 [SMILES: CC(C)(C)OC(=O)NCCC[C@H](COc1cc(-c2ccc(F)cc2)cc(-c2ccc(F)cc2)c1)NC(=O)OCc1ccccc1]

Benzyl tert-butyl (5-((4,4"-difluoro-[1,1':3',1"-terphenyl]-5'-yl)oxy)pentane-1,4-diyl)(R)-dicarbamate The mixture of (benzyl tert-butyl (5-(3,5-dibromophenoxy)pentane-1,4-diyl)(R)-dicarbamate) (0.3 g, 0.48 mmol) in 1,4-dioxane/2N Na$_2$CO$_3$ (8 mL, 4:1), 4-fluorophenylboronic acid (0.2 g, 1.45 mmol), and tetrakis(triphenylphosphine)palladium (60 mg) was degassed with N$_2$ and heated to reflux for 16 hours. The reaction mixture was worked up with ethyl acetate (20 mL) and washed with brine (10 mL×2) and concentrated to give a dark paste. The paste was purified using an ISCO chromatograph on silica (24 g) with ethyl acetate (0~40%)/hexanes to give the product, benzyl tert-butyl (5-((4,4"-difluoro-[1,1':3',1"-terphenyl]-5'-yl)oxy pentane-1,4-diyl)(R)-dicarbamate, as a clear oil (0.25 g, 83% yield). $^1$H NMR (CDCl$_3$, 300 MHz): δ 7.69 (m, 5H), 7.6 (s, 2H), δ 7.52 (m, 4H), δ 7.35-7.27 (m, 5H), 5.14 (m, 2H), 4.6 (m, 2H), 2.85 (s, 2H), 1.81 (m, 4H), 1.48 (bs, 9H).

Example 12. Preparation of (R)-4-(4,4"-difluoro-[1,1':3',1"-terphenyl]-5'-yl)butane-1,2-diaminium chloride

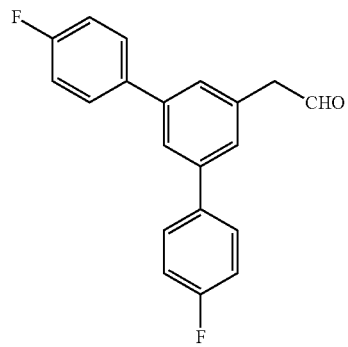

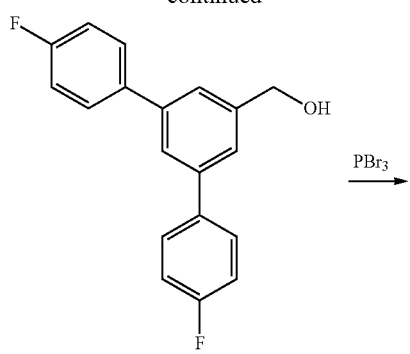

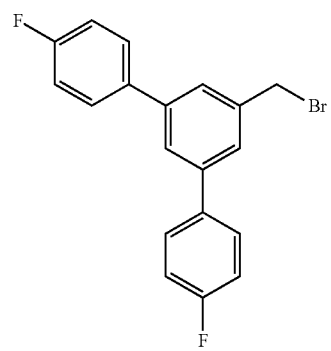 [SMILES: Fc1ccc(-c2cc(CBr)cc(-c3ccc(F)cc3)c2)cc1]

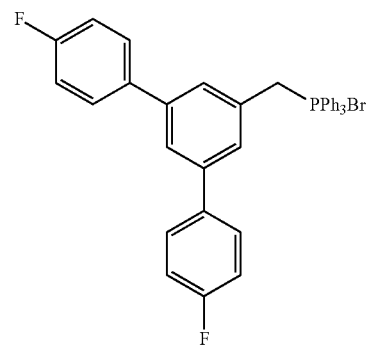

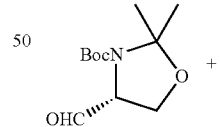

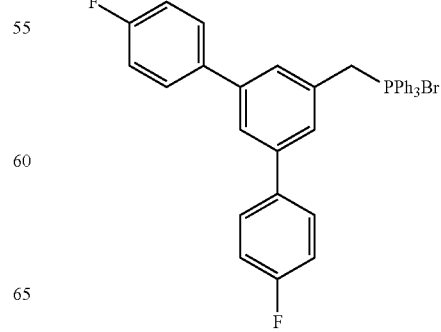

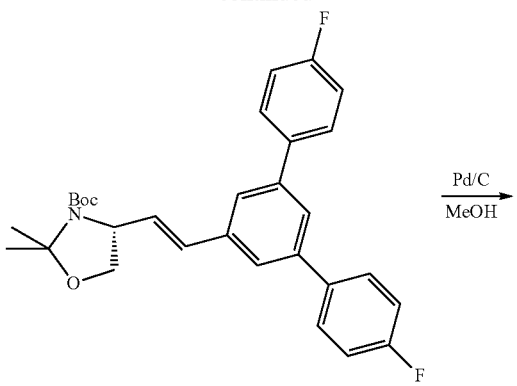

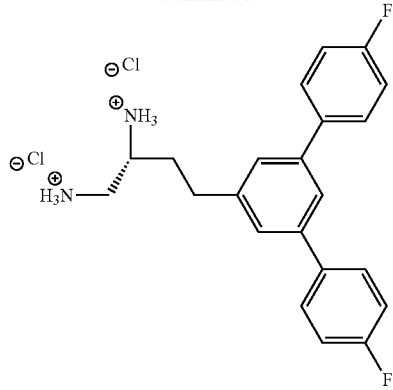

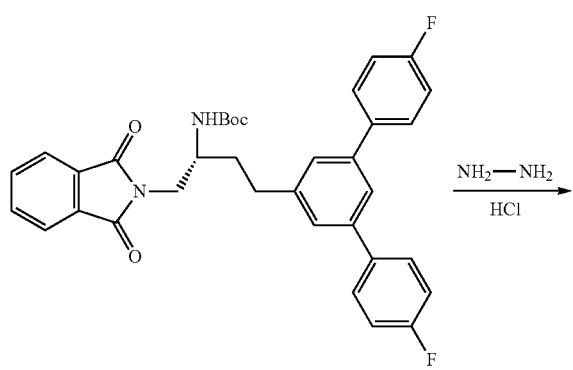

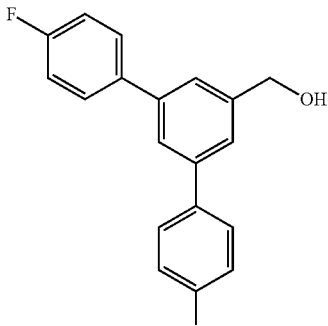

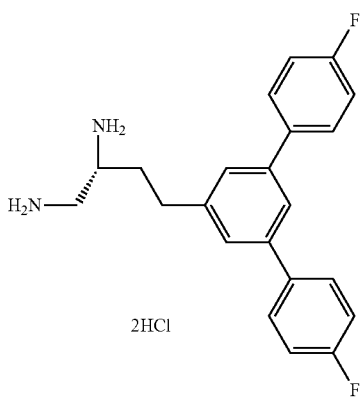

(R)-4-(4,4''-Difluoro-[1,1':3',1''-terphenyl]-5'-yl)butane-1,2-diaminium chloride t-Butyl (R)-(4-(4,4''-difluoro-[1,1':3',1''-terphenyl]-5'-yl)-1-(1,3-dioxoisoindolin-2-yl)butan-2-yl)carbamate (60 mg, 0.10 mmol) was dissolved in methanol (5 mL) and hydrazine monohydrate (20 µL, 0.40 mmol) was added. The reaction mixture was refluxed for 2 hours and then allowed to cool to room temperature. The solvent was removed and the residue was triturated with DCM, then the solid was removed by filtration. The filtrate was concentrated and purified using an ISCO chromatograph with silica (0-10% methanol/methylene chloride+1% NH$_4$OH) to give the boc protected intermediate, which was dissolved in MeOH (1 mL), then added 4 N HCl in dioxane (0.1 mL). After stirring for 1 hour at room temperature. The solvent was removed and the solid was triturated with EtOAc. The solid was collected to afford the desired compounds (21 mg, 64%) as white solid; $^1$H NMR (DMSO) (300 MHz) δ: 7.80 (m, 4H), 7.70 (s, 1H), 7.53 (s, 2H), 7.30 (m, 4H), 3.36 (m, 2H), 3.16 (m, 1H), 2.80 (m, 2H), 2.04 (m, 2H).

The requisite intermediates were prepared as described in the following paragraphs.

Intermediate a (4,4''-Difluoro-[1,1':3',1''-terphenyl]-5'-yl)methanol

To a solution of 2-(4,4''-difluoro-[1,1':3',1''-terphenyl]-5'-yl)acetaldehyde (520 mg, 1.77 mmol) in ethanol (10 mL) was added NaBH$_4$ (134 mg, 3.54 mmol) at 0° C. The mixture was stirred for 30 minutes at room temperature then quenched by adding acetone. The reaction mixture was concentrated and the residue was diluted with EtOAc. The resulting solution was washed with 1N NaOH followed by 1N HCl. The organic layer was washed with brine and dried over sodium sulfate and concentrated to give the crude alcohol which was used for the next step without further purification.

Intermediate b

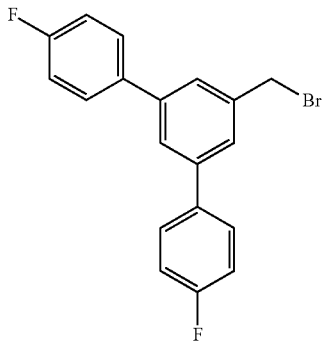

5'-(Bromomethyl)-4,4"-difluoro-1,1':3',1"-terphenyl

Within a pressure tube was added (4,4"-difluoro-[1,1':3',1"-terphenyl]-5'-yl)methanol (520 mg, 1.77 mmol), and PBr$_3$ (1.68 mL, 17.7 mmol), then sealed and heated to 80° C. for 1 hour. The reaction mixture was cooled to room temperature and diluted with DCM. The organic solution was washed with sat. NaHCO$_3$, brine, and dried over Na$_2$SO$_4$. The organic layer was concentrated and the residue purified using an ISCO chromatograph on silica to afforded the bromide as white solid (463 mg, 73%); $^1$H NMR (CDCl$_3$) (300 MHz) δ 7.62-7.57 (m, 7H), 7.17 (m, 4H), 4.61 (s, 2H).

Intermediate c

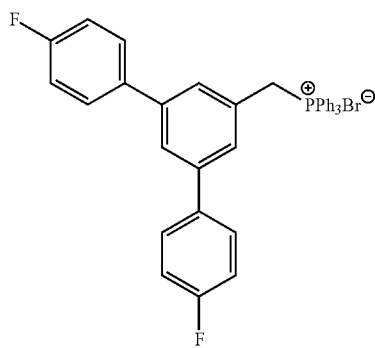

((4,4"-Difluoro-[1,1':3',1"-terphenyl]-5'-yl)methyl) triphenylphosphonium bromide To a flask was added 5'-(bromomethyl)-4,4"-difluoro-1,1':3',1"-terphenyl (463 mg, 1.29 mmol) followed by triphenyl phosphine (338 mg, 1.29 mmol) and toluene (10 mL). The resulting mixture was refluxed for 2 hours. After cooling to room temperature, the solvent was removed o afford the crude salt as white solid (810 mg, quant.) which was used for the next step without further purification.

Intermediate d

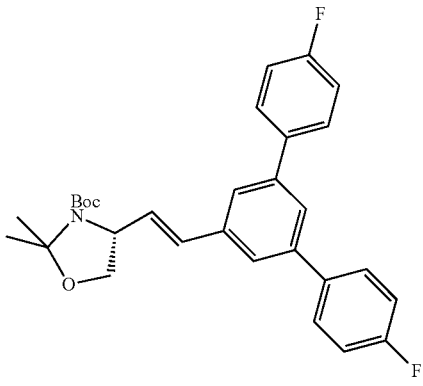

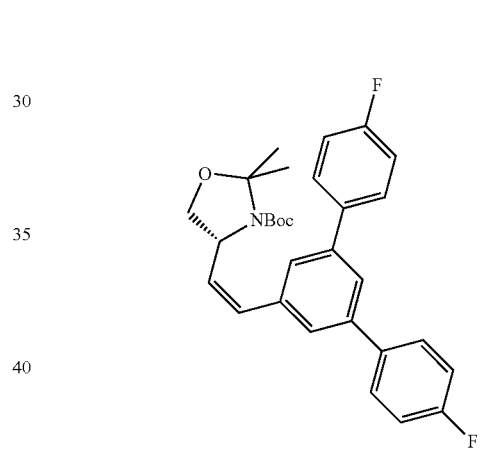

t-Butyl (R)-4-(2-(4,4"-difluoro-[1,1':3',1"-terphenyl]-5'-yl)vinyl)-2,2-dimethyloxazolidine-3-carboxylate, (E,Z)

To a solution of ((4,4"-difluoro-[1,1':3',1"-terphenyl]-5'-yl)methyl)triphenylphosphonium bromide (300 mg, 0.48 mmol) in THF (5 mL) at −78° C. under N$_2$ was added (LiHMDS, 1.0 M in THF, 0.7 mL, 0.7 mmol) was added dropwise. After stirring at −78° C. for 30 minutes, a solution of Garner's aldehyde (110 mg, 0.48 mmol) in THF (1 mL) was added dropwise. The reaction mixture was stirred at −78° C. for 1 hour then warmed to room temperature with stirring overnight. The reaction mixture was quenched with sat. NH$_4$Cl solution and extracted with EtOAc. The organic layer was washed with brine and dried over Na$_2$SO$_4$. Concentration and purification with column afforded both the Z and E mixture of the desired product as a colorless oil (176 mg, 75%). $^1$H NMR (CDCl$_3$) (300 MHz) δ: 7.6 (m, 7H), 7.18 (m, 4H), 6.62 (m, 1H), 6.30 (m, 1H), 4.64-4.42 (m, 1H), 4.08 (m, 1H), 3.84 (m, 1H), 1.59 (m, 6H), 1.47 (s, 9H).

Intermediate e

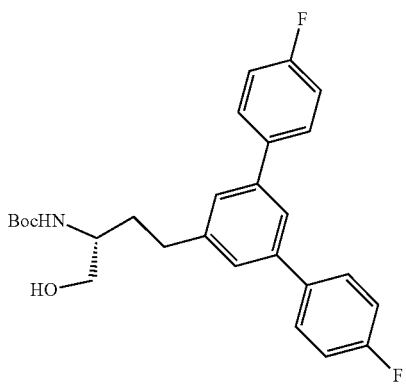 [SMILES: CC(C)(C)OC(=O)N[C@@H](CO)CCc1cc(-c2ccc(F)cc2)cc(-c2ccc(F)cc2)c1]

tert-butyl (R)-(4-(4,4''-difluoro-[1,1':3',1''-terphenyl]-5'-yl)-1-hydroxybutan-2-yl)carbamate The mixture of the Z and E isomers of intermediate 12c (176 mg, 036 mmol) in MeOH (15 mL) was degassed with N₂ for 5 min the added Pd/C (10% in Carbon, 30 mg). The reaction mixture was stirred under H₂ overnight. The solid was removed by Celite filtration and the filtrate was concentrated and purified by column to afford the desired compound (72 mg, 45%) as colorless oil. ¹H NMR (CDCl₃) (300 MHz) δ: 7.61 (m, 4H), 7.48 (s, 1H), 7.37 (s, 2H), 7.16 (m, 4H), 4.78 (m, 1H), 3.80-3.45 (m, 3H), 2.83 (m, 2H), 1.96 (m, 2H), 1.48 (s, 9H).

Intermediate f

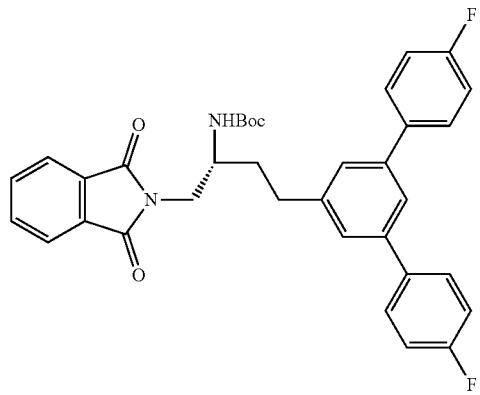 [SMILES: CC(C)(C)OC(=O)N[C@H](CCc1cc(-c2ccc(F)cc2)cc(-c2ccc(F)cc2)c1)CN1C(=O)c2ccccc2C1=O]

t-Butyl (R)-(4-(4,4''-difluoro-[1,1':3',1''-terphenyl]-5'-yl)-1-(1,3-dioxoisoindolin-2-yl)butan-2-yl)carbamate Triphenylphosphine (50 mg, 0.19 mmol) and phthalimide (28 mg, 0.19 mmol) were added to a flask containing dry THF (5 mL). t-Butyl (R)-(4-(4,4''-difluoro-[1,1':3',1''-terphenyl]-5'-yl)-1-hydroxybutan-2-yl)carbamate (72 mg, 0.16 mmol) was added and the flask was cooled to 0° C. DIAD (38.6 mg, 0.19 mmol) was added dropwise and reaction was allowed to stir for 30 minutes at 0° C. and overnight at room temperature. The mixture was concentrated under reduced pressure and residue purified using an ISCO chromatograph with silica (0-70% ethyl acetate/hexane) to give product as a white solid. (60 mg, 65%); ¹H NMR (CDCl₃) (300 MHz) δ: 7.85 (m, 4H), 7.59 (m, 4H), 7.52 (s, 1H), 7.34 (s, 2H), 7.15 (m, 4H), 6.39 (br s, 1H), 4.71 (m, 1H), 3.78 (m, 2H), 2.86 (m, 2H), 2.10-1.75 (m, 2H), 1.26 (m, 9H).

Example 13. Preparation of (S)-5-((4,4''-difluoro-[1,1':3',1''-terphenyl]-5'-yl)oxy)pentane-1,4-diaminium chloride

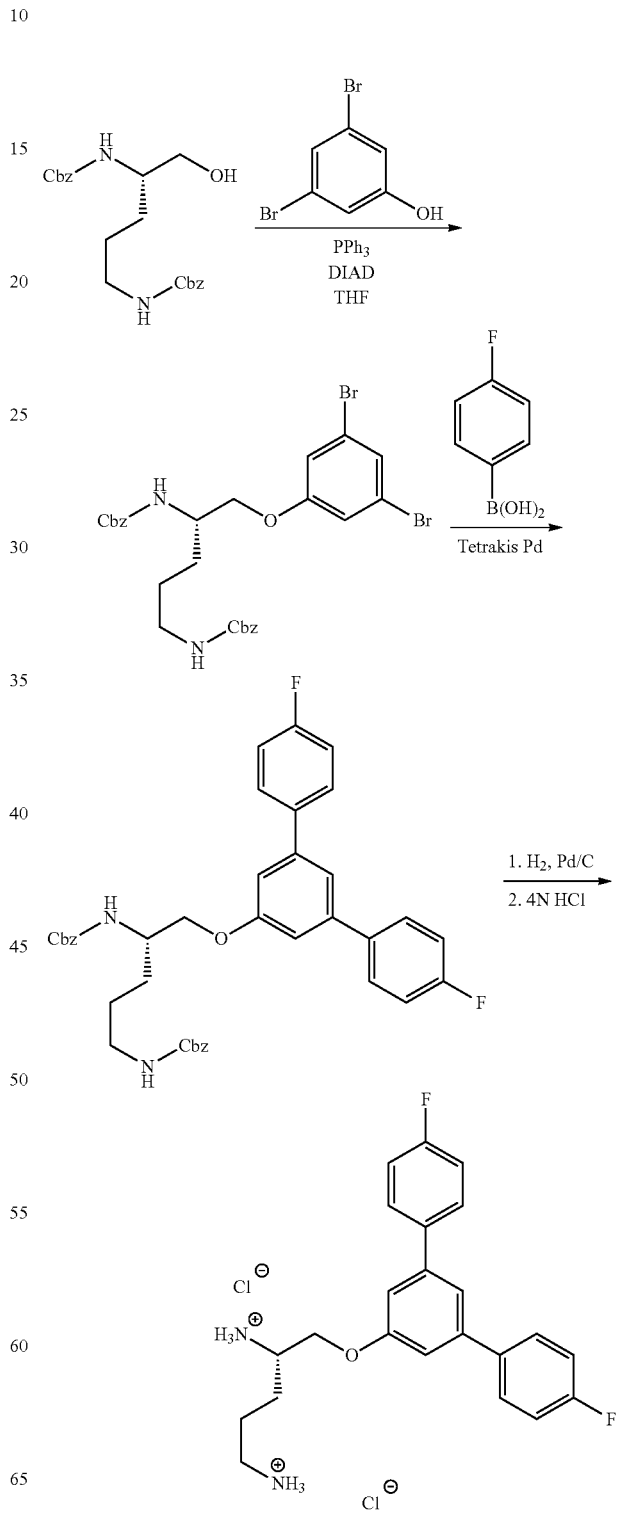

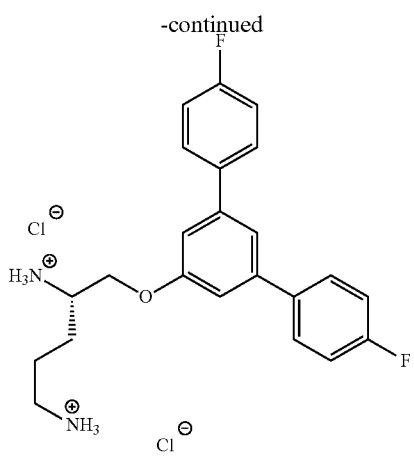

(S)-5-((4,4''-Difluoro-[1,1':3',1''-terphenyl]-5'-yl)oxy)pentane-1,4-diaminium chloride The mixture of (dibenzyl (5-((4,4''-difluoro-[1,1':3',1''-terphenyl]-5'-yl)oxy)pentane-1,4-diyl)(S)-dicarbamate) (0.20 g, 0.31 mmol) in MeOH (8 mL), Pd/C (40 mg) was subjected hydrogenation with H₂ for 16 hours. The reaction mixture was filtered from catalyst, the filtrate was concentrated to give the product (which was isolated as the dihydrochloride salt after treatment with 4 N HCl), (S)-5-((4,4''-Difluoro-[1,1':3',1''-terphenyl]-5'-yl)oxy)pentane-1,4-diaminium chloride, as a white solid (0.11 g, 92% yield). ¹H NMR (CDCl₃, 300 MHz): δ 8.0 (s, 1H), 7.58 (m, 4H), 7.3 (m, 1H), 7.28-7.06 (m, 6H), 4.02 (m, 1H), 3.87 (m, 1H), 3.2 (m, 1H), 2.79 (m, 2H), 1.81 (m, 4H).

The requisite intermediates were prepared as described in the following paragraphs.

Intermediate a

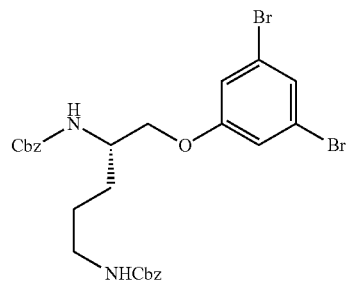 [SMILES: O=C(NCCC[C@@H](COc1cc(Br)cc(Br)c1)NC(=O)OCc1ccccc1)OCc1ccccc1]

Dibenzyl (5-(3,5-dibromophenoxy)pentane-1,4-diyl)(S)-dicarbamate

The mixture of 3,5-dibromophenol (0.86 g, 3.42 mmol) in THF, dibenzyl (5-hydroxypentane-1,4-diyl)(S)-dicarbamate (1.1 g, 2.85 mmol), triphenylphosphine (0.9 g, 3.42 mmol), and DIAD (0.69 g, 3.42 mmol) was stirred at room temperature for 16 hours. The reaction mixture was worked up with ethyl acetate (60 mL) and was washed with brine (30 mL×2) and concentrated to give a yellow paste. The paste was purified using an ISCO chromatograph on silica (40 g) with ethyl acetate (0~20%)/hexanes to give the product, dibenzyl (5-(3,5-dibromophenoxy)pentane-1,4-diyl)(S)-dicarbamate, as an off white solid (1.4 g, 78% yield). ¹H NMR (CDCl₃, 300 MHz): δ 7.36 (m, 10H), 6.38 (m, 3H), 5.1 (m, 4H), 3.98 (m, 2H), 3.24 (m, 2H), 1.72 (m, 4H).

Intermediate b

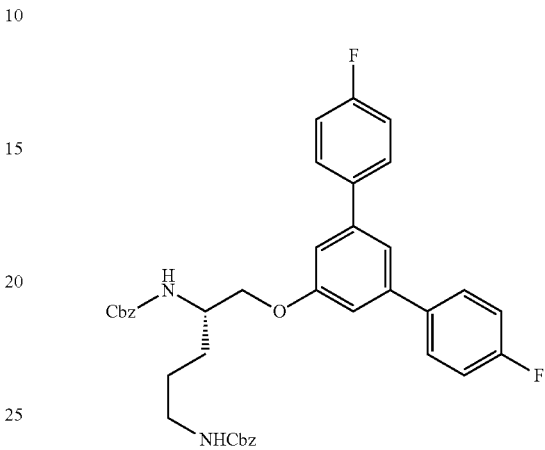

Dibenzyl (5-((4,4''-difluoro-[1,1':3',1''-terphenyl]-5'-yl)oxy)pentane-1,4-diyl)(S)-dicarbamate The mixture of (dibenzyl (5-(3,5-dibromophenoxy)pentane-1,4-diyl)(S)-dicarbamate) (0.21 g, 0.34 mmol) in 1,4-dioxane/2 N Na₂CO₃ (8 mL, 4:1), 4-fluorophenylboronic acid (0.17 g, 1.2 mmol), and tetrakis(triphenylphosphine) palladium (40 mg) was degassed with N₂ and heated to reflux for 16 hours. The reaction mixture was worked up with ethyl acetate (20 mL) and washed with brine (10 mL×2) and concentrated to give a dark paste. The paste was purified using an ISCO chromatograph on silica (24 g) with ethyl acetate (0~20%)/hexanes to give the product (dibenzyl (5-((4,4''-difluoro-[1,1':3',1''-terphenyl]-5'-yl)oxy)pentane-1,4-diyl)(S)-dicarbamate) as an off white solid (0.2 g, 90% yield). ¹H NMR (CDCl₃, 300 MHz): δ 7.59 (m, 4H), 7.25-7.34 (m, 13H), 7.12 (m, 4H), 6.28 (m, 2H), 5.08 (m, 4H), 4.08 (m, 3H), 3.24 (m, 2H), 1.72 (m, 4H).

Example 14. Preparation of (2S)-1-((4,4''-difluoro-[1,1':3',1''-terphenyl]-5'-yl)oxy)-6-methylheptane-2,5-diaminium

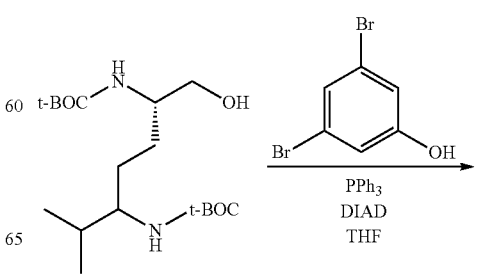

95
-continued

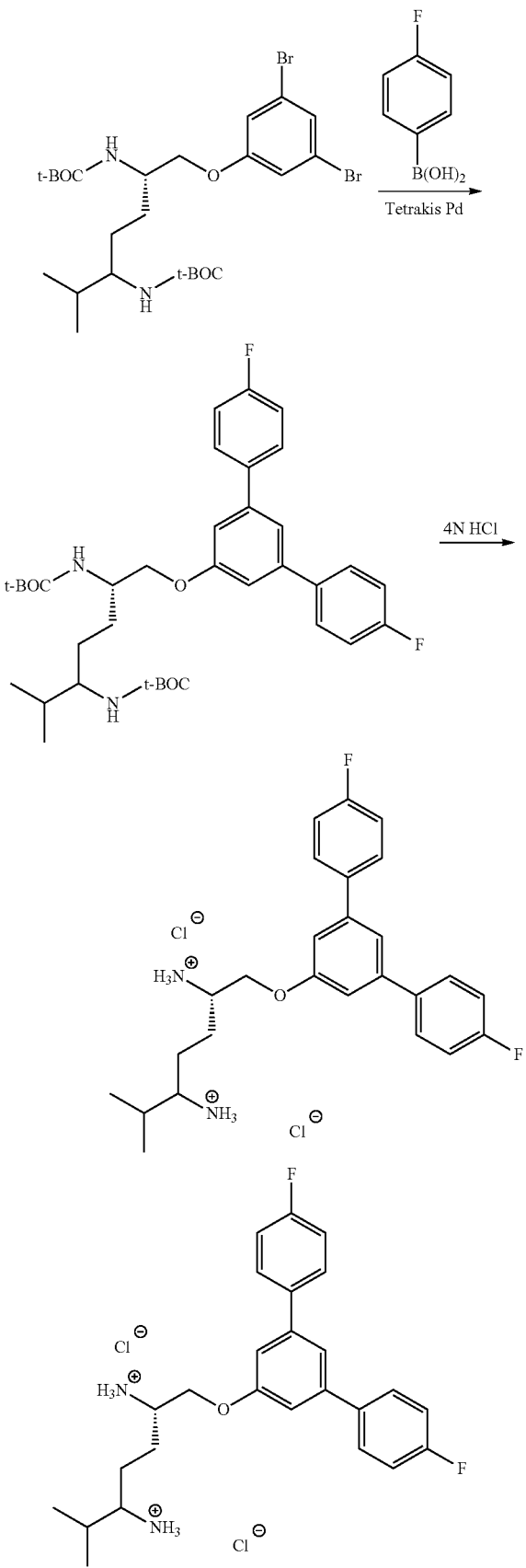

96

(2S)-1-((4,4"-Difluoro-[1,1':3',1"-terphenyl]-5'-yl)oxy)-6-methylheptane-2,5-diaminium The mixture of (di-tert-butyl ((2S)-1-((4,4"-difluoro-[1,1': 3',1"-terphenyl]-5'-yl)oxy)-6-methylheptane-2,5-diyl)dicarbamate) (0.2 g, 0.32 mmol) in DCM (2 mL), and 4 N HCl (1.2 mL) in 1,4-dioxane was stirred at room temperature for 4 hours. The solvents and excess HCl were removed, the residue was triturated with ethyl acetate/hexanes to give the product, (2S)-1-((4,4"-difluoro-[1,1':3',1"-terphenyl]-5'-yl)oxy)-6-methylheptane-2,5-diamine, as an off-white solid (0.14 g, 95% yield). $^1$H NMR (DMSO-d6, 300 MHz): δ 8.47 (m, 3H), 8.13 (m, 3H), 7.79 (m, 4H), δ 7.44 (m, 1H), δ 7.31-7.21 (m, 6H), 4.25 (m, 2H), 3.45 (m, 4H), 2.98 (m, 1H), 1.8 (m, 5H), 0.89 (m, 6H).

The requisite intermediates were prepared as described in the following paragraphs.

Intermediate a

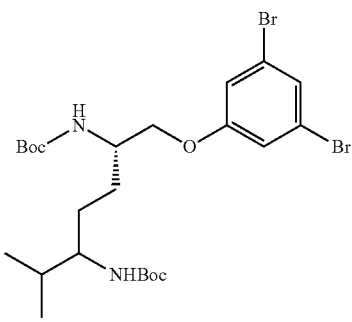 [SMILES: CC(C)C(CC[C@@H](COc1cc(Br)cc(Br)c1)NC(=O)OC(C)(C)C)NC(=O)OC(C)(C)C]

Di-tert-butyl ((2S)-1-(3,5-dibromophenoxy)-6-methylheptane-2,5-diyl)dicarbamate

The mixture of 3, 5-dibromophenol (0.42 g, 1.66 mmol) in THF, di-tert-butyl ((2S)-1-hydroxy-6-methylheptane-2,5-diyl)dicarbamate (0.5 g, 1.38 mmol), triphenylphosphine (0.44 g, 1.66 mmol), and DIAD (0.34 g, 1.66 mmol) was stirred at room temperature for 16 hours. The reaction mixture was worked up with ethyl acetate (40 mL) and washed with was washed with brine (30 mL×2) and concentrated to give a yellow paste. The paste was purified using an ISCO chromatograph on silica (24 g) with ethyl acetate (0~20%)/hexanes to give the product (di-tert-butyl ((2S)-1-(3,5-dibromophenoxy)-6-methylheptane-2,5-diyl)dicarbamate) as an off white solid (0.37 g, 47% yield). $^1$H NMR (CDCl$_3$, 300 MHz): δ 6.98 (m, 3H), 4.8 (m, 1H), 4.4 (m, 1H), 3.9 (m, 3H), 3.6 (m, 1H), 1.68 (m, 18H), 0.87 (m, 6H).

Intermediate b

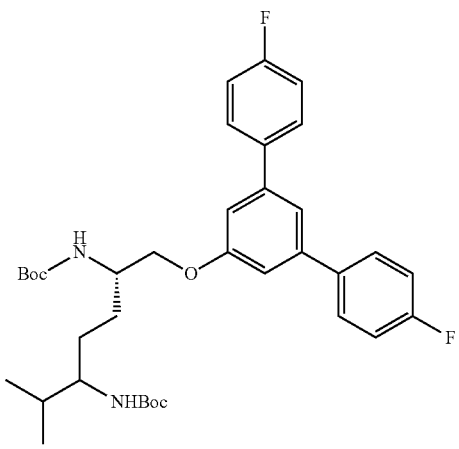 [SMILES: CC(C)C(CC[C@@H](COc1cc(-c2ccc(F)cc2)cc(-c2ccc(F)cc2)c1)NC(=O)OC(C)(C)C)NC(=O)OC(C)(C)C]

Di-tert-butyl ((2S)-1-((4,4''-difluoro-[1,1':3',1''-terphenyl]-5'-yl)oxy)-6-methylheptane-2,5-diyl)dicarbamate The mixture of (di-tert-butyl ((2S)-1-(3,5-dibromophenoxy)-6-methylheptane-2,5-diyl)dicarbamate) (0.20 g, 0.34 mmol) in 1,4-dioxane/2 N $Na_2CO_3$ (8 mL, 4:1), 4-fluorophenylboronic acid (0.17 g, 1.2 mmol), and tetrakis(triphenylphosphine)palladium (40 mg) was degassed with N2 and heated to reflux for 16 hours. The reaction mixture was worked up with ethyl acetate (20 mL) and brine (10 mL×2) and concentrated to give a dark paste. The paste was purified using an ISCO chromatograph on silica (24 g) with ethyl acetate (0~15%)/hexanes to give the product (di-tert-butyl ((2S)-1-((4,4''-difluoro-[1,1':3',1''-terphenyl]-5'-yl)oxy)-6-methylheptane-2,5-diyl)dicarbamate) as an off white solid (0.2 g, 95% yield). $^1$H NMR ($CDCl_3$, 300 MHz): δ 7.6 (m, 4H), 7.25 (m, 2H), 7.12 (m, 4H), 7.15 (m, 2H), 4.8 (m, 1H), 4.4 (m, 1H), 4.38 (m, 1H), 4.05 (m, 3H), 3.42 (m, 1H), 1.7-1.6 (m, 18H), 0.87 (m, 6H).

Example 15. Preparation of (S)—N1-([1,1':3',1''-terphenyl]-5'-ylmethyl)pentane-1,2,5-triaminium Chloride

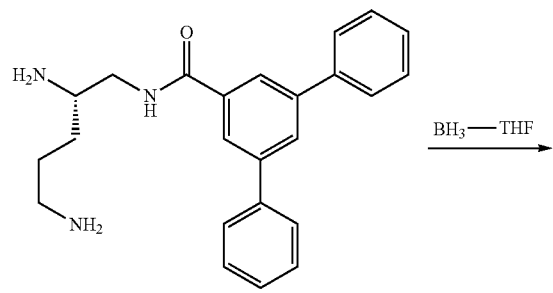

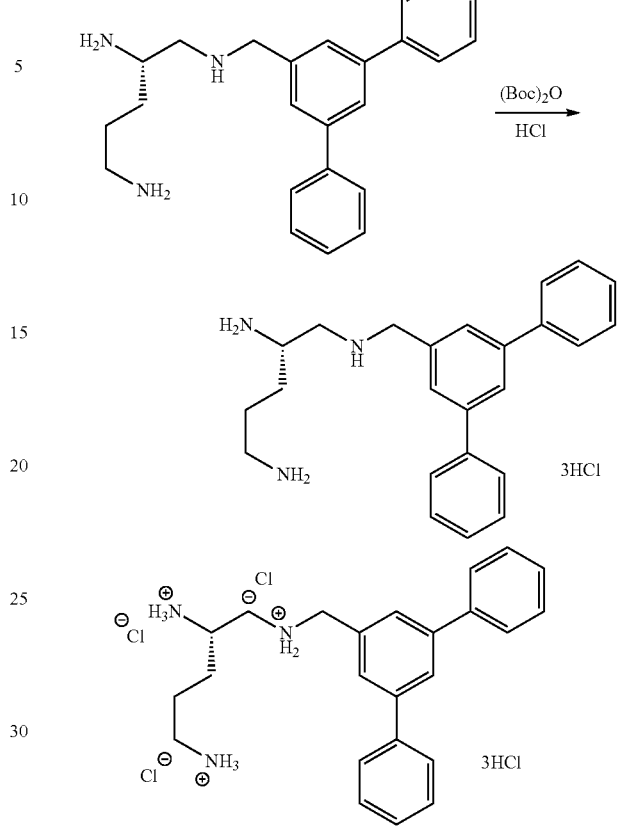

(S)—N1-([1,1':3',1''-Terphenyl]-5'-ylmethyl)pentane-1,2,5-triaminium chloride

To a solution of the amide (85 mg, 0.23 mmol) in THF (5 mL) was added $BH_3$ (1.0 M in THF (1.14 mL, 1.4 mmol), then heated to reflux for 16 hours. The reaction mixture was cooled to room temperature then added slowly with MeOH (1 mL) and water (0.2 mL), the resulting reaction mixture was heated to reflux for 2 hours. The reaction mixture was cooled to room temperature, concentrated to afford the crude amine product, which was dissolved in DCM (10 mL), followed by addition of $(Boc)_2O$ (200 mg, 0.92 mmol), $Et_3N$ (1.3 mL, 0.92 mmol). The reaction mixture was stirred at room temperature overnight. After removal of solvent, the residue was purified using an ISCO chromatograph on silica (24 g) with ethyl acetate (0~40%)/hexanes to give the boc protected product as a colorless oil. The oil was treated with 4N HCl in 1,4-dioxane (1 mL) for 4 hours. The solvent was removed and the residue was triturated with EtOAc. The solid was collected by filtration to afford the desired product as an off white solid (35 mg, 34% yield). $^1$H NMR (DMSO, 300 MHz) δ: 10.02 (br s, 2H), 8.59 (br s, 3H), 8.02 (br s, 3H), 7.93-7.80 (m, 5H), 7.52-7.40 (m, 7H), 4.35 (m, 2H), 3.80 (m, 1H), 2.82 (br s, 2H), 1.72 (m, 4H).

Example 16. Preparation of (S)-5-((4,4''-bis(trifluoromethyl)-[1,1':3',1''-terphenyl]-5'-yl)oxy)pentane-1,4-diaminium chloride

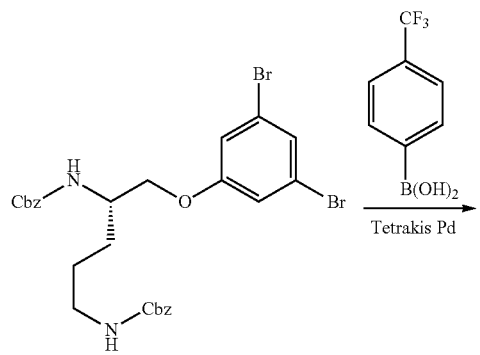

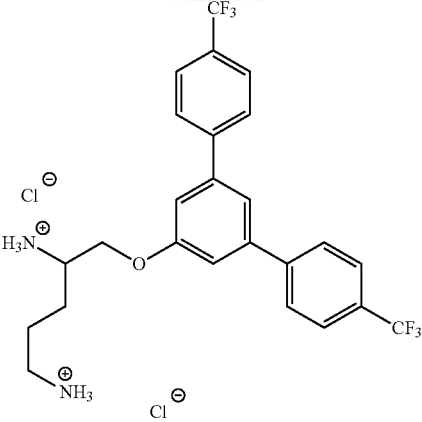

(S)-5-((4,4''-Bis(trifluoromethyl)-[1,1':3',1''-terphenyl]-5'-yl)oxy)pentane-1,4-diaminium chloride The mixture of dibenzyl (5-((4,4''-bis(trifluoromethyl)-[1,1':3',1''-terphenyl]-5'-yl)oxy)pentane-1,4-diyl)(S)-dicarbamate (0.14 g, 0.18 mmol) in MeOH (6 mL), Pd/C (30 mg) was subjected hydrogenation with $H_2$ for 16 hours. The reaction mixture was filtered from catalyst and the filtrate was concentrated to give the product as a white solid (which was isolated as the dihydrochloride salt after treatment with 4 N HCl) (85 mg, 95% yield). $^1$H NMR (CDCl$_3$, 300 MHz): δ 7.72 (m, 8H), 7.37 (s, 1H), 7.15 (m, 2H), 4.10 (m, 1H), 3.87 (m, 1H), 3.84 (m, 1H), 3.24 (m, 1H), 2.7 (m, 2H), 1.63 (m, 4H).

The requisite intermediate was prepared as described in the following paragraph.

Intermediate a

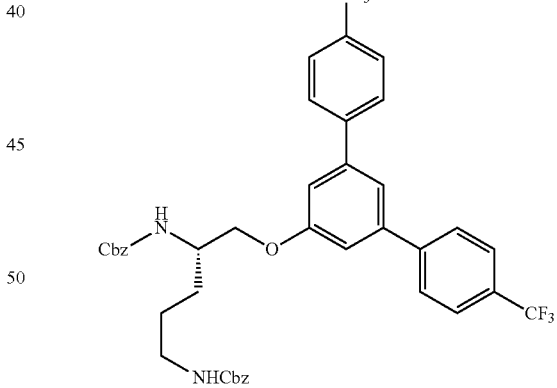

Dibenzyl (5-((4,4''-bis(trifluoromethyl)-[1,1':3',1''-terphenyl]-5'-yl)oxy)pentane-1,4-diyl)(S)-dicarbamate The mixture of (di-tert-butyl ((2S)-1-(3,5-dibromophenoxy)-6-methylheptane-2,5-diyl)dicarbamate) (0.21 g, 0.34 mmol) in 1,4-dioxane/2 N Na$_2$CO$_3$ (8 mL, 4:1), 4-trifluoromethylphenylboronic acid (0.23 g, 1.2 mmol), and tetrakis (triphenylphosphine) palladium (40 mg) was degassed with N$_2$ and heated to reflux for 16 hours. The reaction mixture was worked up with ethyl acetate (20 mL) and washed with

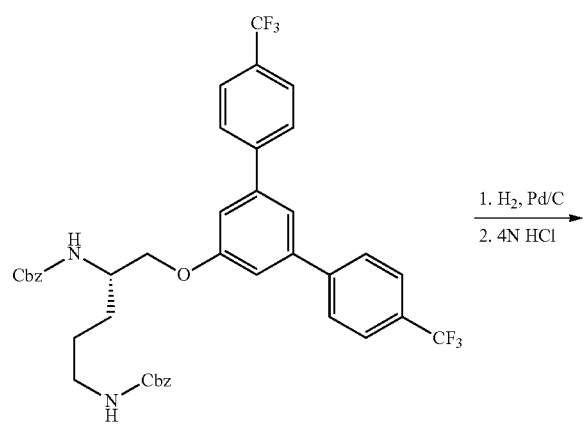

brine (10 mL×2) and concentrated to give a dark paste. The paste was purified using an ISCO chromatograph on silica (24 g) with ethyl acetate (0~20%)/hexanes to give the product, dibenzyl (5-((4,4"-bis(trifluoromethyl)-[1,1':3',1"-terphenyl]-5'-yl)oxy)pentane-1,4-diyl)(S)-dicarbamate, as an off white solid (0.22 g, 90% yield). $^1$H NMR (CDCl$_3$, 300 MHz) δ 7.74 (m, 10H), 7.3 (m, 11H), 7.18 (s, 2H), 5.14 (m, 4H), 4.10 (m, 3H), 3.30 (m, 2H), 1.70 (m, 4H).

Example 17. Preparation of (S)-5-((4,4"-dimethoxy-[1,1':3',1"-terphenyl]-5'-yl)oxy)pentane-1,4-diaminium chloride

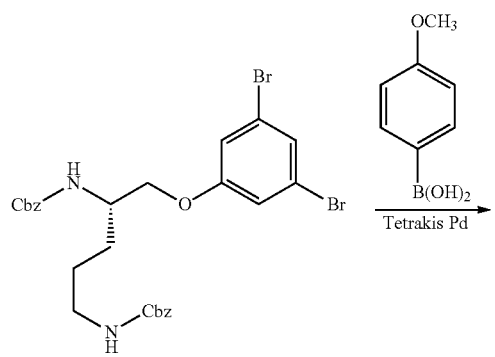

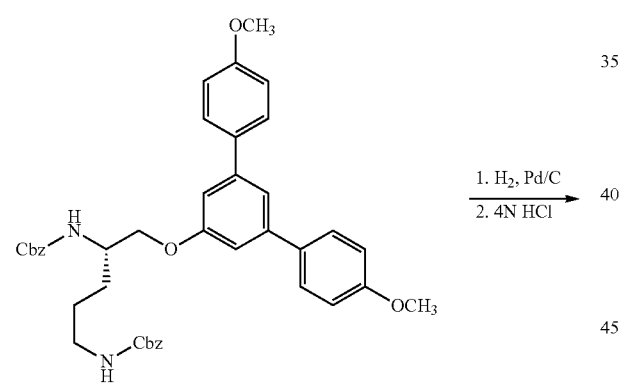

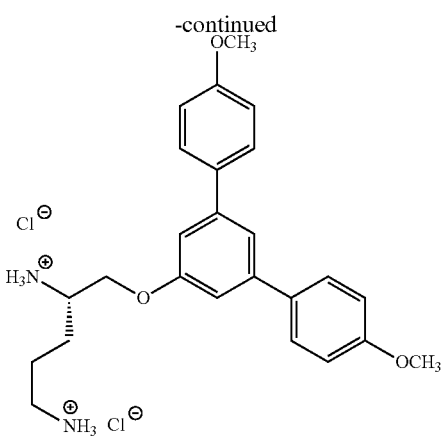

(S)-5-((4,4"-Dimethoxy-[1,1':3',1"-terphenyl]-5'-yl)oxy)pentane-1,4-diaminium chloride The mixture of (dibenzyl (5-((4,4"-dimethoxy-[1,1':3',1"-terphenyl]-5'-yl) oxy)pentane-1,4-diyl)(S)-dicarbamate) (0.10 g, 0.15 mmol) in MeOH (6 mL), Pd/C (20 mg) was-subjected hydrogenation with H$_2$ for 16 hours. The reaction mixture was filtered from catalyst and the filtrate was concentrated to give the product (which was isolated as the dihydrochloride salt after treatment with 4 N HCl), (S)-5-((4,4"-Dimethoxy-[1,1':3',1"-terphenyl]-5'-yl)oxy) pentane-1,4-diaminium chloride, as a white solid (58 mg, 94% yield). $^1$H NMR (CDCl$_3$, 300 MHz): δ 7.58-7.54 (m, 4H), 7.32 (s, 1H), 7.03-6.96 (m, 6H), 4.04 (m, 1H), 3.85-3.81 (m, 7H), 3.25 (m, 1H), 2.77 (m, 2H), 1.64 (m, 4H).

The requisite intermediate was prepared as described in the following paragraph.

Intermediate a

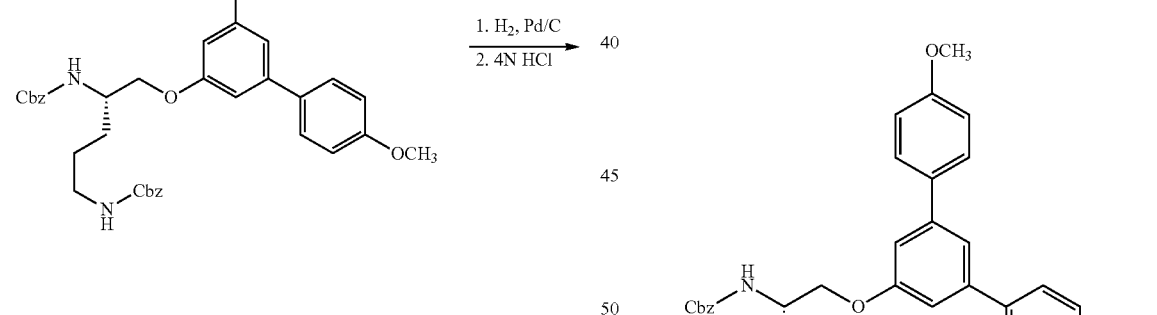

Dibenzyl (5-((4,4"-dimethoxy-[1,1':3',1"-terphenyl]-5'-yl)oxy)pentane-1,4-diyl)(S)-dicarbamate The mixture of (di-tert-butyl ((2S)-1-(3,5-dibromophenoxy)-6-methylheptane-2,5-diyl)dicarbamate) (0.2 g, 0.32 mmol) in 1,4-dioxane/2 N Na$_2$CO$_3$ (8 mL, 4:1), 4-methoxyphenylboronic acid (0.17 g, 1.1 mmol), and tetrakis(triphenylphosphine)palladium (40 mg) was degassed with N$_2$ and heated to reflux for 16 hours. The reaction mixture was worked up with ethyl acetate (20 mL) and the organic layer washed with brine (10 mL×2) and concentrated to give a dark paste. The paste was purified using an ISCO chromatograph on silica (24 g) with ethyl acetate (0~30%)/hexanes to give the product, dibenzyl (5-((4,4''-dimethoxy-[1,1':3',1''-terphenyl]-5'-yl)oxy)pentane-1,4-diyl)(S)-dicarbamate, as an off white solid (0.18 g, 85% yield). ¹H NMR (CDCl₃, 300 MHz): δ 7.60-7.57 (m, 4H), 7.38-7.34 (m, 11H), 7.03-6.99 (m, 6H), 5.13 (m, 4H), 4.10 (m, 3H), 3.93-3.89 (m, 6H), 3.25 (m, 2H), 1.68 (m, 4H)

Example 18. Preparation of (R)-5-((3,3''-difluoro-[1,1':3',1''-terphenyl]-5'-yl)oxy)pentane-1,4-diaminium chloride

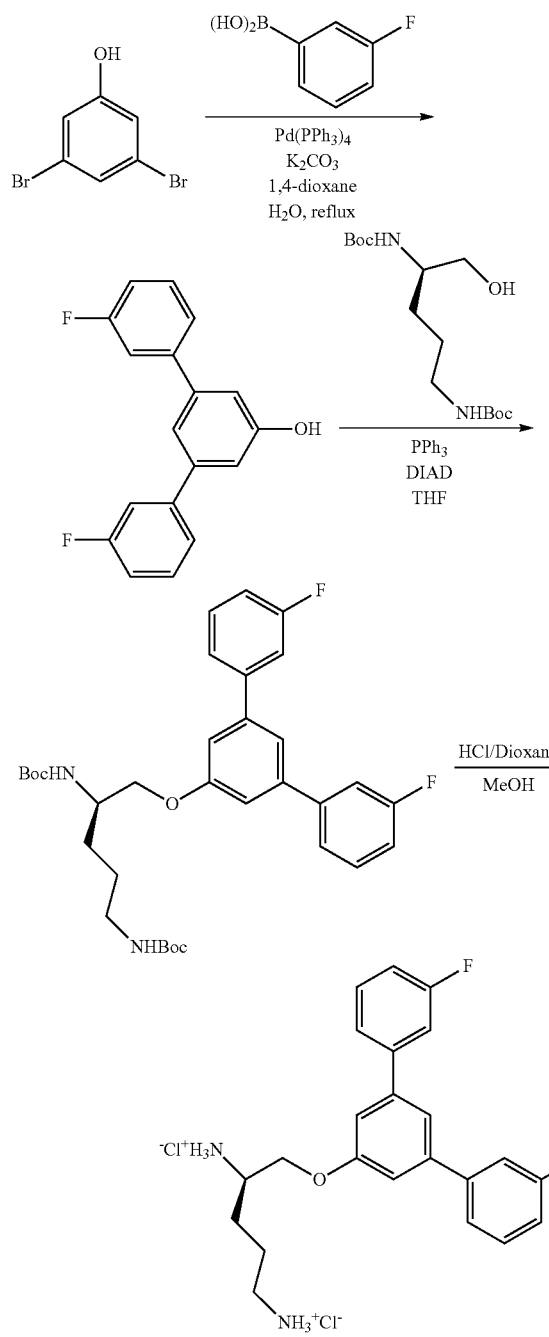

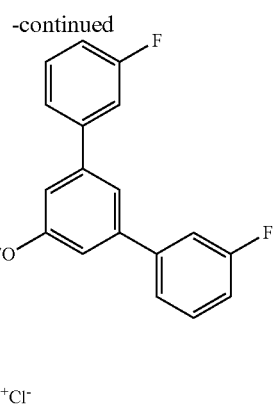

(R)-5-((3,3''-difluoro-[1,1':3',1''-terphenyl]-5'-yl)oxy)pentane-1,4-diaminium chloride To a solution of di-tert-butyl (5-((3,3''-difluoro-[1,1':3',1''-terphenyl]-5'-yl)oxy)pentane-1,4-diyl)(R)-dicarbamate (100 mg, 0.18 mmol) in MeOH (3 ml) was added 0.5 ml 4N HCl in dioxane. The reaction was stirred at room temperature overnight. The residue was concentrated and triturated with EtOAc to afford product (55 mg, 71% yield) as a white solid. ¹H NMR (300 MHz, DMSO) δ 8.88-8.20 (m, 6H), 7.69-7.62 (m, 5H), 7.55-7.48 (m, 2H), 7.35 (m, 2H), 7.26-7.19 (m, 2H), 4.39-4.19 (m, 3H), 2.83-2.78 (m, 2H), 1.96-1.76 (m, 4H).

The requisite intermediates were prepared as described in the following paragraphs.

Step 1)

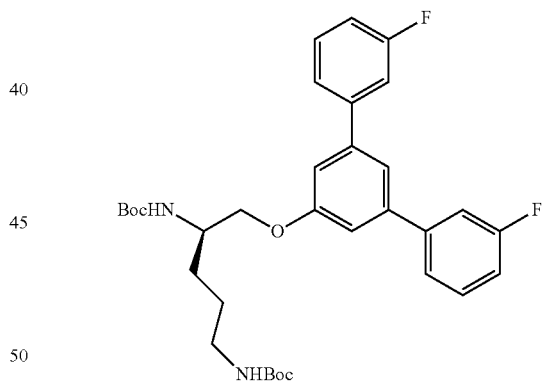

di-tert-butyl (5-((3,3''-difluoro-[1,1':3',1''-terphenyl]-5'-yl)oxy)pentane-1,4-diyl)(R)-dicarbamate Triphenylphosphine (114 mg, 0.44 mmol) and 3,3''-difluoro-[1,1':3',1''-terphenyl]-5'-ol (100 mg, 0.36 mmol) were added to a flask containing dry THF (10 mL). Di-tert-butyl (5-hydroxypentane-1,4-diyl)(R)-dicarbamate (134 mg, 0.44 mmol) was added and the flask was cooled to 0° C. DIAD (87 mg, 0.44 mmol) was added dropwise and reaction allowed to stir for 30 minutes at 0° C. and overnight at room temperature. The mixture was concentrated under reduced pressure and residue purified using an ISCO chromatograph with silica (0-100% ethyl acetate/hexane) to give product as a colorless oil. (100 mg, 48%); ¹H NMR (CDCl₃) (300

MHz) δ 7.60-7.43 (m, 6H), 7.26-7.21 (m, 3H), 7.01-6.60 (m, 4H), 4.93-4.91 (m, 1H), 4.25-4.23 (m, 2H) 3.37-3.33 (m, 2H), 1.88-1.72 (m, 4H), 1.60-1.52 (m, 9H), 1.44-1.39 (m, 9H).

Step 2)

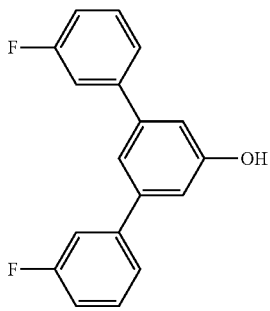 [SMILES: Oc1cc(-c2cccc(F)c2)cc(-c2cccc(F)c2)c1]

3,3''-difluoro-[1,1':3',1''-terphenyl]-5'-ol

The mixture of 3,5-dibromophenol (500 mg, 1.99 mmol), (3-fluorophenyl)boronic acid (834 mg, 5.96 mmol), $K_2CO_3$ (824 mg, 5.96 mmol) in a mixture of 1,4-dioxane, $H_2O$ solution (20/5 mL) was degassed and $Pd(PPh_3)_4$ (115 mg, 0.10 mmol) was added. The reaction mixture was heated at 100° C. overnight and it was extracted with EtOAc and washed with brine and concentrated. Then it was purified by column chromatography on silica gel (0-30% ethyl acetate/hexanes) to give the product (472 mg, 84% yield) as a white solid. $^1$H NMR (300 MHz, $CDCl_3$) δ 7.36-7.18 (m, 7H), 7.06-6.95 (m, 4H), 5.03 (s, 1H).

Example 19. Preparation of (R)-5-((3,3'',4,4''-tetrafluoro-[1,1':3',1''-terphenyl]-5'-yl)oxy)pentane-1,4-diaminium chloride

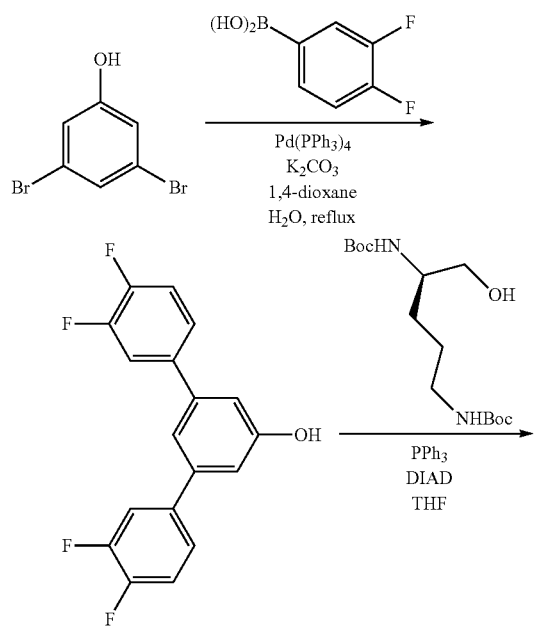

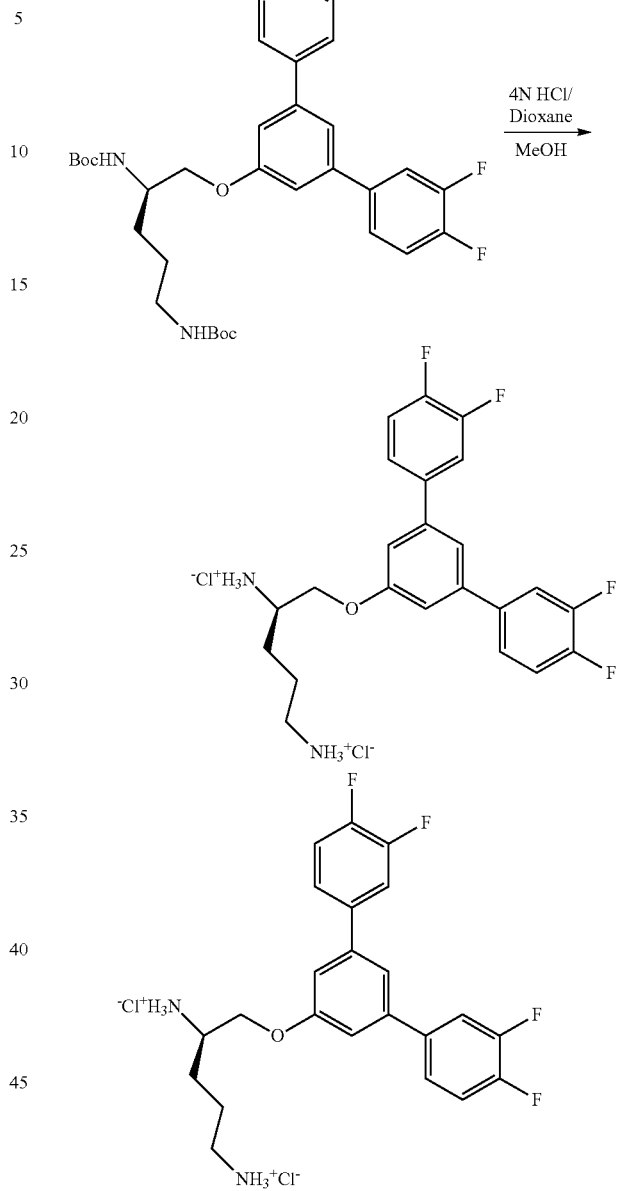

(R)-5-((3,3'',4,4''-tetrafluoro-[1,1':3',1''-terphenyl]-5'-yl)oxy)pentane-1,4-diaminium chloride To a solution of di-tert-butyl (5-((3,3'',4,4''-tetrafluoro-[1,1':3',1''-terphenyl]-5'-yl)oxy)pentane-1,4-diyl)(R)-dicarbamate (94 mg, 0.15 mmol) in MeOH (3 ml) was added 0.5 ml 4N HCl in dioxane. The reaction was stirred at room temperature overnight. The residue was concentrated and triturated with EtOAc to afford product (51 mg, 68% yield) as a white solid. $^1$H NMR (300 MHz, DMSO) δ 8.51-8.15 (m, 6H), 7.99-7.92 (m, 2H), 7.65-7.48 (m, 5H), 7.35 (m, 2H), 4.39-4.21 (m, 3H), 2.81 (m, 2H), 1.85-1.68 (m, 4H).

The requisite intermediates were prepared as described in the following paragraphs.

Step 1)

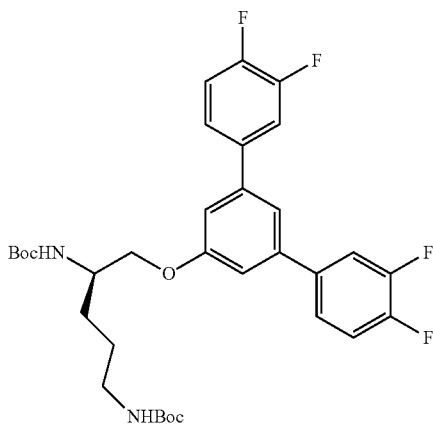 [SMILES: CC(C)(C)OC(=O)NCCC[C@H](COc1cc(-c2ccc(F)c(F)c2)cc(-c2ccc(F)c(F)c2)c1)NC(=O)OC(C)(C)C]

di-tert-butyl (5-((3,3",4,4"-tetrafluoro-[1,1':3',1"-terphenyl]-5'-yl)oxy)-pentane-1,4-diyl)(R)-dicarbamate Triphenylphosphine (100 mg, 0.38 mmol) and 3,3",4,4"-tetrafluoro-[1,1':3',1"-terphenyl]-5'-ol (100 mg, 0.32 mmol) were added to a flask containing dry THF (10 mL). Di-tert-butyl (5-hydroxypentane-1,4-diyl)(R)-dicarbamate (120 mg, 0.38 mmol) was added and the flask was cooled to 0° C. DIAD (77 mg, 0.38 mmol) was added dropwise and reaction allowed to stir for 30 minutes at 0° C. and overnight at room temperature. The mixture was concentrated under reduced pressure and residue purified using an ISCO chromatograph with silica (0-100% ethyl acetate/hexane) to give product as a colorless oil. (94 mg, 47%); $^1$H NMR (CDCl$_3$) (300 MHz) δ 7.47-7.24 (m, 7H), 7.08 (m, 2H), 6.76 (m, 2H), 4.78 (m, 1H), 4.09 (m, 2H) 3.20-3.18 (m, 2H), 1.75-1.58 (m, 4H), 1.47-1.45 (m, 9H), 1.33-1.25 (m, 9H).

Step 2)

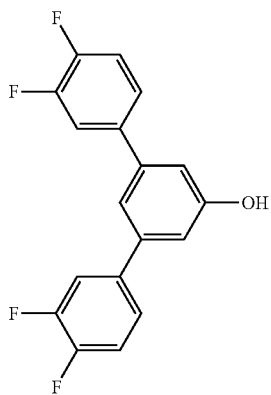 [SMILES: Oc1cc(-c2ccc(F)c(F)c2)cc(-c2ccc(F)c(F)c2)c1]

3,3",4,4"-tetrafluoro-[1,1':3',1"-terphenyl]-5'-ol

The mixture of 3,5-dibromophenol (500 mg, 1.99 mmol), (3,4-difluorophenyl)boronic acid (942 mg, 5.96 mmol), K$_2$CO$_3$ (823 mg, 5.96 mmol) in a mixture of 1,4-dioxane, H$_2$O solution (20/5 mL) was degassed and Pd(PPh$_3$)$_4$ (115 mg, 0.10 mmol) was added. The reaction mixture was heated at 100° C. overnight and it was extracted with EtOAc and washed with brine and concentrated. Then it was purified by column chromatography on silica gel (0-30% ethyl acetate/hexanes) to give the product (563 mg, 89% yield) as a white solid. $^1$H NMR (300 MHz, CDCl$_3$) δ 7.36-7.13 (m, 6H), 6.99-6.93 (m, 2H), 6.64-6.44 (m, 1H), 5.00 (s, 1H).

Example 20. Description of Test Methods

Test A. Minimum Inhibitory Concentration (MIC)-Based Assay for Potentiation of Antibiotics that are Known Efflux Pump Substrates:

MIC-based assays were used to evaluate the impact of potential efflux pump inhibiting (EPI) compounds on the MICs of antibiotics (e.g., clarithromycin and levofloxacin) known to be substrates for Gram-negative bacterial efflux pumps. The assays were conducted in accordance with Clinical and Laboratory Standards Institute (CLSI) guidelines for broth microdilution, with the modification that assays were conducted in the presence and absence of the test EPI compounds. When present, the EPI compounds were added to cation-adjusted Mueller-Hinton (CAMH) broth (Becton, Dickinson and Co., Franklin Lakes, N.J.) at a final concentration in the range of 1.6 to 12.5 g/mL.

Log-phase Gram-negative bacteria were added to 96-well microtiter plates (at 5×10$^5$ colony forming units (CFU) per mL) containing two-fold serial dilutions of antibiotic in CAMH broth either in the absence or presence of the test EPI compounds. In all assays, each serial dilution of antibiotic was present in duplicate. The final volume in each well was 0.1 mL, and the microtiter plates were incubated aerobically for 24 hours at 37° C. Bacterial growth was then monitored by measuring the optical density (OD) at 600 nm using a VersaMax® plate reader (Molecular Devices, Inc., Sunnyvale, Calif.), with the MIC being defined as the lowest compound concentration at which growth was >90% inhibited compared to antibiotic-free control. The following Gram-negative bacterial strains were included in these assays:
*Escherichia coli* ATCC 25922
*Klebsiella pneumoniae* ATCC 13883 and ATCC 10031
*Pseudomonas aeruginosa* ATCC 27853.

Test B. Fluorescence-Based Cellular Assay for Efflux Inhibition:

The impact of potential EPI compounds on the activity of efflux pumps was also evaluated with a fluorescence-based cellular assay that measures the efflux of Hoechst 33342, a known substrate of Gram-negative bacterial efflux pumps. When bound to intracellular bacterial DNA, Hoechst 33342 fluoresces brightly, while the unbound fluorophore outside the bacterial cell exhibits little or no fluorescence. Thus, the efflux of Hoechst 33342 from inside to outside the bacterial cell is associated with a substantive decrease in fluorescence.

Bacterial cells were harvested from overnight cultures by centrifugation, and the cell pellet was washed with phosphate-buffered containing 1 mM MgCl$_2$ (PBSM). After washing the cells, the cell pellets were resuspended in PBSM to achieve a final OD at 600 nm of 0.6 to 0.9. The ATP required for efflux pump function was then depleted by addition of carbonyl cyanide 3-chlorophenylhydrazone (CCCP) to a final concentration in the range of 3 to 10 μM. Hoechst 33342 was then added to a final concentration of 10 M, and the cells were incubated aerobically at 37° C. for 0.5 to 18 hours. The bacterial suspension (200 μL) was added to wells of a black, flat-bottom 96-well plate containing test EPI compounds at concentrations of ranging from 1.6 to 25 μg/mL or an equivalent volume of the vehicle (DMSO) alone. A plate vortexer was used to mix the bacterial cells with the test EPI compounds, and the plates are pre-incubated at 37° C. for 5 minutes. After the pre-incubation, Hoechst 33342 efflux was initiated by addition of glucose to a final concentration of 10 to 50 mM. A SpectraMax® 2 fluorescent plate reader (Molecular Devices, Inc., Sunnyvale, Calif.) was used to monitor the fluorescence of each well at 37° C. once per minute for 20 to 60 minutes. The excitation and emission wavelengths were set at 355 and 460 nm, respectively. *E. coli* ATCC 25922, *K. pneumoniae* ATCC 13883, and *P. aeruginosa* ATCC 27853 were used as model Gram-negative bacterial strains in this assay.

Example 21

The following can illustrate representative pharmaceutical dosage forms, containing a compound of formula I ('Compound X') or a pharmaceutically acceptable salt thereof, for therapeutic or prophylactic use in humans. The tablets can optionally comprise an enteric coating.

| (i) Tablet 1 | mg/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/mL |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/mL |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 1.0N Sodium hydroxide solution (pH adjustment to 7.0-7.5) | q.s. |
| Water for injection | q.s. ad 1 mL |

| (vi) Aerosol | mg/can |
|---|---|
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

The invention claimed is:

1. A compound of formula I:

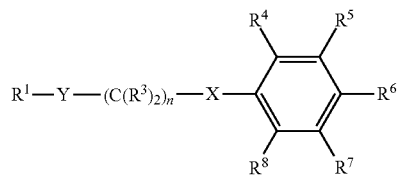

wherein:
X is —O—, Y is —C(H)(NR$^{b1}$R$^{c1}$) and n is 1;
R$^1$ is (C$_2$-C$_8$)alkyl substituted with two or more groups independently selected from —NR$^{b2}$R$^{c2}$;
each R$^2$ is independently hydrogen, halo or (C$_1$-C$_4$)alkyl;
each R$^3$ is independently hydrogen, halo or (C$_1$-C$_4$)alkyl;
R$^4$ is hydrogen, halo, (C$_1$-C$_6$)alkyl, (C$_1$-C$_6$)haloalkyl, (C$_1$-C$_6$)alkoxy, (C$_1$-C$_4$)haloalkoxy, aryl or heteroaryl wherein the aryl or heteroaryl is optionally substituted with one or more groups independently selected from halo, (C$_1$-C$_4$)alkyl, (C$_1$-C$_4$)haloalkyl, (C$_1$-C$_4$)alkoxy and (C$_1$-C$_4$)haloalkoxy;
R$^5$ is hydrogen, halo, (C$_1$-C$_6$)alkyl, (C$_1$-C$_6$)haloalkyl, (C$_1$-C$_6$)alkoxy, (C$_1$-C$_4$)haloalkoxy, aryl or heteroaryl wherein the aryl or heteroaryl is optionally substituted with one or more groups independently selected from halo, (C$_1$-C$_4$)alkyl, (C$_1$-C$_4$)haloalkyl, (C$_1$-C$_4$)alkoxy and (C$_1$-C$_4$)haloalkoxy;
R$^6$ is hydrogen;
R$^7$ is hydrogen, halo, (C$_1$-C$_6$)alkyl, (C$_1$-C$_6$)haloalkyl, (C$_1$-C$_6$)alkoxy, (C$_1$-C$_4$)haloalkoxy, aryl or heteroaryl wherein the aryl or heteroaryl is optionally substituted with one or more groups independently selected from halo, (C$_1$-C$_4$)alkyl, (C$_1$-C$_4$)haloalkyl, (C$_1$-C$_4$)alkoxy and (C$_1$-C$_4$)haloalkoxy;
R$^8$ is hydrogen, halo, (C$_1$-C$_6$)alkyl, (C$_1$-C$_6$)haloalkyl, (C$_1$-C$_6$)alkoxy, (C$_1$-C$_4$)haloalkoxy, aryl or heteroaryl wherein the aryl or heteroaryl is optionally substituted with one or more groups independently selected from halo, $(C_1-C_4)$alkyl, $(C_1-C_4)$haloalkyl, $(C_1-C_4)$alkoxy and $(C_1-C_4)$haloalkoxy;

$R^{b1}$ and $R^{c1}$ are each independently hydrogen or $(C_1-C_4)$alkyl; and each $R^{b2}$ and $R^{c2}$ is independently hydrogen or $(C_1-C_4)$alkyl;

or a salt thereof.

2. The compound of claim 1, wherein $R^4$ is hydrogen.

3. The compound of claim 1, wherein $R^8$ is hydrogen.

4. A compound of formula I:

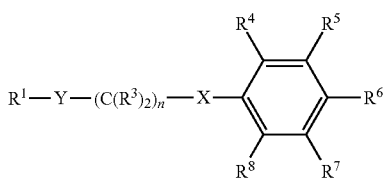

wherein:

X is —O—, Y is —C(H)($NR^{b1}R^{c1}$)— and n is 1;

$R^1$ is $(C_1-C_8)$alkyl substituted with one or more groups selected from —$NR^{b2}R^{c2}$, —$NHNH_2$, —C(—$NR^{a2}$)($NR^{b2}R^{c2}$), —$NR^{a2}$C(—$NR^{a2}$)($R^{d2}$) and —$NR^{a2}$C(—$NR^{a2}$)($NR^{b2}R^{c2}$);

each $R^2$ is independently hydrogen, halo or $(C_1-C_4)$alkyl;

each $R^3$ is independently hydrogen, halo or $(C_1-C_4)$alkyl;

$R^4$ is hydrogen, halo, $(C_1-C_6)$alkyl, $(C_1-C_6)$haloalkyl, $(C_1-C_6)$alkoxy, $(C_1-C_4)$haloalkoxy, aryl or heteroaryl wherein the aryl or heteroaryl is optionally substituted with one or more groups independently selected from halo, $(C_1-C_4)$alkyl, $(C_1-C_4)$haloalkyl, $(C_1-C_4)$alkoxy and $(C_1-C_4)$haloalkoxy;

$R^5$ is $(C_1-C_6)$alkyl, $(C_1-C_6)$haloalkyl, or phenyl wherein phenyl is optionally substituted with one or more groups independently selected from halo, $(C_1-C_4)$alkyl, $(C_1-C_4)$haloalkyl, $(C_1-C_4)$alkoxy and $(C_1-C_4)$haloalkoxy;

$R^6$ is hydrogen, halo, $(C_1-C_6)$alkyl, $(C_1-C_6)$haloalkyl, $(C_1-C_6)$alkoxy, $(C_1-C_4)$haloalkoxy, aryl or heteroaryl wherein the aryl or heteroaryl is optionally substituted with one or more groups independently selected from halo, $(C_1-C_4)$alkyl, $(C_1-C_4)$haloalkyl, $(C_1-C_4)$alkoxy and $(C_1-C_4)$haloalkoxy;

$R^7$ is hydrogen, halo, $(C_1-C_6)$alkyl, $(C_1-C_6)$haloalkyl, $(C_1-C_6)$alkoxy, $(C_1-C_4)$haloalkoxy, aryl or heteroaryl wherein the aryl or heteroaryl is optionally substituted with one or more groups independently selected from halo, $(C_1-C_4)$alkyl, $(C_1-C_4)$haloalkyl, $(C_1-C_4)$alkoxy and $(C_1-C_4)$haloalkoxy;

$R^8$ is hydrogen, halo, $(C_1-C_6)$alkyl, $(C_1-C_6)$haloalkyl, $(C_1-C_6)$alkoxy, $(C_1-C_4)$haloalkoxy, aryl or heteroaryl wherein the aryl or heteroaryl is optionally substituted with one or more groups independently selected from halo, $(C_1-C_4)$alkyl, $(C_1-C_4)$haloalkyl, $(C_1-C_4)$alkoxy and $(C_1-C_4)$haloalkoxy;

$R^{b1}$ and $R^{c1}$ are each independently hydrogen or $(C_1-C_4)$alkyl;

each $R^{a2}$ is independently hydrogen or $(C_1-C_4)$alkyl;

each $R^{b2}$ and $R^{c2}$ is independently hydrogen or $(C_1-C_4)$alkyl; and $R^{d2}$ is $(C_1-C_3)$alkyl;

or a salt thereof.

5. The compound of claim 1, wherein $R^5$ is tert-butyl, —$CF_3$, phenyl, 4-trifluoromethylphenyl, 4-fluorophenyl, 4-methoxyphenyl, 3-fluorophenyl, or 3,4-difluorophenyl.

6. A compound of formula I:

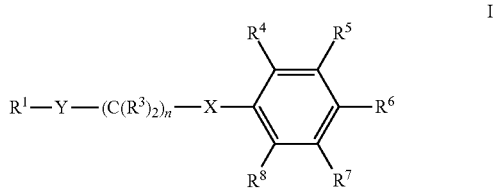

wherein:

X is —O—, Y is —C(H)($NR^{b1}R^{c1}$) and n is 1;

$R^1$ is $(C_1-C_8)$alkyl substituted with one or more groups selected from —$NR^{b2}R^{c2}$, —$NHNH_2$, —C(—$NR^{a2}$)($NR^{b2}R^{c2}$), —$NR^{a2}$C(—$NR^{a2}$)($R^{d2}$) and —$NR^{a2}$C(—$NR^{a2}$)($NR^{b2}R^{c2}$);

each $R^2$ is independently hydrogen, halo or $(C_1-C_4)$alkyl;

each $R^3$ is independently hydrogen, halo or $(C_1-C_4)$alkyl;

$R^4$ is hydrogen, halo, $(C_1-C_6)$alkyl, $(C_1-C_6)$haloalkyl, $(C_1-C_6)$alkoxy, $(C_1-C_4)$haloalkoxy, aryl or heteroaryl wherein the aryl or heteroaryl is optionally substituted with one or more groups independently selected from halo, $(C_1-C_4)$alkyl, $(C_1-C_4)$haloalkyl, $(C_1-C_4)$alkoxy and $(C_1-C_4)$haloalkoxy;

$R^5$ is hydrogen, halo, $(C_1-C_6)$alkyl, $(C_1-C_6)$haloalkyl, $(C_1-C_6)$alkoxy, $(C_1-C_4)$haloalkoxy, aryl or heteroaryl wherein the aryl or heteroaryl is optionally substituted with one or more groups independently selected from halo, $(C_1-C_4)$alkyl, $(C_1-C_4)$haloalkyl, $(C_1-C_4)$alkoxy and $(C_1-C_4)$haloalkoxy;

$R^6$ is hydrogen, halo, $(C_1-C_6)$alkyl, $(C_1-C_6)$haloalkyl, $(C_1-C_6)$alkoxy, $(C_1-C_4)$haloalkoxy, aryl or heteroaryl wherein the aryl or heteroaryl is optionally substituted with one or more groups independently selected from halo, $(C_1-C_4)$alkyl, $(C_1-C_4)$haloalkyl, $(C_1-C_4)$alkoxy and $(C_1-C_4)$haloalkoxy;

$R^7$ is $(C_1-C_6)$alkyl, $(C_1-C_6)$haloalkyl, or phenyl wherein phenyl is optionally substituted with one or more groups independently selected from halo, $(C_1-C_4)$alkyl, $(C_1-C_4)$haloalkyl, $(C_1-C_4)$alkoxy and $(C_1-C_4)$haloalkoxy;

$R^8$ is hydrogen, halo, $(C_1-C_6)$alkyl, $(C_1-C_6)$haloalkyl, $(C_1-C_6)$alkoxy, $(C_1-C_4)$haloalkoxy, aryl or heteroaryl wherein the aryl or heteroaryl is optionally substituted with one or more groups independently selected from halo, $(C_1-C_4)$alkyl, $(C_1-C_4)$haloalkyl, $(C_1-C_4)$alkoxy and $(C_1-C_4)$haloalkoxy;

$R^{b1}$ and $R^{c1}$ are each independently hydrogen or $(C_1-C_4)$alkyl;

each $R^{a2}$ is independently hydrogen or $(C_1-C_4)$alkyl;

each $R^{b2}$ and $R^{c2}$ is independently hydrogen or $(C_1-C_4)$alkyl; and $R^{d2}$ is $(C_1-C_3)$alkyl;

or a salt thereof.

7. The compound of claim 1, wherein $R^7$ is tert-butyl, —$CF_3$, phenyl, 4-trifluoromethylphenyl, 4-fluorophenyl, 4-methoxyphenyl, 3-fluorophenyl, or 3,4-difluorophenyl.

8. The compound of claim 1, wherein the moiety:
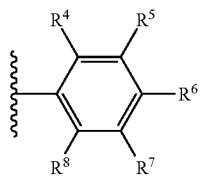
of the compound of formula I is:
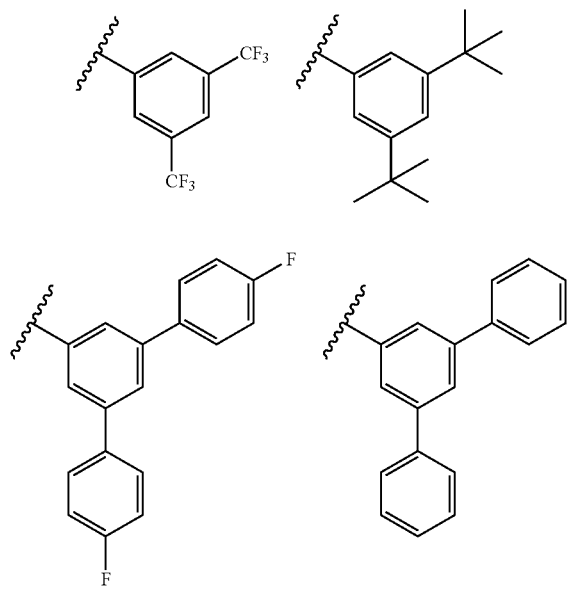
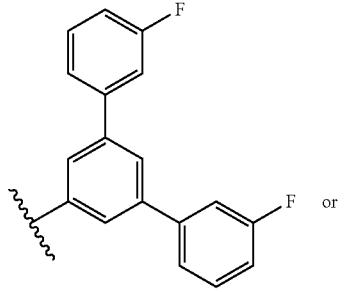
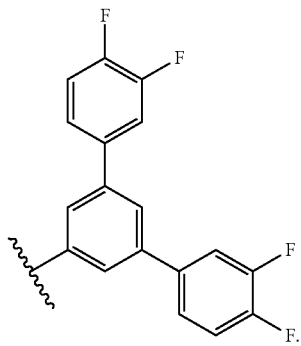
9. The compound of claim 1, wherein the moiety:
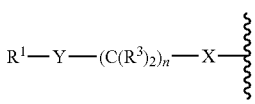
of the compound of formula I is:
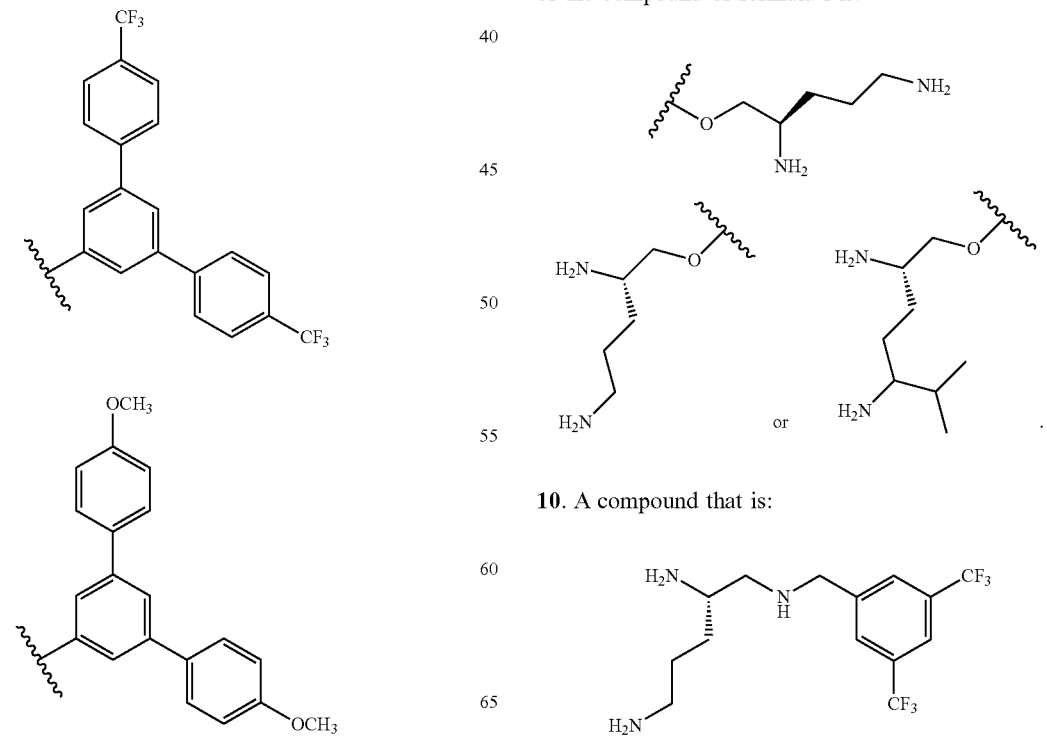
10. A compound that is:
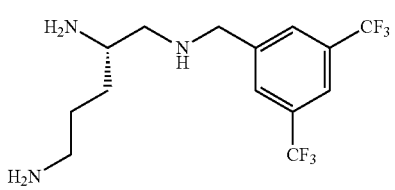

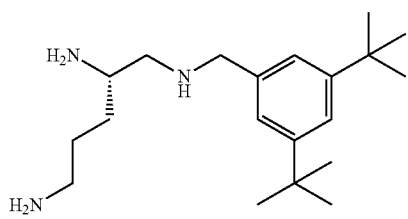
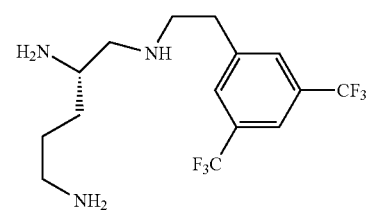
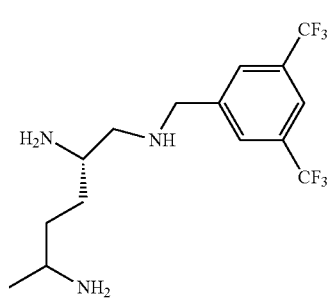
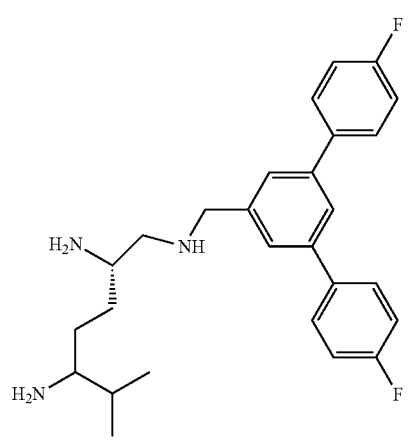
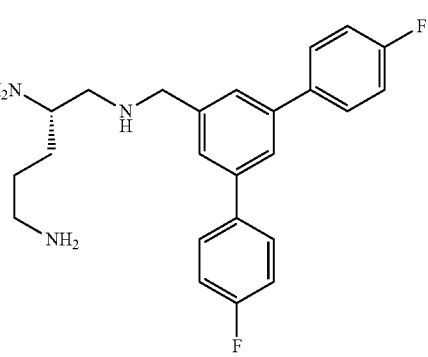
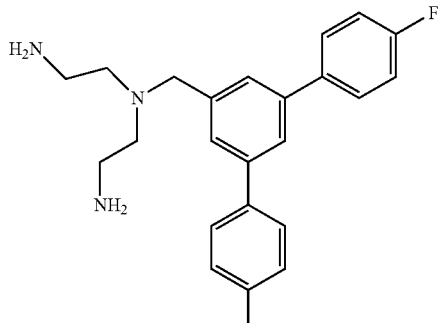
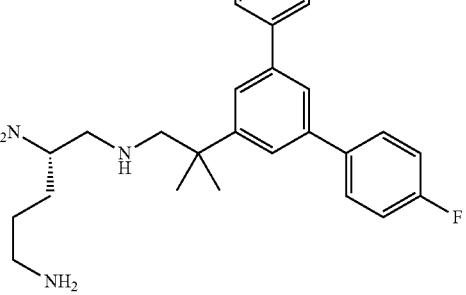
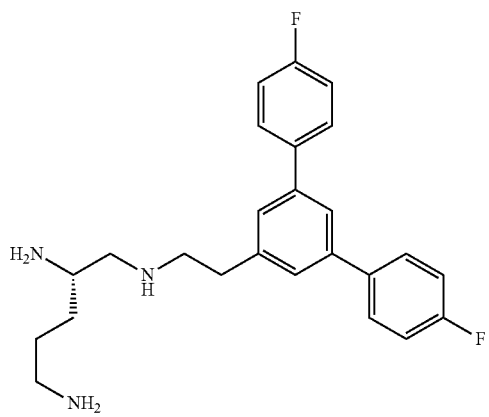
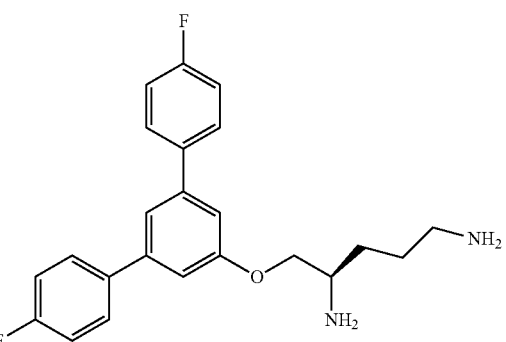

117
-continued
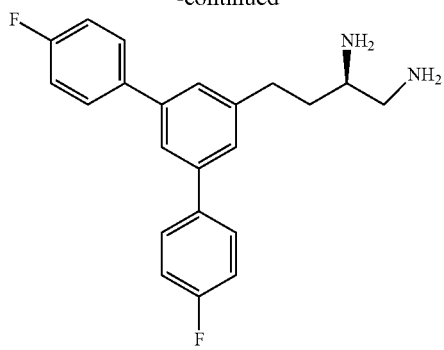
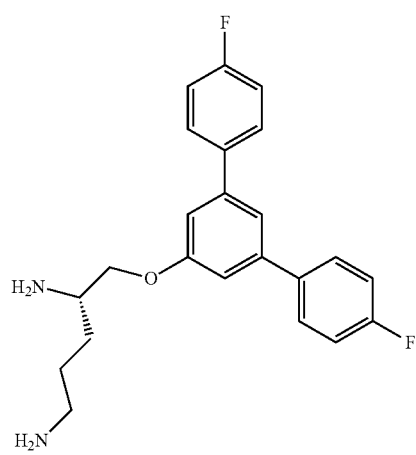
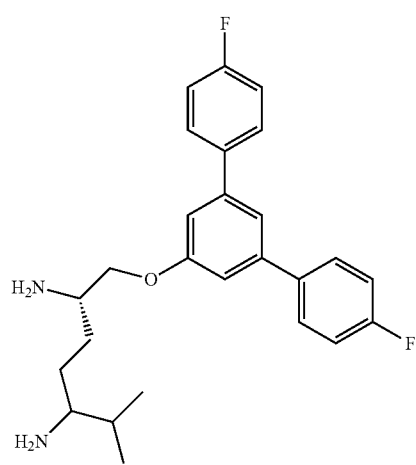
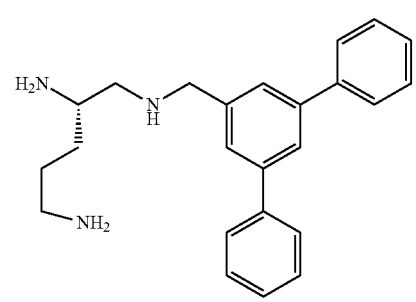
118
-continued
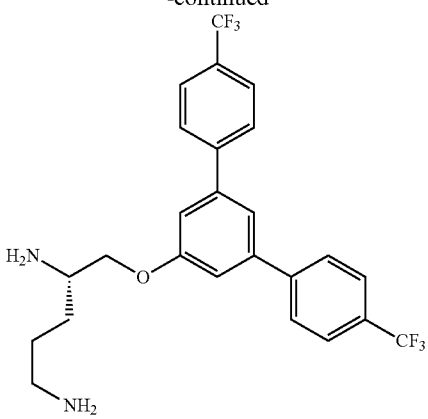
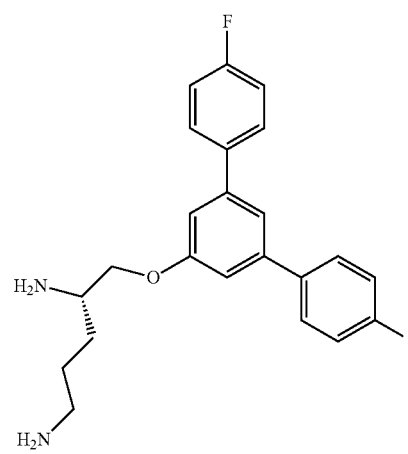
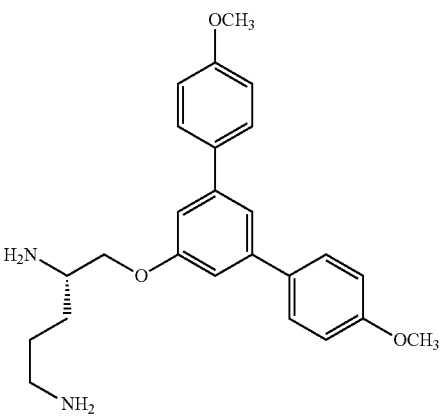
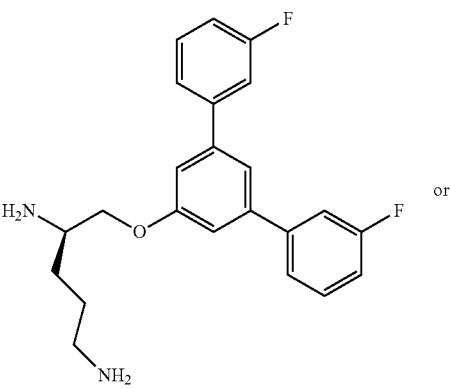 or

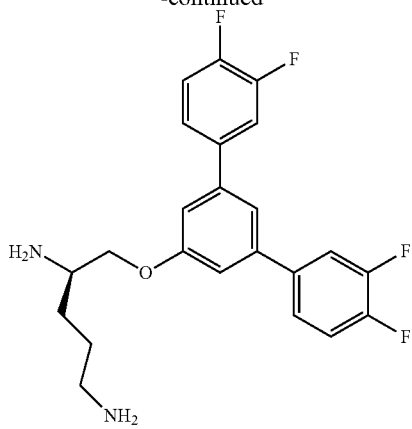

or a salt thereof.

11. A pharmaceutical composition comprising a compound as described in claim 1 or a pharmaceutically acceptable salt thereof, and a pharmaceutically acceptable vehicle.

12. A pharmaceutical composition comprising a compound as described in claim 1 or a pharmaceutically acceptable salt thereof one or more antibacterial agents and a pharmaceutically acceptable vehicle.

13. A method of inhibiting a bacterial efflux pump in an animal comprising administering to the animal a compound as described in claim 1 or a pharmaceutically acceptable salt thereof.

14. A method of treating or preventing a bacterial infection in an animal comprising co-administering to the animal a compound as described in claim 1 or a pharmaceutically acceptable salt thereof and one or more antibacterial agents.

15. The compound of claim 1 that is:

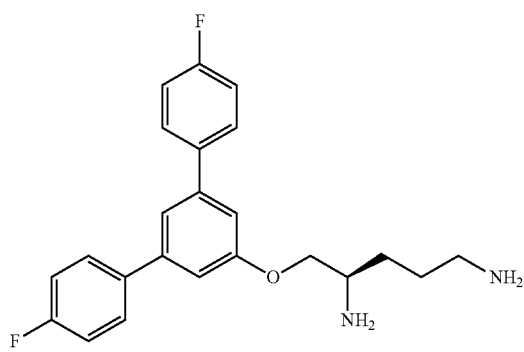

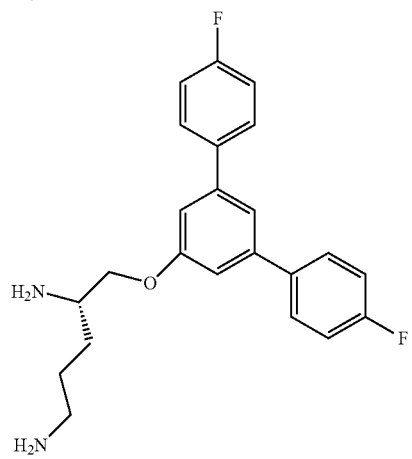

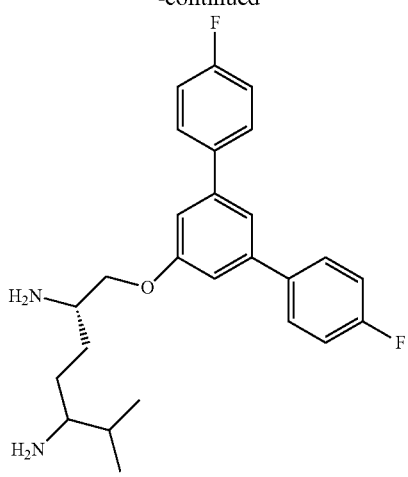

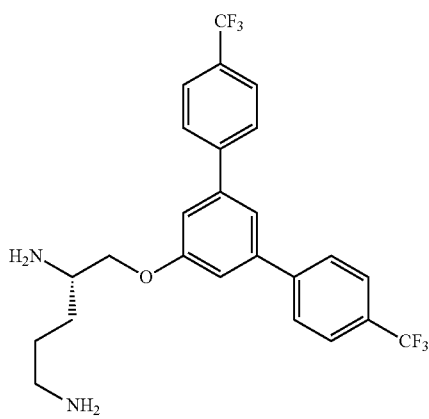

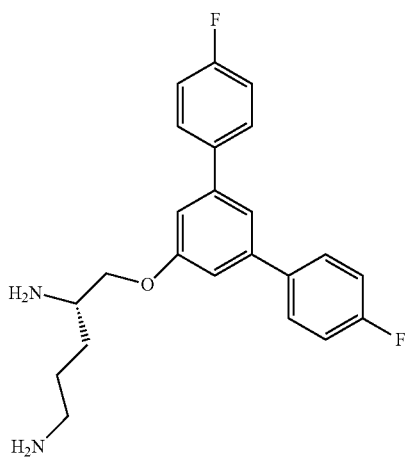

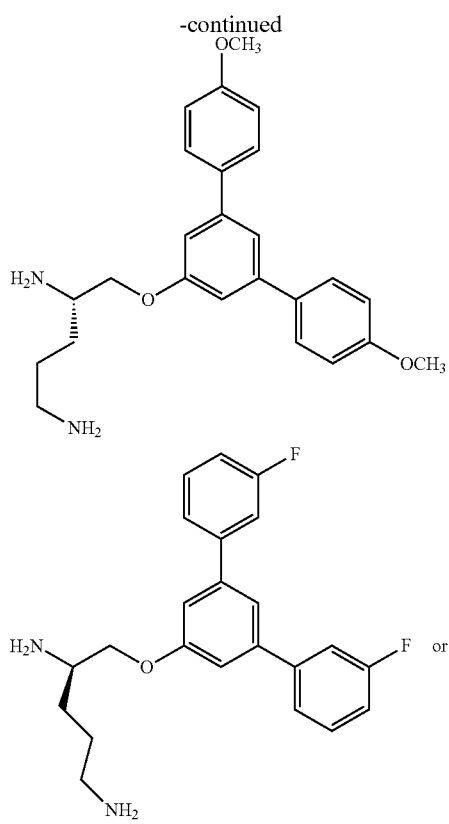

or a salt thereof.

16. The compound of claim 4, wherein $R^1$ is $(C_1-C_8)$alkyl substituted with one or more groups independently selected from —NR$^{b2}$R$^{c2}$.

17. The compound of claim 6, wherein $R^1$ is $(C_1-C_8)$alkyl substituted with one or more groups independently selected from —NR$^{b2}$R$^{c2}$.

18. A pharmaceutical composition comprising a compound as described in claim 4 or a pharmaceutically acceptable salt thereof, and a pharmaceutically acceptable vehicle.

19. A pharmaceutical composition comprising a compound as described in claim 6 or a pharmaceutically acceptable salt thereof, and a pharmaceutically acceptable vehicle.

* * * * *

UNITED STATES PATENT AND TRADEMARK OFFICE
CERTIFICATE OF CORRECTION

PATENT NO. : 10,836,706 B2  
APPLICATION NO. : 16/078572  
DATED : November 17, 2020  
INVENTOR(S) : Edmond J. LaVoie et al.

Page 1 of 1

It is certified that error appears in the above-identified patent and that said Letters Patent is hereby corrected as shown below:

In the Claims

Column 111, Lines 27-28, Claim 4, please delete "-C(-NR$^{a2}$)(NR$^{b2}$R$^{c2}$), -NR$^{a2}$C(-NR$^{a2}$)(R$^{d2}$) and –NR$^{a2}$C(-NR$^{a2}$)(NR$^{b2}$R$^{c2}$);" and insert -- -C(=NR$^{a2}$)(NR$^{b2}$R$^{c2}$), -NR$^{a2}$C(=NR$^{a2}$)(R$^{d2}$) and –NR$^{a2}$C(=NR$^{a2}$)(NR$^{b2}$R$^{c2}$) --;

Column 112, Line 20, Claim 6, please delete "NHNH$^2$" and insert -- NHNH$_2$ --; and Column 112, Lines 20-21, Claim 6, please delete "-C(-NR$^{a2}$)(NR$^{b2}$R$^{c2}$), -NR$^{a2}$C(-NR$^{a2}$)(R$^{d2}$) and –NR$^{a2}$C(-NR$^{a2}$)(NR$^{b2}$R$^{c2}$);" and insert -- -C(=NR$^{a2}$)(NR$^{b2}$R$^{c2}$), -NR$^{a2}$C(=NR$^{a2}$)(R$^{d2}$) and –NR$^{a2}$C(=NR$^{a2}$)(NR$^{b2}$R$^{c2}$); -- therefor.

Signed and Sealed this  
Eighth Day of June, 2021

Drew Hirshfeld  
*Performing the Functions and Duties of the*  
*Under Secretary of Commerce for Intellectual Property and*  
*Director of the United States Patent and Trademark Office*